United States Patent
Bayle et al.

(10) Patent No.: US 12,269,861 B2
(45) Date of Patent: Apr. 8, 2025

(54) CHIMERIC ILT RECEPTOR COMPOSITIONS AND METHODS

(71) Applicant: NKILT Therapeutics, Inc., Springfield, NJ (US)

(72) Inventors: Joseph Henri Bayle, West University Place, TX (US); MyLinh Thi Duong, Sugar Land, TX (US)

(73) Assignee: NKILT Therapeutics, Inc., Springfield, NJ (US)

( * ) Notice: Subject to any disclaimer, the term of this patent is extended or adjusted under 35 U.S.C. 154(b) by 0 days.

(21) Appl. No.: 18/164,417

(22) Filed: Feb. 3, 2023

(65) Prior Publication Data
US 2023/0348560 A1 Nov. 2, 2023

Related U.S. Application Data

(60) Provisional application No. 63/306,514, filed on Feb. 4, 2022.

(51) Int. Cl.
*A61P 35/00* (2006.01)
*C07K 14/725* (2006.01)
*C12N 15/63* (2006.01)

(52) U.S. Cl.
CPC .......... *C07K 14/7051* (2013.01); *A61P 35/00* (2018.01); *C12N 15/63* (2013.01); *C07K 2319/02* (2013.01); *C07K 2319/03* (2013.01)

(58) Field of Classification Search
CPC . C07K 14/7051; C07K 2319/02; C12N 15/63
USPC ...................................................... 424/93.1
See application file for complete search history.

(56) References Cited

U.S. PATENT DOCUMENTS

| | | | |
|---|---|---|---|
| 10,005,845 B2 | 6/2018 | Loustau et al. | |
| 10,139,662 B2 * | 11/2018 | Lee et al. | C07K 14/70535 514/9 |
| 11,111,302 B2 | 9/2021 | Demoyen et al. | |
| 11,117,971 B2 | 9/2021 | Loustau et al. | |
| 11,312,774 B2 | 4/2022 | Demoyen et al. | |
| 11,325,977 B2 | 5/2022 | Loustau et al. | |
| 2015/0093401 A1 * | 4/2015 | Pule | G01N 33/5005 435/375 |
| 2016/0272724 A1 | 9/2016 | Loustau et al. | |
| 2019/0233520 A1 | 8/2019 | Demoyen et al. | |
| 2020/0291087 A1 * | 9/2020 | Zhang | A61K 39/3955 |
| 2021/0040217 A1 | 2/2021 | Loustau et al. | |
| 2021/0054081 A1 | 2/2021 | Demoyen et al. | |
| 2021/0403574 A1 | 12/2021 | Loustau et al. | |
| 2022/0056140 A1 | 2/2022 | Demoyen et al. | |
| 2022/0251216 A1 | 8/2022 | Demoyen et al. | |
| 2022/0281981 A1 | 9/2022 | Loustau et al. | |

FOREIGN PATENT DOCUMENTS

| | | | | |
|---|---|---|---|---|
| WO | WO-2016065329 | * | 4/2016 | ............. C12N 5/078 |
| WO | WO-2020087054 A1 | * | 4/2020 | ......... C07K 14/7151 |
| WO | 2021030149 | | 2/2021 | |

OTHER PUBLICATIONS

U.S. Appl. No. 15/518,976, filed Apr. 13, 2017, Maute et al.*
Wall et al., Theriogenology, vol. 45, p. 57-68, 1996 (Year: 1996) (Year: 1996).*
Baxenvanis, Antibody- based cancer therapy, Expert Opin. Drug Discov. 3(4):441-452 (Year: 2008).*
J Cuzick et al, Overview of the main outcomes of breast cancer, p. 296-300 (Year: 2003).*
Evans et al, Vaccine therapy for Cancer- fact or fiction, pp. 299-307 (Year: 1999).*
Komenaka et al, Immunotherapy for Melanoma, pp. 251-265, (Year: 2004).*
B. Hernández-Ledesma et al. / Peptides 30 (2009) 426-430 (Year: 2008).*
Schiffman et al. The promise of Global Cervical- Cancer Prevention, pp. 2101-2104 (Year: 2005).*
Burgess et al, Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, Laboratory of Molecular Biology, (Year: 1990).*
Iazar et al, Transforming Growth Factor ox: Mutation of Aspartic Acid 47 and Leucine 48 Results in Different Biological Activities, vol. 8, No. 3, p. 1247-1252 (Year: 1987).*
Baker et al, Conversion of a T Cell Antagonist into an Agonist by Repairing a Defect in the TCR/Peptide/MHC Interface: Implications for TCR Signaling, Immunity, vol. 13, 475-484, Oct. 2000 (Year: 2000).*
Shuan Shian Huang et al, J. Biol. Chem. 1997, 272:27155-27159. (Year: 1997).*
Martindale et al, Nature genetics, vol. 18 (Year: 1998).*
James U. Bowie et al, Deciphering the Message in Protein Sequences: Tolerance to Amino Acid Substitutions, Science, vol. 247 (Year: 1990).*

(Continued)

*Primary Examiner* — Sean E Aeder
(74) *Attorney, Agent, or Firm* — Kyle A. Gurley; Bozicevic, Field & Francis LLP

(57) ABSTRACT

Provided are chimeric ILT receptors (CIRs) that include a targeting region from ILT2 or ILT4, a transmembrane domain, and an intracellular domain (ICD). The ICD includes a signaling region (e.g., CD3 zeta (CD3ζ)) and optionally a costimulatory region (e.g., CD28, 4-1BB, OX40, and the like). Also provided are nucleic acids (e.g., expression vectors) encoding a subject CIR, and genetically modified cells (e.g., immune cells such as NK cells, T cells, iNKT cells, macrophages, and the like) expressing a subject CIR. For example, provided are genetically modified immune cells such as NK cells that include a nucleic acid encoding an ILT2 or ILT4 CIR. The subject CIRs are designed to activate cytotoxicity by immune cells such as NK cells, T cells, iNKT cells and macrophages against HLA-G expressing cancers.

Figure 1A:
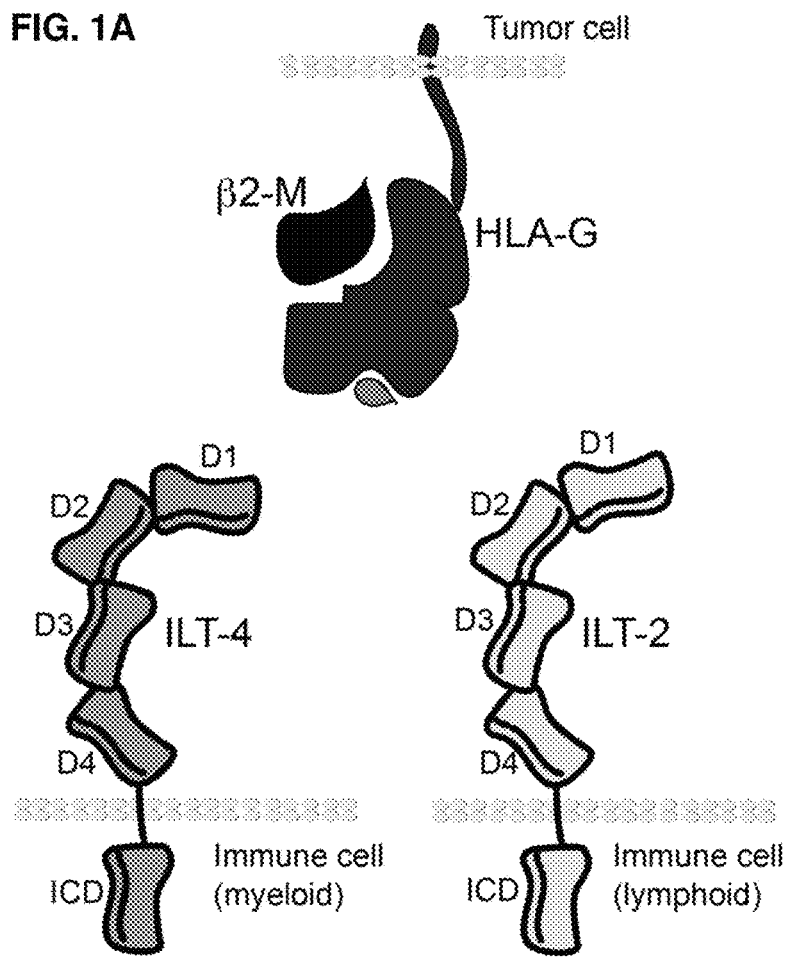

19 Claims, 18 Drawing Sheets
Specification includes a Sequence Listing.

(56) References Cited

OTHER PUBLICATIONS

Ju et al, Conversion of the interleukin 1 receptor antagonist into an agonist by site-specific mutagenesis, Proc. Natl. Acad. Sci. USA vol. 88, pp. 2658-2662, Apr. 1991 Immunology (Year: 1991).*
Freiss et al., Cancer Res 2005; 65: (22). Nov. 15, 2005.*
Montrase et al, J. Biol. Chem. 1997, 272:21201-21206 (Year: 1997).*
Nonaka et al, Human Molecular Genetics, 2009, vol. 18, No. 18 3353-3364 (Year: 2009).*
Shiroishi et al, Human inhibitory receptors Ig-like transcript 2 (ILT2) and ILT4 compete with CD8 for MHC class I binding and bind preferentially to HLA-G, PNA, Jul. 22, 2003, vol. 100.*
Deng et al (Blood, Aug. 7, 2014, vol. 124).*
Borges et al (The Journal of Immunology, 1997, 159(11): 5192-5196).*
Yazdanifar et al (Cells, 2019, 8, 1070, 1-23).*
Anna et al. (2021) "First immunotherapeutic CAR-T cells against the immune checkpoint protein HLA-G", J Immunother Cancer, 9(3): 1-14.
Altenschmidt et al. (1996) "Cytolysis of Tumor Cells Expressing the Neu/erbB-2, erbB-3, and erbB-4 Receptors by Genetically Targeted Naive T Lymphocytes", Clin. Cancer Res., 2:1001-1008.
Muniappan et al. (2000) "Ligand-mediated cytolysis of tumor cells: Use of heregulin-ζ chimeras to redirect cytotoxic T lymphocytes", Cancer Gene Ther., 7:128-134.
Zhang et al. (2012) "An NKp30-based chimeric antigen receptor promotes T-cell effector functions and anti-tumor efficacy in vivo", J Immunol., 189:2290-2299.
Ramírez-Chacón et al., (2022) "Ligand-based CAR-T cell: Different strategies to drive T cells in future new treatments", Frontiers in Immunology, pp. 1-17.
Shiroishi et al., (2003) "Human inhibitory receptors Ig-like transcript 2 (ILT2) and ILT4 compete with CD8 for MHC class I binding and bind preferentially to HLA-G", Proceedings of the National Academy of Science, 100:15:8856-8861.
Wong et al., (2003) "Stalk Region of beta-Chain Enhances the Coreceptor Function of CD8I", The Journal of Immunology, 171(2):867-874.
Invectys Inc., *Invectys USA Inc., and Invectys, SAS, v. Nkilt Therapeutics, Inc., SWH Consulting, Sasu and Simon Wainhobson*, Case No. 4:23-cv-4436 (Filed on Nov. 22, 2023 in TXSD), "Complaint", pp. 1-85.
Invectys Inc., *Invectys USA Inc., and Invectys, SAS, v. Nkilt Therapeutics, Inc., SWH Consulting, Sasu and Simon Wainhobson*, Case No. 4:23-cv-4436 (Filed on Mar. 11, 2024 in TXSD), "Defendants' Partial Motion to Dismiss Count III Pursuant To Rule 12(B)(1) and Rule 12(B)(6)", pp. 1-8.
Invectys Inc., *Invectys USA Inc., and Invectys, SAS, v. Nkilt Therapeutics, Inc., SWH Consulting, Sasu and Simon Wainhobson*, Case No. 4:23-cv-4436 (Filed on Mar. 29, 2024 in TXSD), "First Amended Complaint", pp. 1-102.
Invectys Inc., *Invectys USA Inc., and Invectys, SAS, v. Nkilt Therapeutics, Inc., SWH Consulting, Sasu and Simon Wainhobson*, Case No. 4:23-cv-4436 (Filed on Apr. 12, 2024 in TXSD), "Defendant Nkilt Therapeutics, Inc.'S Answer to Plaintiff's Amended Complaint and Affirmative Defenses to Counts I Through VII", pp. 1-17.
Invectys Inc., *Invectys USA Inc., and Invectys, SAS, v. Nkilt Therapeutics, Inc., SWH Consulting, Sasu and Simon Wainhobson*, Case No. 4:23-cv-4436 (Filed on Apr. 12, 2024 in TXSD), "Defendants SWH Consulting, Sasu, and Simon Wain-Hobson's, Answer to Plaintiff's Amended Complaint and Affirmative Defenses To Counts I Through VII", pp. 1-17.
Apps et al., (2007) "A homodimeric complex of HLA-G on normal trophoblast cells modulates antigen-presenting cells via LILRB1", Eur. J. Immunol., 37:1924-1937.
Giles, (2012) "HLA-B27 Homodimers and Free H Chains Are Stronger Ligands for Leukocyte Ig-like Receptor B2 than Classical HLA Class I", J Immunol. 188(12):6184-6193.
Shiroishi et al., (2006) "Structural basis for recognition of the nonclassical MHC molecule HLA-G by the leukocyte Ig-like receptor B2 (LILRB2/LIR2/ILT4/CD85d)", PNAS, 103(4): 16412-16417.

* cited by examiner

Immune cell inactivation

Immune cell activation

Immune cell activation

FIG. 6A

| Construct | Domains |
|---|---|
| ILT4 FL | D1 – D2 – D3 – D4 – ILT4STM – ILT4 ICD |
| ILT4 CIR1 | D1 – D2 – D3 – D4 – ILT4STM – BB.ζ |
| ILT4 CIR2 | D1 – D2 – ILT4STM – BB.ζ |
| ILT4 CIR3 | D1 – D2 – D3 – D4 – CD8aSTM – BB.ζ |
| ILT4 CIR4 | D1 – D2 – CD8aSTM – BB.ζ |
| ILT2 FL | D1 – D2 – D3 – D4 – ILT2STM – ILT2 ICD |
| ILT2 CIR1 | D1 – D2 – D3 – D4 – ILT2STM – BB.ζ |
| ILT2 CIR2 | D1 – D2 – ILT2STM – BB.ζ |
| ILT2 CIR3 | D1 – D2 – D3 – D4 – CD8aSTM – BB.ζ |
| ILT2 CIR4 | D1 – D2 – CD8aSTM – BB.ζ |
| HLAG CAR | HLA-Gh – HLA-Gl – CD8aSTM – BB.ζ |
| CD33 CAR | CD33h – CD33l – CD8aSTM – BB.ζ |

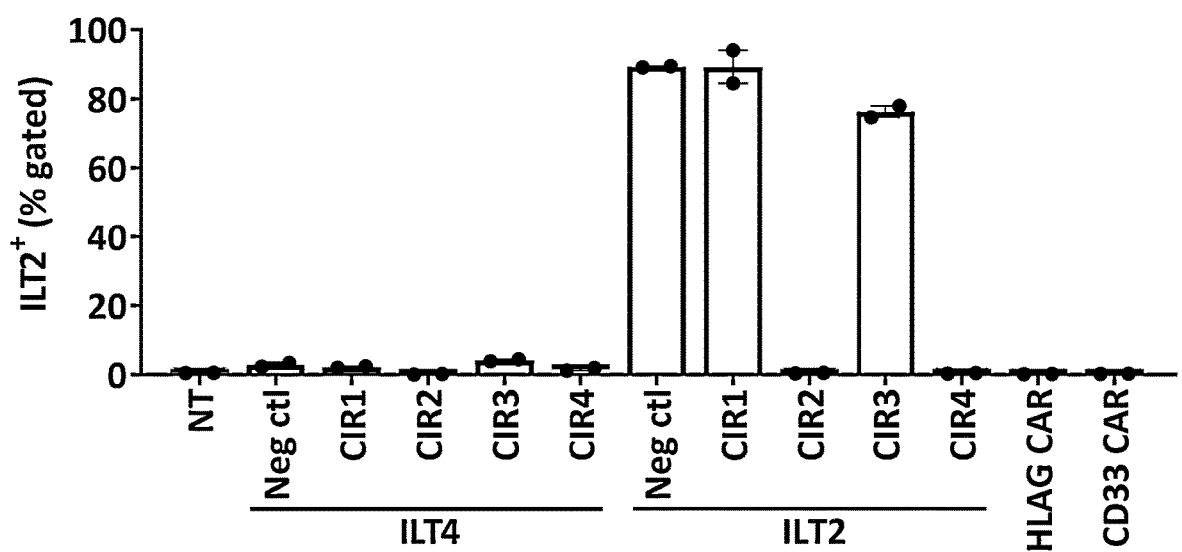

FIG. 9

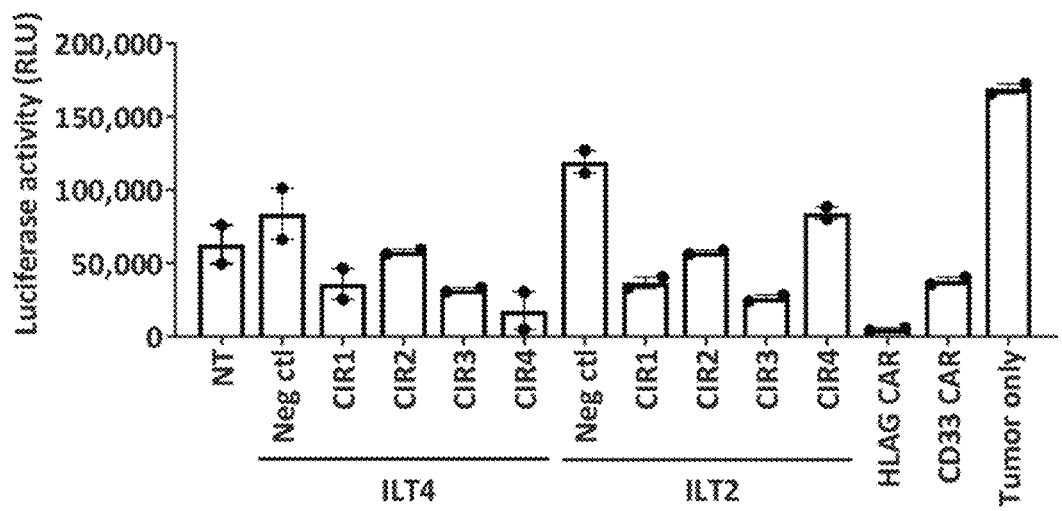

FIG. 10

| Component | Short name |
|---|---|
| ILT4(D1-D2).CD8stalktm.BB.z.T2A-dCD19 | ILT4 CD8s.CD8tm CIR4 |
| ILT4(D1-D2).CH2CH3s.CD8tm.BB.z.T2A-dCD19 | ILT4 CH2CH3s.CD8tm CIR6 |
| ILT4(D1-D2).CH3s.CD8tm.BB.z.T2A-dCD19 | ILT4 CH3s.CD8tm CIR7 |
| ILT4(D1-D2).CH2CH3s.CD28tm.BB.z.T2A-dCD19 | ILT4 CH2CH3s.CD28tm CIR8 |
| ILT4(D1-D2).CH3s.CD28tm.BB.z.T2A-dCD19 | ILT4 CH3s.CD28tm CIR9 |
| ILT4(D1-D2).CD28s.CD28tm.BB.z.T2A-dCD19 | ILT4 CD28s.CD28tm CIR10 |
| HLAG(15E7).CD8StalkTM.BB.z.T2A-dCD19 | HLAG CAR |

| NT | CD8 | CH2CH3 | CH3 | CH2CH3 | CH3 | CD28 | Stalk |
|---|---|---|---|---|---|---|---|
|  | CD8 | CD8 | CD8 | CD28 | CD28 | CD28 | Transmembrane |
|  | CIR4 | CIR6 | CIR7 | CIR8 | CIR9 | CIR10 |  |

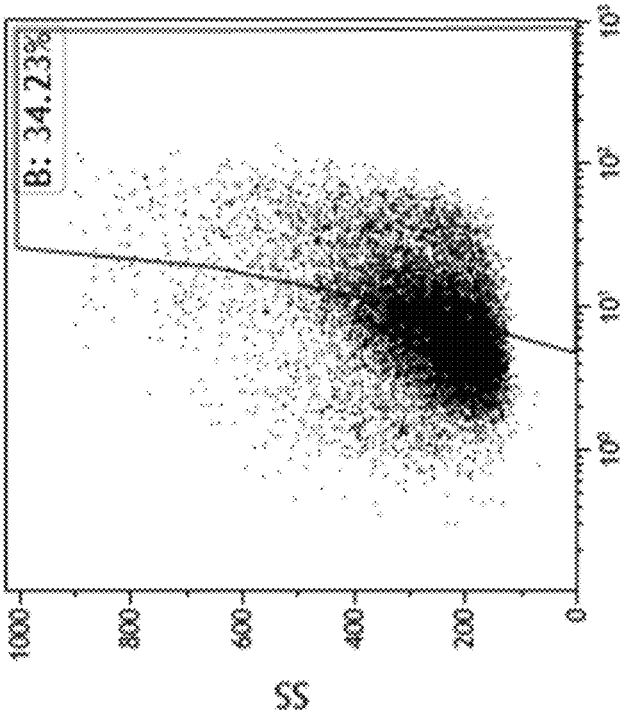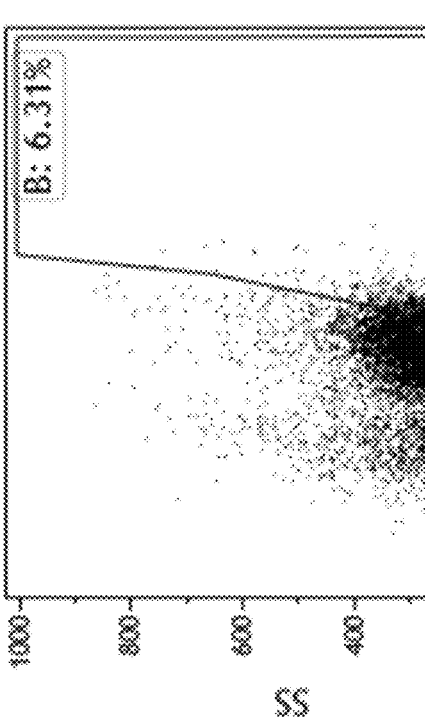
FIG. 12

CHIMERIC ILT RECEPTOR COMPOSITIONS AND METHODS

CROSS REFERENCE

This application claims benefit of U.S. Provisional Patent Application No. 63/306,514, filed Feb. 4, 2022, which application is incorporated herein by reference in its entirety.

INCORPORATION BY REFERENCE OF SEQUENCE LISTING PROVIDED AS AN XML FILE

A Sequence Listing is provided herewith as a Sequence Listing XML, "NKLT-001_SEQ_LIST_revised.xml" created on Apr. 23, 2024 and having a size of 145,672 bytes. The contents of the Sequence Listing XML are incorporated by reference herein in their entirety.

I. INTRODUCTION

Immune cell therapy is useful for specifically targeting diseased cells. This treatment can be potentially curative for both malignant and non-malignant conditions. For example, donor lymphocyte infusions, allogeneic T cells and allogeneic Natural Killer (NK) cells can be used to control the outgrowth of leukemias. Further, gene modification can direct the specificity of immune cells including T cells, Natural Killer (NK) cells, γδ T cells, inducible NKT cells and macrophages toward a given target cell population for therapeutic purposes. For example, Chimeric antigen receptor (CAR) T cells can be used to redirect T cell specificity to tumor-associated cell surface molecules independent of Human Leukocyte Antigen (HLA). Clinical trials have shown efficacy of CAR-T therapies especially in haematological malignancies such as B cell leukemias and lymphomas by targeting antigens such as CD19 or B cell maturation antigen (BCMA) for multiple myeloma. These targets have discrete expression in B cells and plasma cells as well as their respective tumor types and the aplasias resulting from off-tumor targeting by CD19 and BCMA CAR-T cells can be replaced by immunoglobulin replacement therapy. Three autologous CD19 CAR-T cell therapy products have been approved by the US FDA. More recently therapeutic efficacy has been demonstrated with CAR-expressing NK (CAR-NK) cells directed against CD19.

Acute myeloid leukemia (AML), also called acute myelogenous leukemia, is a disease of transformed myeloid progenitor cells and cells more differentiated toward the monocyte lineage. CAR-T therapy against targets such as CD33 and CD123 expressed on AML blasts is challenged by expression of the targets on normal myeloid progenitor cells for which ablation from therapy results in highly adverse cytopenias. There is a need for CAR or other directed cell therapy against more discretely expressed targets on AML. One such target is the Class 1B (or non-classical) MHC-1 protein HLA-G.

HLA-G is abundantly expressed on the surface of the trophoblasts of the fetal placenta where it provides a barrier for the fetus from immune attack by the mother through its potent inhibition of most classes of lymphoid and myeloid cells. HLA-G is overexpressed in diverse tumor types including AML as a mechanism to evade immune attack thereby promoting tumor outgrowth while hematopoietic progenitors do not express HLA-G due to their innate tolerance from immune attack.

The HLA-G gene produces multiple different RNA transcripts via alternative mRNA splicing that in turn produce at least seven different protein products. These protein products can exist either on the plasma membrane of tumor cells or as secreted forms within the tumor microenvironment with or without complex formation with β2-microglobulin (β2-M). Further, HLA-G can exist as a monomeric or disulphide-linked homodimer with an altered tertiary structure. Traditional CAR-T products utilize single chain fragments (scFv) derived from antibodies or camelid-derived VhH domains in the chimeric receptor to target antigens. The epitope targeted by a given scFv on HLA-G is likely to be eliminated or occluded in several HLA-G isoforms placing a selection for tumor cells expressing isoforms that eliminate the expression of isoforms containing this epitope but retaining the immunosuppressive activity of HLA-G. There is a need for a targeting agent for cell therapy against HLA-G that includes all the isoforms capable of immunosuppression.

II. SUMMARY

Provided by the present disclosure is a genetically modified cell engineered to express a chimeric receptor protein that has affinity and specificity such that the modified cell can stimulate an immune response in a subject. For example, the chimeric receptor protein may target a protein expressed at high level in tumor tissue relative to untransformed, normal tissue and generate a cytotoxic or inflammatory response against the tumor. A CAR is frequently employed to generate antigen-specific recognition of tumor tissues based on the affinity and specificity permitted by antibody-antigen interactions. For the compositions and methods of the present disclosure, affinity and specificity are not maintained by use of antibody- or VhH-relationship or by binding of randomly generated peptides to a target antigen, but rather by use of ligand:receptor interactions where affinity and specificity are maintained by evolution.

For example, in a preferred embodiment, the genetically modified cells express a chimeric receptor that has high affinity for HLA-G, a target protein that can exist on tumor tissues in one or more of seven known forms generated by alternative mRNA splicing and post-translational modifications. HLA-G naturally acts as an agent to suppress immune responses through engagement with the negatively signaling Immunoglulin-like Transcript 2 (ILT2) and ILT4 receptors on the surface of immune cells. In these preferred embodiments, T cells, NK cells, iNKT cells or macrophages are engineered such that recognition of active forms HLA-G by ILT2 or ILT4 instead generate activating signals. In these preferred embodiments, the intracellular signalling elements of ILT2 or ILT4 are excised and replaced with ITAM-containing signalling domains of the CD3ζ chain that drive immune cell activation and cytotoxicity. Such a protein is termed a 'Chimeric ILT Receptor' or 'CIR'.

Thus, provided are chimeric ILT receptors (CIRs) [plus nucleic acids encoding them and genetically modified cells, such as immune cells, expressing them], which include a targeting region from ILT2 or ILT4, a transmembrane domain, and an intracellular domain (ICD), which includes a signaling region (e.g., CD3 zeta (CD3ζ)) and optionally a costimulatory region (e.g., CD28, 4-11BB, OX40, and the like). The inventors appreciate that this approach provides an advantage over using an antibody-based targeting region (such as an scFv). An antibody-based targeting approach could cause a selection for tumor cells that express HLA-G isoforms that lack the targeted epitope—thus allowing a cancer to evade treatment. To the contrary, a subject ILT2 or ILT4 based chimeric ILT receptor should target many more, and perhaps all, HLA-G isoforms because ILT2 and ILT4 naturally bind those isoforms. This will greatly reduce, and perhaps eliminate, the ability of cancer cells to evade treatment by selection for a particular HLA-G isoform.

ILT2 and ILT4 are structurally similar in the extracellular region and are composed of four folded domains (D1, D2, D3 and D4) arranged in a distal-to-proximal fashion relative to the plasma membrane of the cell. HLA-G interacts with the D1 and D2 domains of ILT2 and ILT4 and these D1 and D2 domains can be separated from the rest of the ILT proteins while maintaining interaction with HLA-G. Cellular proteins other than HLA-G can interact with the D3 and D4 domains of ILT4. To prevent off-target interactions with these proteins that could generate toxicity in a therapeutic setting, it is desirable to abolish such off-HLA-G interactions. Thus, in some embodiments, ILT2 or ILT4 D3-D4 is replaced in the chimeric receptor fusion with another extracellular domain that serves as a stalk and transmembrane domain to present ILT2 or ILT4 D1-D2 to HLA-G expressing target cells. Examples of stalk proteins to present D1-D2 are derived from CD28, CD8α, the CH2-CH3 region of IgG4, HER2 membrane proximal, and mGluR2. In other embodiments, the D3-D4 domains of ILT2 and ILT4 are simply deleted. As such, in some embodiments a subject chimeric ILT receptor includes D1-D2 of ILT2, but lacks D3-D4 of ILT2. In some embodiments a subject chimeric ILT receptor includes D1-D2 of ILT4, lacks D3-D4 of ILT4.

Some proteins can make binding interactions with the D1 and D4 regions of ILT4. In the context of removal of D4, it is probable that such interactions with D1 alone will be weak. To further reduce unwanted interaction with other cellular proteins that HLA-G, in some embodiments mutations that encode amino acid replacements in D1 of ILT4 are made. For example, tyrosine 96 can be replaced with any amino acid including alanine.

In still further embodiments, costimulatory elements to improve the survival, persistence, cytotoxicity and capacity to secrete cytokines as part of an immune response are included as part of the intracellular portion of the chimeric receptor, and in other embodiments the costimulatory elements are engineered for expression separated from the chimeric receptor. These costimulatory elements can be derived from any or a combination of any of these proteins: 4-11BB, OX40, ICOS, CD28, CD27, MyD88, IL-1 Rα, HVEM, TRANCE, IL-1 Rβ, IL-18Rα, CD40, IL-18Rβ, CD30, IL-33Rα, BCMA or IL-33β.

In some embodiments, a safety switch can be coexpressed with the chimeric receptor protein in the same cell. The purpose of the switch is to reduce toxicity potentially generated by gene modified cells containing the CIR. Such toxicity may result from hyperactivity causing cytokine release syndrome (CRS), immune cell activated neurotoxic syndrome (ICANS), off-target, off-tumor interaction or targeting against normal tissue that may express HLA-G. In one such embodiment the safety switch is inducible Caspase-9 (iC9), a fusion of a variant FKBP12 with a truncated version of caspase-9 such that the proapoptotic activity of the caspase is under control of the synthetic dimerizer ligand, rimiducid.

Reagents, compositions, kits/systems, and methods related to chimeric ILT receptors are provided. For example, provided are methods of making genetically modified cells and methods of treatment (e.g., administering an immune cell, such as an NK cell, a T cell, or a macrophage, that expresses a subject CIR to an individual).

III. BRIEF DESCRIPTION OF THE DRAWINGS

Figure 1B:
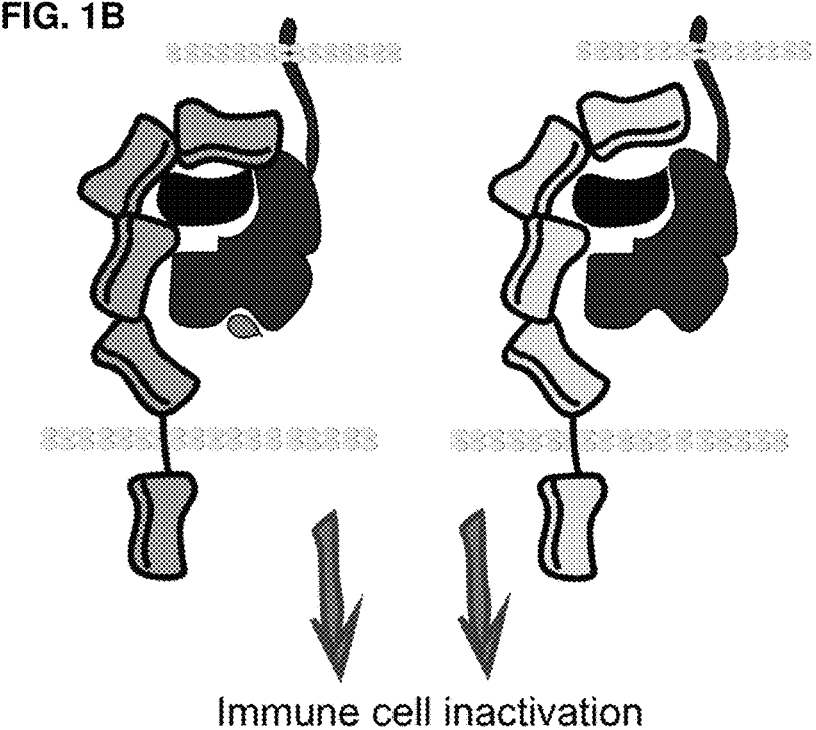

The following detailed description of embodiments of the invention will be better understood when read in conjunction with the appended drawings. It should be understood that the invention is not limited to the precise arrangements and instrumentalities of the embodiments shown in the drawings. The drawings illustrate certain embodiments of the technology and are not limiting. For clarity and ease of illustration, the drawings are not made to scale, and, in some instances, various aspects may be shown exaggerated or enlarged to facilitate an understanding of particular embodiments FIG. 1A-1B. HLA-G and inhibitory receptors for HLA-G. (FIG. 1A) Schematic representation of HLA-G1 tethered to the plasma membrane of a tumor cell in complex with β2-M. Also depicted are the receptors for HLA-G, the ILT2 protein primarily expressed on lymphocytes and ILT4 primarily expressed on cells derived from the myeloid lineage. Four separately folded extracellular domains on ILT2 and ILT4 proteins are labeled D1-D4 according to their proximity to the plasma membrane. The intracellular signalling domain (ICD) is also depicted. (FIG. 1B) Depiction of ILT4 (left) or ILT2 in complex with HLA-G. Unlike classical MHC-I interaction through a peptide binding cleft, ILT proteins interact with the membrane proximal α3 domain of HLA-G and with β2-M. Complex formation initiates signalling from the ICD of ILT2 or ILT4 and inhibition of immune cell activation.

Figure 2:
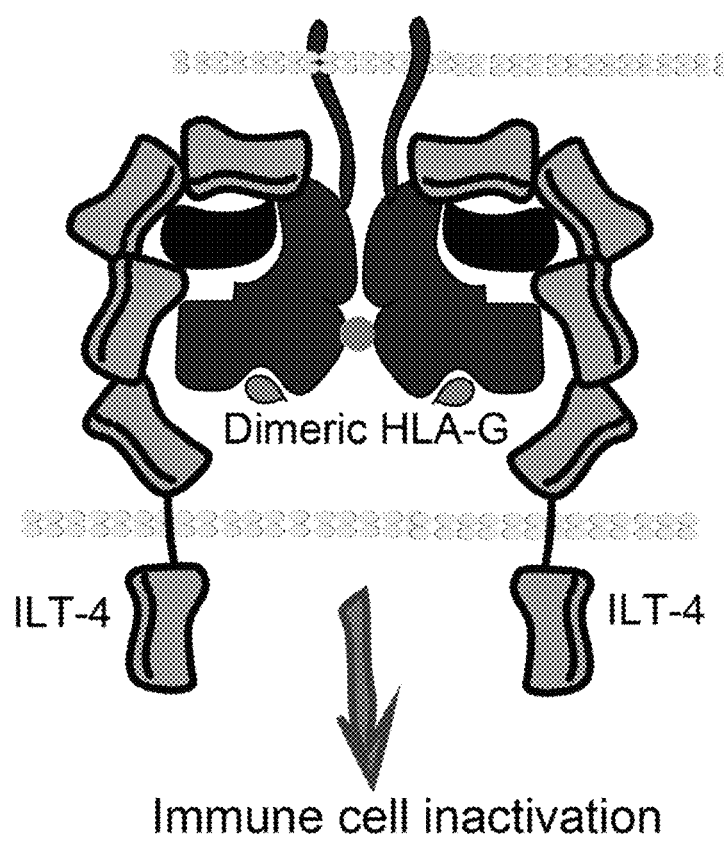

FIG. 2. ILT4 complex formation with dimeric HLA-G. A subset of HLA-G proteins form disulphide linked dimers in the α1 or α3 domains. Dimeric HLA-G has a higher affinity for ILT2/4 likely through an avidity effect that leads to enhanced ILT signalling and immune cell suppression.

Figure 3A:
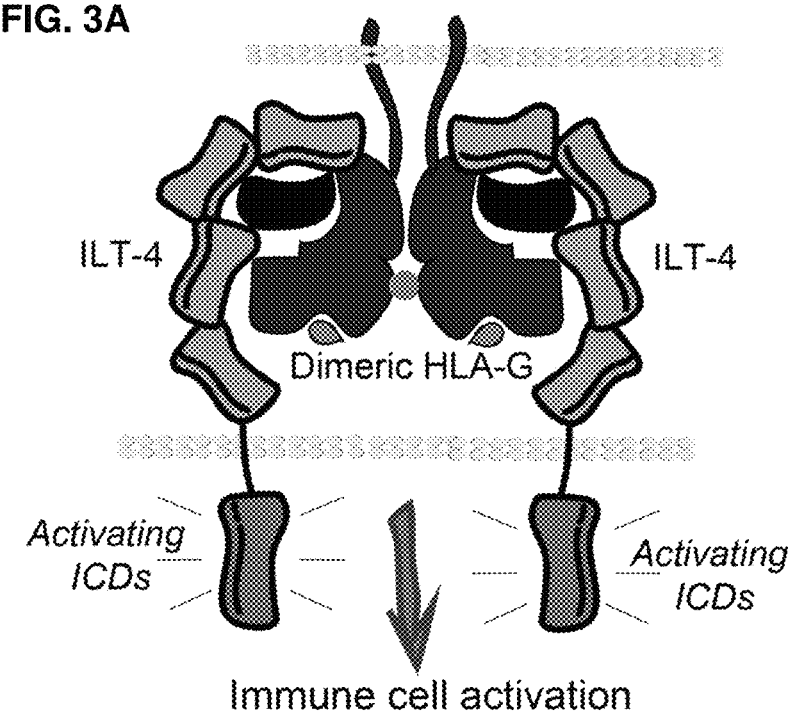
Figure 3B:
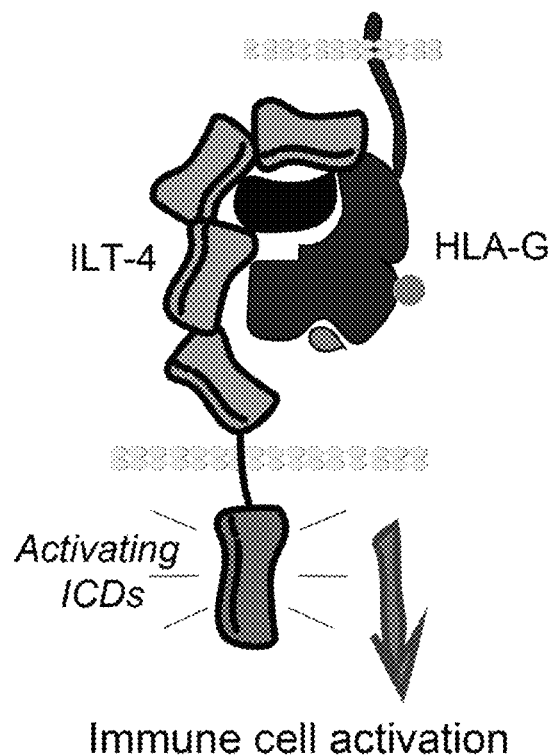

FIG. 3A-3B. Chimeric ILT proteins for immune cell activation. (FIG. 3A) Schematic depiction of a chimeric ILT4 receptor (CIR) in which the native ICD of ILT4 is replaced with a signalling domain derived from an immune cell activating receptor or activating adaptor protein. Engagement of the CIR with dimeric HLA-G initiates signalling that activates the immune cell. (FIG. 3B) Representation of a Chimeric ILT4 Receptor in complex with monomeric HLA-G.

Figure 4A:
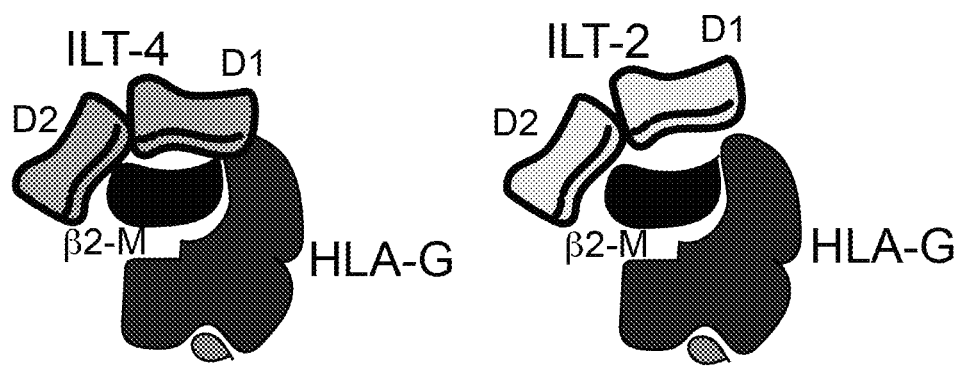
Figure 4B:
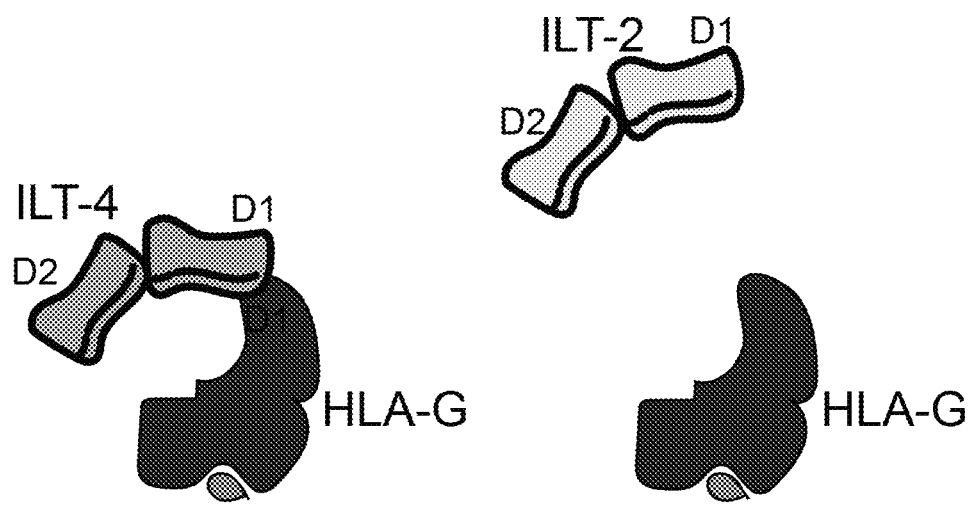

FIG. 4A-4B. Interaction of ILT2 and ILT4 D1 and D2 domains with the HLA-G isoforms. (FIG. 4A) Cartoon depiction of isolated ILT4 (left) and ILT2 (right) in complex with the HLA-G1 isoform. The D3 and D4 domains of ILT proteins are not essential for interaction with HLA-G. (FIG. 4B) Cartoon depiction of isolated ILT4 (left) and ILT2 (right) in complex with the HLA-G1 isoform.

Figure 5A:
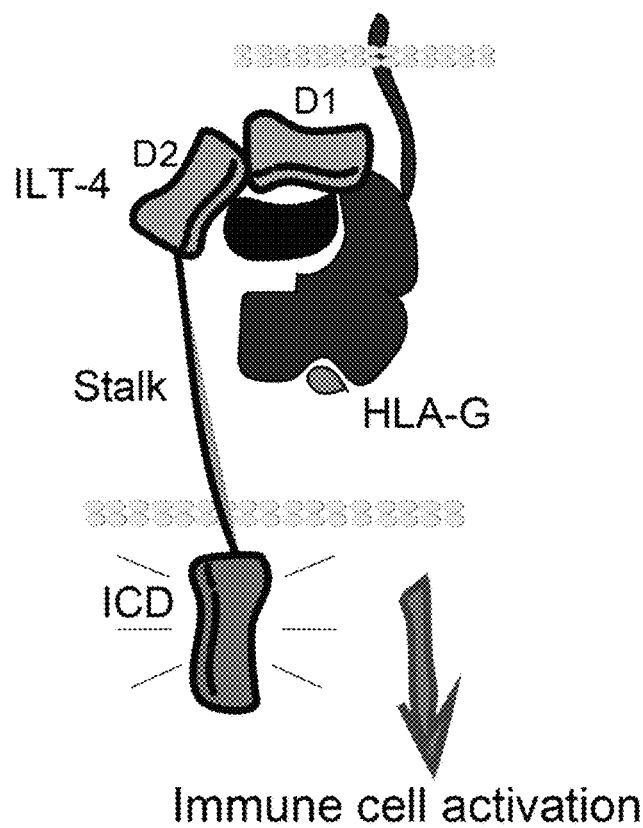
Figure 5B:
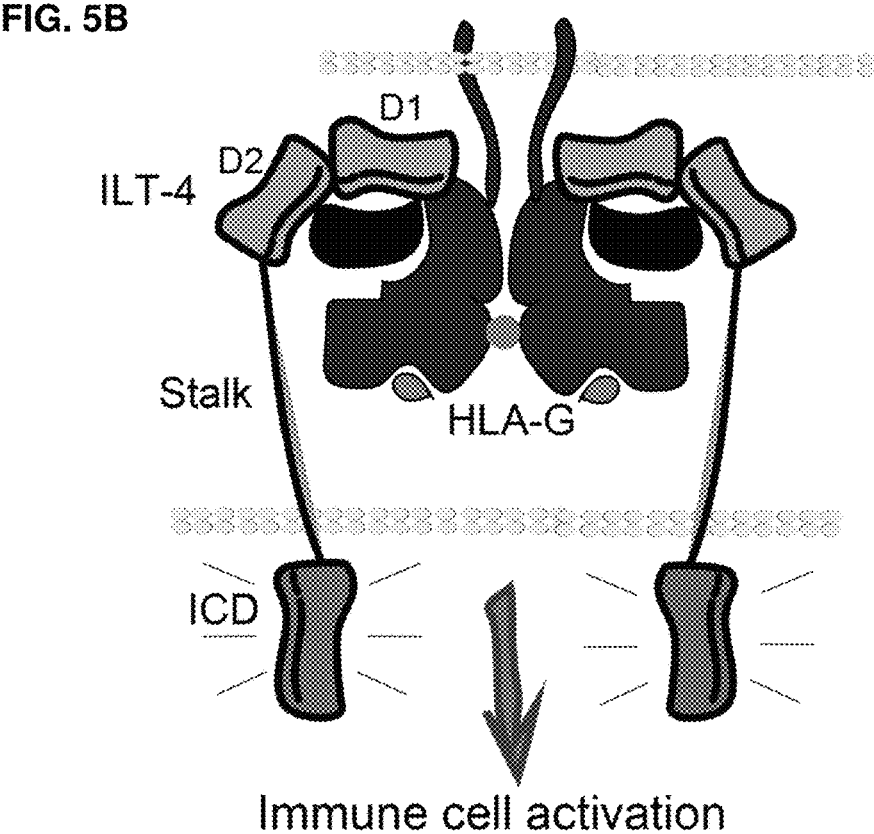

FIG. 5A-5B. Interaction of an ILT4 D1 D2 CIR with HLA-G. (FIG. 5A) Cartoon depiction of the D1 and D2 domains of ILT4 fused as a chimeric hybrid with a stalk and transmembrane domain derived from a separate protein and further fused with an activating intracellular signalling moiety. Interaction of D1D2 with HLA-G initiates signalling to activate immune cells. (FIG. 5B) Interaction of a stalk containing ILT4 D1D2 CIR with dimeric HLA-G.

FIG. 6A-6E: Transduction and expression of CIR proteins from constructed γ-retroviral vectors. (FIG. 6A) Schematic diagram of retroviral constructs expressing ILT2 and ILT4 fusion proteins referred to as Chimeric ILT Receptors (CIRs). D1 through D4 indicate the encoding of extracellular domains D1 through D4 derived from native ILT2 or ILT4. STM refers to the stem (S), a linker domain linking extracellular D domains with the transmembrane spanning domain (TM) these are derived from ILT2, ILT4 or CD8α

(CD8a). FL refers to the full-length version of native ILT2 and ILT4. ILT2 and ILT4 ICD refer to the native intracellular domains of ILT2 and ILT4 that promote inhibitory signals to immune cells. BB.ζ refers to intracellular domains derived from fusion with the costimulatory domain of 4-1 BB and signaling domain of CD3-ζ each of which promote activating signals to immune cells. Each of these γ-retroviral constructs also encodes a separate marker protein ΔCD19 to determine the efficien1cy of transduction. Also see Tables 13B, 15B, 16B, 20B, 21B, 23B, 24B, 28B, 36, and 37 (FIG. 6B) Transduction of retroviral constructs into primary human T cells. Flow cytometry plots indicate the expression of the ΔCD19 marker protein linked with expression of CIR constructs together with the expression of separately cotransduced marker virus encoding Orangenanolantern rennila luciferase (ONL). Indicated plots are representative of T cells derived from one of two healthy blood donors. Neg ctl indicates the transduction of ILT2 and ILT4 full length constructs that express the full length (FL) proteins for ILT2 and ILT4 which are inhibitory to T cell function and serve as a negative control (Neg. Ctl.) (FIG. 6C) Quantitation of the efficiency of retroviral transduction into primary human T cells (N=2) donors. (FIG. 6D) Expression of ILT4 extracellular domain in transduced human T cells at day 7 post-transduction determined by the mean fluorescence intensity of antibody staining determined by flow cytometry. (FIG. 6E) Expression of ILT2 extracellular domain in transduced human T cells at day 7 post-transduction determined by the mean fluorescence intensity of antibody staining determined by flow cytometry.

Figure 7A:
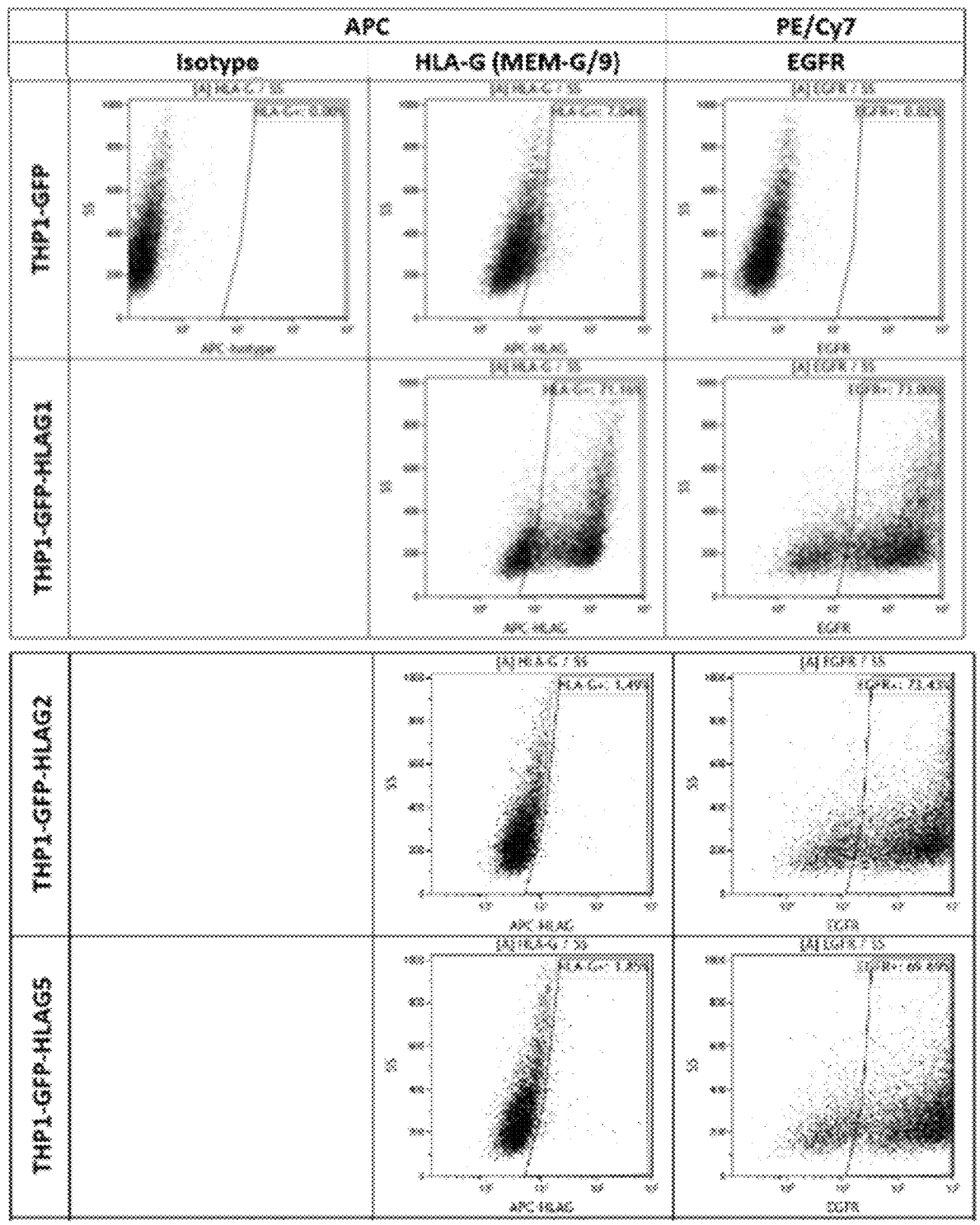
Figure 7B:
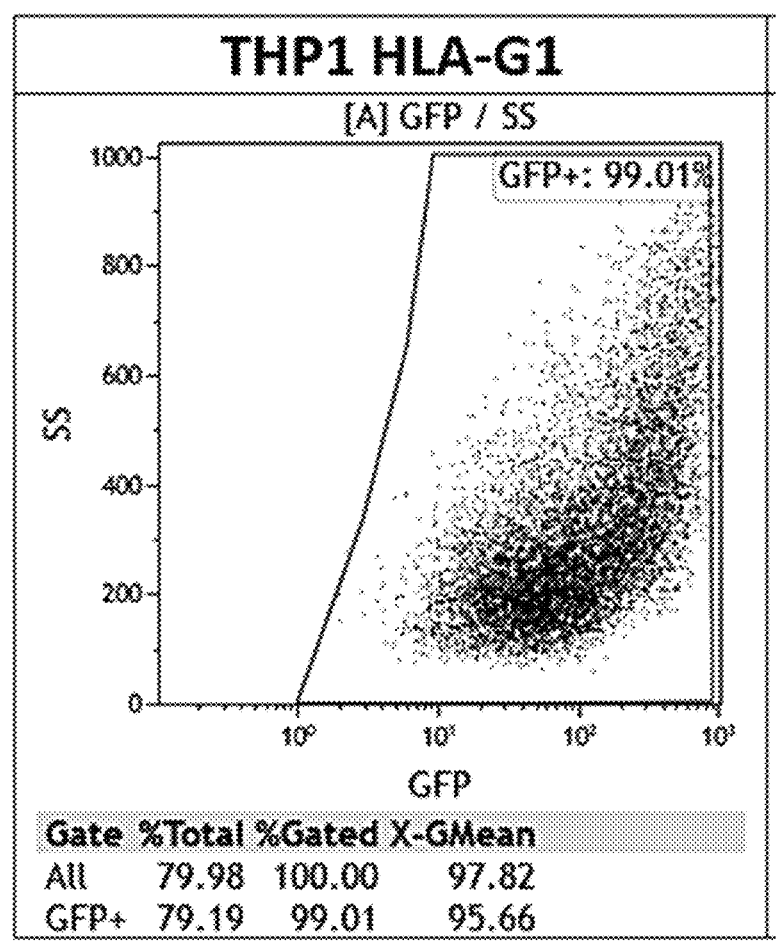

FIG. 7A-7B: Transgenic expression of HLA-G isoforms in THP1 Acute Myeloid Leukemia cells. (FIG. 7A) Stable expression of γ-retroviral constructs expressing HLA-G1, HLA-G2 and HLA-G5 in THP1 cells that lack endogenous HLA-G protein expression. Transduction efficiency is marked by the expression of ΔEGFR coexpressed by the retroviral construct. HLA-G1 expression is readily detected by flow cytometry with the MEM-G/9 antibody that is specific for HLA-G1. (FIG. 7B) Stable expression of GFP-fMuciferase in THP1 cells also stably expressing HLA-G1.

Figure 8:
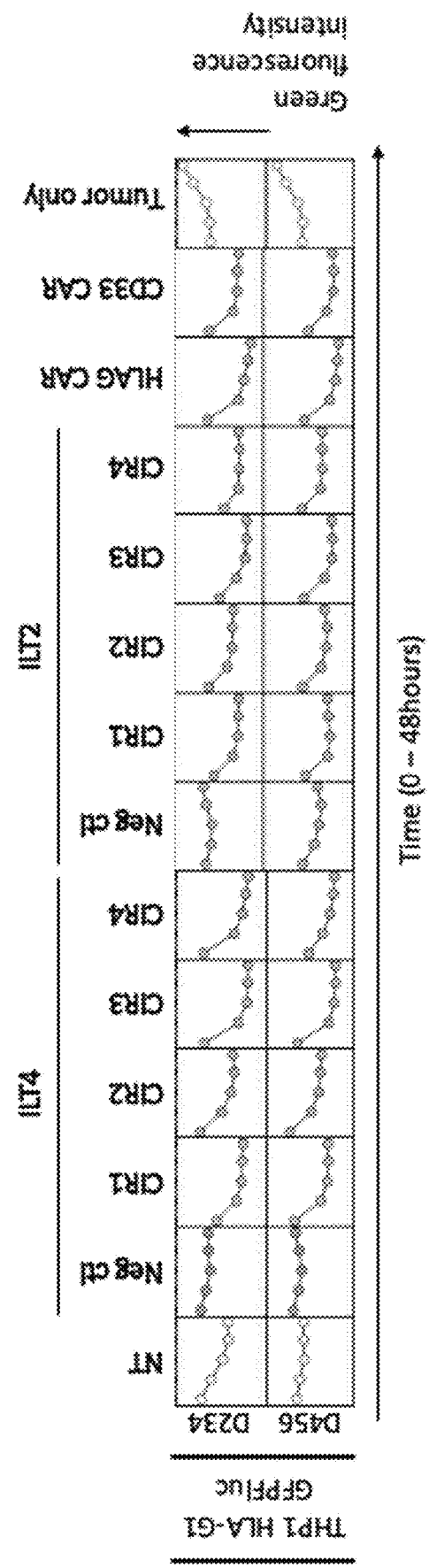

FIG. 8: Control of THP1-HLA-G1 cell expansion with CIR-T cells. Primary human T cells (N=2 donors) transduced with the indicated ILT2 and ILT4 CIR constructs or full length ILT2 or ILT4 (Neg Ctl) were cocultured with THP1 cells stably transduced with the HLA-G1 isoform and the GFP-fMuc marker. THP1 expansion or killing was measured periodically by GFP fluorescence in an Incucyte microscopic incubator over 48 hours. T cells expressing and HLAG1 specific Chimeric Antigen Receptor (HLA-G CAR) or a AML-targeting CD33-specific CAR (CD33 CAR) served as a positive control. NT=Not transduced.

FIG. 9: Short term cytotocity of CIR-T cells. Primary human T cells (N=2 donors) transduced with the indicated ILT2 and ILT4 CIR constructs or full length ILT2 or ILT4 (Neg Ctl) were cocultured with THP1 cells stably transduced with the HLA-G1 isoform and the GFP-ffMuc marker for 24 hours. THP1 killing was measured by the loss of luciferase activity from the tumor target. T cells expressing and HLAG1 specific Chimeric Antigen Receptor (HLA-G CAR) or a AML-targeting CD33-specific CAR (CD33 CAR) served as a positive control. NT=Not transduced.

FIG. 10: Alteration of the stalk and transmembrane domains of CIR retroviral constructs. A schematic table is presented indicating the derivatives of CIR4 that encodes the HLA-G binding domains D1 and D2 of ILT4 linked with the hinge/stalk and transmembrane domain of CD8α together with intracellular domains from 4-1 BB and CD3ζ. CIR constructs 6 through 10 encode the replacement of the stalk of human immunoglobulin IgG4, the CH3 domain of IgG4 or the stalk derived from CD28. These were fused with the transmembrane domain of CD8α or CD28 as depicted. Also see Tables 28B and 38-42.

Figure 11A:
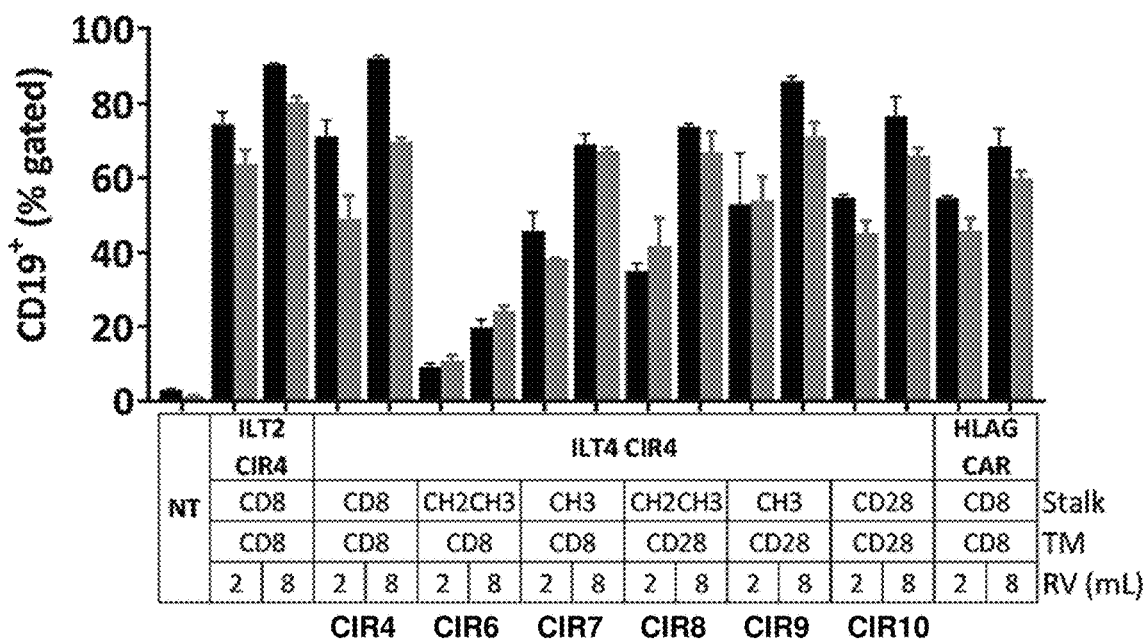
Figure 11B:
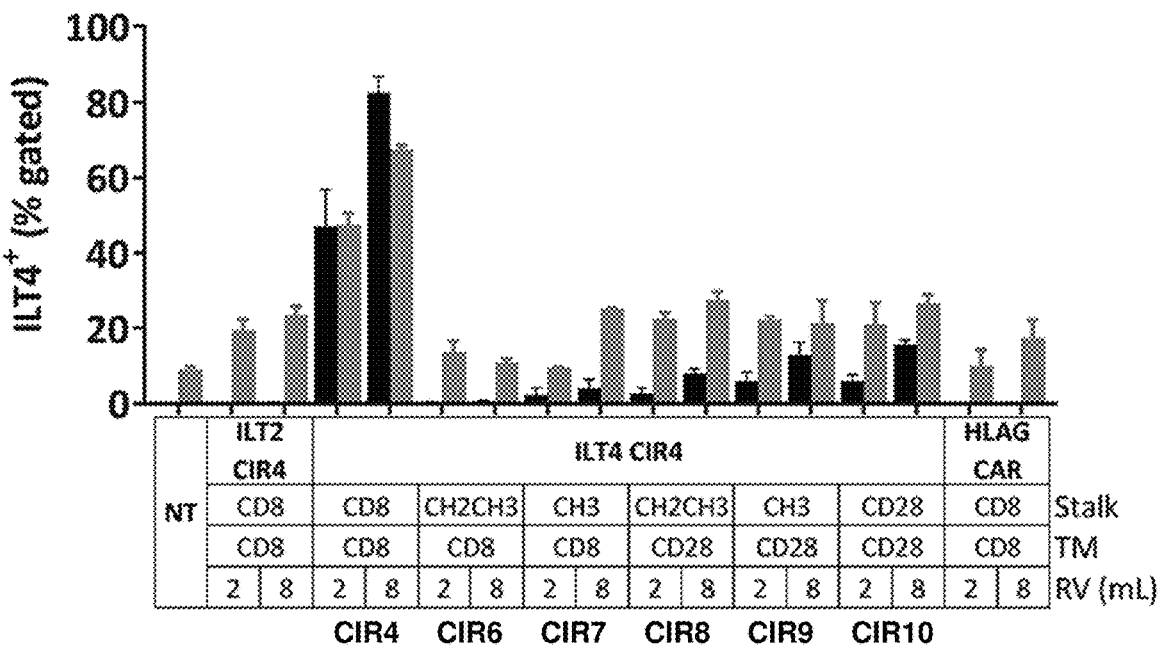
Figure 11C:
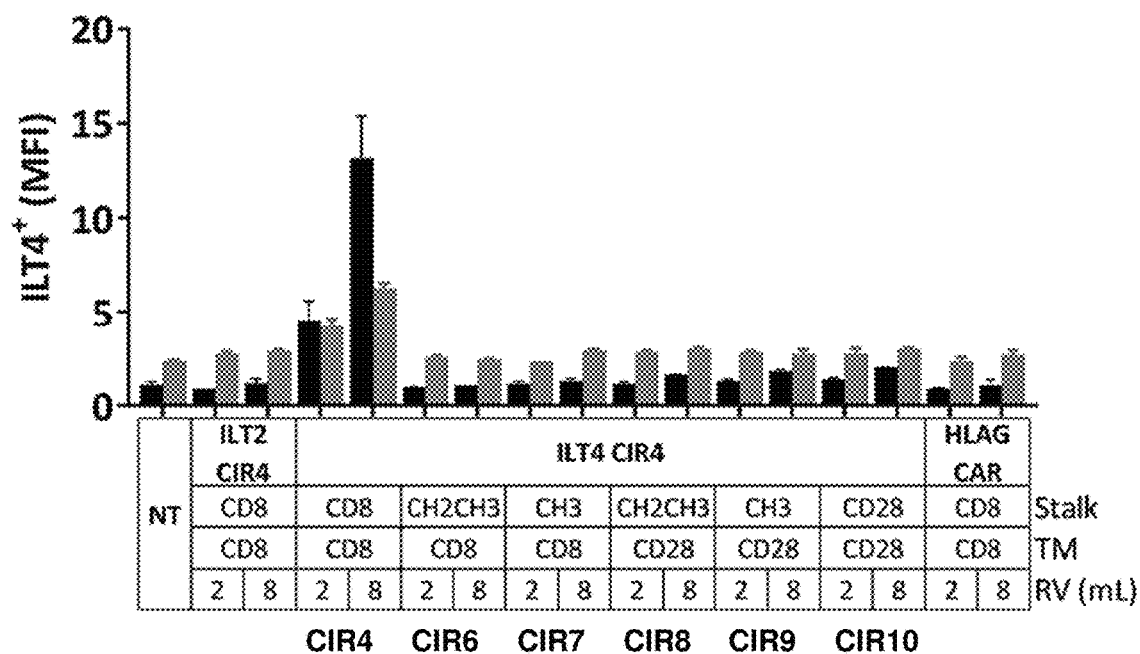

FIG. 11A-11C: Expression of γ-retroviral constructs encoding CIR proteins with derivative stalk and transmembrane domains. (FIG. 11A) Transduction efficiency at day 7 post-transduction (black) and day 14 (gray) of retroviral constructs encoding the indicated stalk and transmembrane derivatives marked by the ΔCD19 marker expressed by the same retroviral construct. (FIG. 11B) Expression of CIR constructs with alternative stalk and transmembrane domains determined by flow cytometry with an ILT4 antibody gated by a baseline of an isotype control. (FIG. 11C) Expression of CIR constructs with alternative stalk and transmembrane domains determined by the mean fluorescence intensity (MFI) of an ILT4-specific antibody by flow cytometry.

FIG. 12: Expression of HLA-G in human AML cell lines. Molm13-GFP and Molm14-GFP cells were stained with fluorescently labelled antibodies specific for HLA-G and subjected to flow cytometry. Gates were set by staining with labelled isotype control antibodies.

Figure 13A:
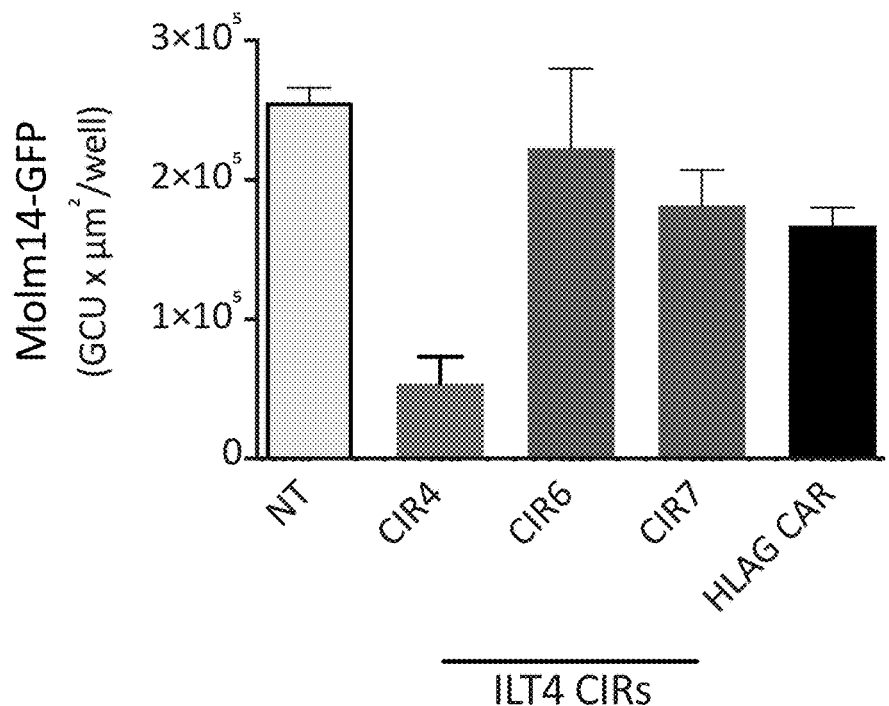
Figure 13B:
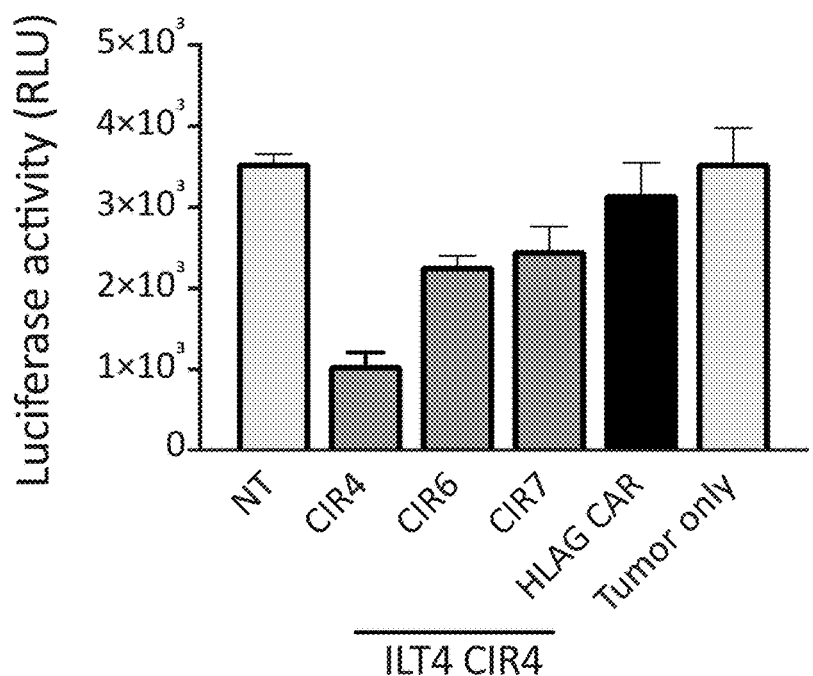

FIG. 13A-13B: Anti-tumor efficacy of CIR constructs against Molm-14 tumor targets. (FIG. 13A) HLA-G positive Molm14 cells stably transduced with GFPffluc were cocultured with non-transduced primary human T cells, CIR-T cells or HLA-G directed CAR-T cells at an effector to target ratio of 5:1 (N=2 donors). Molm14 outgrowth at 48 hours was determined by GFP-fluorescence in an Incucyte microscopic incubator. (FIG. 13B) Short term cytotoxicity of CIR-T cells against Molm14 tumor targets. Primary human T cells (N=2 donors) transduced with ILT4 CIR constructs or HLA-G CAR were cocultured with Molm14-GFPffluc cells for 24 hours. Molm14 killing was measured by the loss of luciferase activity from the tumor target.

Figure 14A:
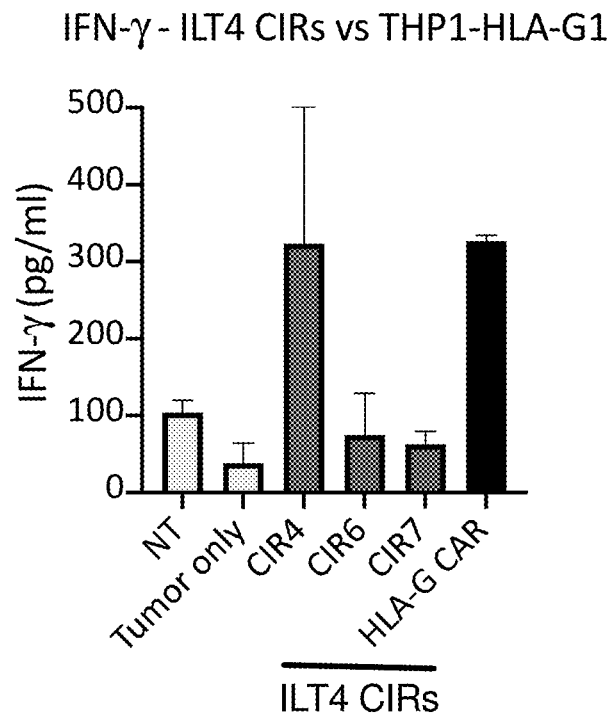
Figure 14B:
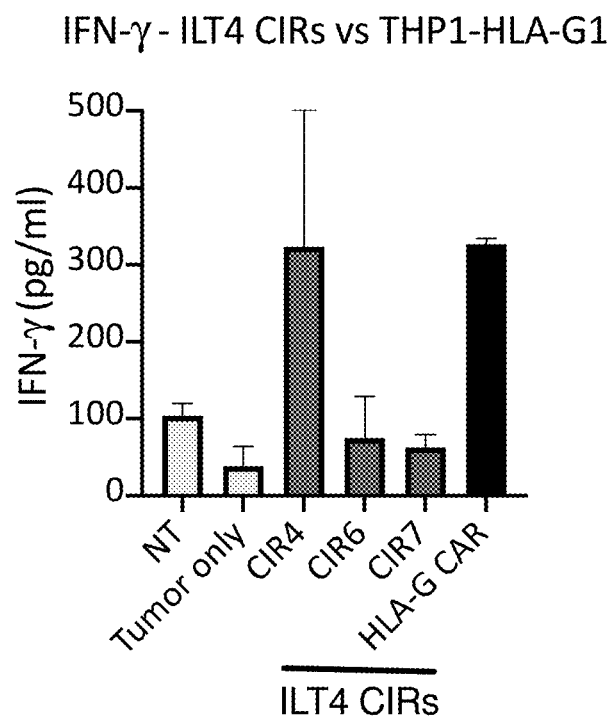

FIG. 14A-14B: Coculture of ILT4 CIR against THP1 cells expressing HLA-G isoforms. (FIG. 14A) Primary human T cells (NT), ILT4 CIR-T cells or HLA-G CAR-T cells were cultured with THP1 cells stably transduced with the HLA-G1 isoform. Activation of the T cells by engagement of the CIR or CAR was monitored by secretion of Interferon-γ (IFN-γ) into the culture media. (FIG. 14B) Interferon-γ secretion produced in cocultures of CIR-T and CAR-T cells with THP1 cells stably transduced to express HLA-G2.

IV. DETAILED DESCRIPTION

Provided are chimeric ILT receptors (CIRs) that include a targeting region from ILT2 or ILT4, a transmembrane domain, and an intracellular domain (ICD). The ICD includes a signaling region (e.g., CD3 zeta (CD3ζ)) and optionally a costimulatory region (e.g., CD28, 4-1 BB, OX40, and the like). Also provided are nucleic acids (e.g., expression vectors) encoding a subject CIR, and genetically modified cells (e.g., immune cells such as NK cells, T cells, iNKT cells, macrophages, and the like) expressing a subject CIR. For example, provided are genetically modified immune cells such as NK cells that include a nucleic acid encoding an ILT2 or ILT4 CIR. Also provided are methods of making genetically modified cells and methods of treatment (e.g., administering an immune cell, such as an NK cell, a T cell, or a macrophage, that expresses a subject CIR to an individual).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. As such, the articles "a" and "an" are used herein to refer to one or to more than one (i.e., to at least one) of the grammatical object of the article. By way of example, "an element" means one element or more than one element. Thus, for example, reference to "a cell" includes a plurality of such cells and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. For example, it is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

The entirety of each patent, patent application, publication and document referenced herein hereby is incorporated by reference. Citation of patents, patent applications, publications and documents are not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

1. MHC Class I ('MHC-I') Molecules

MHC-I molecules in humans include classical HLA-A, HLA-B or HLA-C a chains and non-classical HLA-E, HLA-F, HLA-G and HLA-H a chains. Classical MHC-I molecules display peptide fragments from within the cell to cytotoxic T cells. When non-self antigens are displayed in an MHC-I complex, cytotoxic T cells specific for the MHC:peptide complex can recognise and kill the MHC-I presenting cell. These cytotoxic signals also activate the growth potential of T cells in combination with costimulatory signaling.

MHC class I molecules are heterodimers that consist of two polypeptide chains, $\alpha$ and $\beta_2$-microglobulin $\beta 2$-M). The two chains are linked noncovalently via interaction of $\beta 2$-M and the $\alpha_3$ domain. The $\alpha$ chain (encoded by a HLA gene) is highly polymorphic, while the $\beta 2$-M subunit (encoded by the $\beta_2$-microglobulin gene) is not. The $\alpha_3$ domain is plasma membrane-spanning and interacts with the CD8+ co-receptor of a T cell. The $\alpha_3$-CD8 interaction holds the MHC-I molecule in place while the T cell receptor (TCR) on the surface of the cytotoxic T cell binds its $\alpha_1$-$\alpha_2$ heterodimer ligand, and checks the coupled peptide for antigenicity. The $\alpha_1$ and $\alpha_2$ domains fold to make an $\alpha$-helical groove for peptides to bind [Bjorkman et al, (1987) *Nature* 329:506].

While it is possible to match donor and recipients on the basis of their HLA subtype (e.g. A, B or C), the MHC-I:peptide complex displayed at the cell surface may still be recognised as non-self. For allogeneic T cell therapy it is beneficial to match classical HLA types to prevent allogeneic recognition of normal host tissues leading to Graft versus Host Disease (GvHD) and to improve the persistence of engrafted cells by mitigation of Host versus Graft (HvG) responses. However, allogeneic Natural Killer cell therapies against cancer benefit from classical HLA subtype mismatches particularly on HLA-C1, HLA-C2 and HLA-Bw4 containing alleles that can promote mismatching of KIR recognition by NK cells and augmentation of their innate cytotoxicity responses.

Non-classical MHC-I proteins (also called MHC Class Ib proteins) are also composed of a similar domain structure and generally are bound with $\beta 2$-M [Clements et al., (2005) *Proc Natl Acad Sci* 102:3360]. They also bind peptide fragments from the cell interior, but the diversity of bound peptides is limited and they do not present these peptides to the CD3-TCR complex to direct cytotoxicity. Instead these proteins engage inhibitory receptors expressed on a subset of immune cells to inhibit or attenuate immune cell function. HLA-E engages with the CD94/NKG2A complex on cytotoxic T cells and NK cells and HLA-G interacts with ILT proteins on a diverse group of immune effectors.

2. HLA-G

The non-classical MHC-I protein HLA-G is a major factor in the maintenance of immunological tolerance to maternal-fetal development [Kovats et al. *Science* (1990) 248:220, Ferreira et al, (2017) I 38:272]. Its normal expression is highest in the extravillous trophoblasts of the fetal placenta where it functions to block activation and infiltration of maternal immune cells of most types, but particularly T cells and NK cells from the fetus which has a haploidentical MHC haplotype. It is maintained at much lower levels in other immunoprivileged tissues including the cornea, a subset of mesenchymal stem cells [Chapel et al. (2006) *Blood* 108:4257, Selmani et al (2008) *Stem Cells* 26:212] and endocrine pancreas [Le Discorede et al. (2003) *Human Immunology* 64:1039, Cirulli et al. (2006) *Diabetes* 55:1214]. HLA-G is expressed in a diverse set of solid tumor types and leukemias [Reviewed in Lin and Yan (2018) *Front Imm.* 9:Art 2164] including melanoma [Paul et al, (1998) *Proc Natl Acad Sci* 95:4510], colorectal cancer, AML, ALL, renal cell carcinoma [Tronik-Le Roux et al, (2017) *Mol. Oncol.* 11:1561], breast cancer and lung cancer. Its function in cancer is to directly evade immune attack, but HLA-G is also expressed in tolerogenic DC-10 dendritic cells that inhibit lymphocytic responses by suppressive cytokine secretion and activate Treg cells and myeloid derived suppressor cells (MDSC) to create an immunosuppressive tumor microenvironment [Reviewed in Carosella et al, *Blood* (2011) 118:6499, Gao et al, (2018) BBA 1869:278]. HLA-G can thereby be considered an important checkpoint mediator of tumor promotion.

The HLA-G gene produces multiple mRNA transcripts that encode at least seven different protein products [Ishitani et al (1992) *Proc. Natl. Acad. Sci* 89:3947, (Seq ID Nos: 9, 15, 17, 19, 21). HLA-G1 contains the $\alpha 1$-$\alpha 2$-$\alpha 3$ domain structure with an alpha helical peptide binding cleft and a transmembrane domain and short intracellular carboxy terminal domain (see FIG. 1). This domain structure is canconical to MHC-I products. Other expressed splice products delete entire domains, for example HLA-G2 encodes $\alpha 1$, $\alpha 3$ and the transmembrane domain, deleting $\alpha 2$. HLA-G4 deletes the $\alpha 3$ domain and HLA-G3 encodes only the $\alpha 1$ domain. When expressed in M8 cells as transgenes, each of these forms of HLA-G was reported to exhibit immunosuppressive activity toward NK cell attack [Riteau et al (2001) *J. Immunology* 166:5018]. Secreted forms generated by alternative splicing include HLA-G5 and HLA-G6 which maintains the domain structure of HLA-G1 and G2 respectively but do not use the splice donor site for intron 4 and instead encode a short secreted peptide derived from intron 4. Similarly HLA-G7 uses a three amino acid peptide derived from intron 2. Further secreted forms of HLA-G1 are generated by cleavage at the transmembrane domain by matrix metalloproteinases to shed the cell surface of some HLA-G1 [Rizzo et al (2012) *Mol Cell Biochem* 381:243].

HLA-G exists in monomeric and oligomeric forms. Oligomers are chiefly dimers directed by disulphide linkages at Cys42 (in $\alpha 1$) or Cys 147 (in $\alpha 2$) [Gonen-Gross et al, (2005) *J. Imm.* 175:4866, Boyson et al, *Proc. Natl. Acad. Sci* 99:16180]. Evidence exists that the dimeric form of HLA-G is the principal immunosuppressive form and that it adopts a kinked quaternary structure relative to that of native monomers [Shiroishi et al (2006) *Proc Natl Acad Sci* 103: 10095, Clements et al (2005) *Proc Natl Acad Sci* 102:3360, Wang et al (2020) *Cel and Mol. Imm.* 17:966].

The different HLA-G forms together create a challenge for CAR-based therapy that relies on binding of an antibody-derived scFv or VhH domain as the targeting agent. Because different splice forms delete epitopes for given antibodies, a selection is placed by CAR therapy for expression only of epitopes that are not recognized by the CAR's binder while retaining immunosuppressive activity. Further, oligomerization can mask epitopes for an scFv due to structural change. As well, two of the commonly used antibody reagents for HLA-G 4H84 and 87G display crossreactivity to other HLA species that could lead to off-target, off-tumor targeting of CAR-T or CAR-NK cells [Attia et al (2021) *Int. J. Mol. Sci* 21:8678, Polakova et al (2004) *Hum. Imm.* 65:157, Swets et al (2018) *Clin. Imm* 194:80, Furukawa et al (2019) *Int J. Mol. Sci* 20:5947]

3. ILT2 and ILT4

HLA-G directs its immunosuppressive activity as a membrane bound ligand for inhibitory receptors Immunoglobulin-like transcript 2 (ILT2) and ILT4 (also called LIRB1 and LIRB2 or CD85j and CD85d respectively) on target immune cells [Colonna et al (1998) *J. Immunology* 160:3096 reviewed in Gao et al (2018) BBA 1869:278]. ILT2 (Seq ID NO: 29) is expressed in a subset of Natural Killer cells, iNKT cells, T cells, B cells and dendritic cells. ILT4 (Seq ID NO: 53) has a more broad expression pattern primarily in myeloid and stem cells including macrophage, myeloid derived suppressor cells (a population of less differentiated cells on the monocytic lineage), granulocytes including neutrophils, monocytes, hematopoietic stem cells and some neurons.

ILT2 has an extracellular domain structure consisting of four domains that have sequence and structural homology to Immunoglobulin domains (Ig domains) arranged in a column from membrane-distal D1 through to most membrane-proximal D4 followed by a transmembrane domain and an intracellular signaling domain that includes four iterated Immunoreceptor Tyrosine-based Inhibitory Motives (ITIMs). ILT4 has a similar extracellular and transmembrane architecture but only three ITIMs in its intracellular domain.

The D1 and D2 domains of ILT2 (see, e.g., Seq ID NO: 37 and 71) and ILT4 (see, e.g., Seq ID NO: 57 and 75) govern interaction with HLA-G and can be separated from the D3 and D4 domains [Donadi et al (2011) *Cell. Mol. Life Sci.* 68:369, Morales (2007) 122:179, HoWanYin et al (2012) *Cell. Mol. Life Sci.* 69:4041, Shiroishi et al (2006) *Proc Natl Acad Sci* 103:10095, Wang et al (2020) *Cel and Mol. Imm.* 17:966]. Unlike activating interactions made by the CD3 complex with classical MHC-I and inhibitory and activating interactions made by KIR proteins of NK cells ILT2 and ILT4 do not bind with the α1-α2 domains that contain the peptide binding cleft, but instead interact with the membrane proximal α3 domain and with β2-microglobulin (see FIG. 11B). ILT2 makes extensive contact with β2-M and relatively few contacts with α3 of HLA-G and requires β2-M association with HLA-G to maintain even a low affinity interaction. Conversely, ILT4 makes extensive contact with α3 and can maintain interaction with all known actively immunosuppressive forms of HLA-G, possibly excluding HLA-G3/G7 that contains only the α1 domain.

ILT2 and ILT4 can interact with other MHC-I and MHCI-like proteins, notably HLA-A2, HLA-B, HLA-C, and HLA-F, CD1d and UL18. With the exception of UL18, a decoy MHC-I from cytomegalovirus [Wilcox et al (2002) *BMC Struct. Biol* 2:6], these are low affinity interactions with dissociation constants ($K_D$) between 2 µM and 40 µM. Relevance for immunosuppressive signalling has not been demonstrated with affinities this weak. Similarly, interaction between ILT2 and ILT4 with monomeric forms of HLA-G are weak, in the µM range. However, dimeric HLA-G forms display high affinity (2-4 nM) interaction with ILT2 and ILT4 possibly due to display of further contact sites or, alternatively, due to an avidity effect reducing the off rate for ILT dissociation [Shiroishi et al, (2006) *J. Biol. Chem* 281: 10440, Gao et al (2020) *Cell Mol Imm* 17:966]. The dimeric forms of HLA-G are therefore most likely to be bioactive [Gonen-Gross et al, (2005) *J. Imm.* 175:4866] and functional for immunosuppression in a tumor setting and further, are most likely to be relevant as a targeted molecule for cell-based immunotherapy by chimeric receptors.

ILT4 is a receptor for non-MHC ligands including Angiopoietin-like proteins 2 and 5 [Zheng et al (2012) *Nature* 485:656, Deng et al (2014) *Blood* 124:924] Regulation by soluble ANGPTL2 and ANGPTL5 is thought to provide a protective signal from bone marrow stroma for self-renewal and survival of ILT4-expressing hematopoietic stem cells. Interaction between ILT4 and ANGLPs is directed by the D1 domain in concert with the D4 domain of ILT4 and specific residues in either the D1 or D4 are essential to maintain high affinity interaction. Notably, mutation of tyrosine 96 to alanine reduced ANGPTL2/5 binding but did not reduce HLA-G1 interaction with full-length ILT4 [Deng et al (2014) *Blood* 124:924].

ILT4 interacts with moderate affinity to inhibitory Nogo receptor ligands derived from myelin [Atwal et al (2008) *Science* 322:967, Matsushita et al, (2014) *J. Biol. Chem* 286:25739]. The mouse ortholog of ILT proteins, PIRB, is also found in subsets of neurons and may regulate axonal outgrowth by interaction with myelin-based MAG, Nogo and OMgp [US patent 20100047232] and Sema4a [Lu et al. (2018) *Nat. Comm.* 7:742]. High affinity interactions were characterized in the mouse ortholog for ILT4, PIRB and did not map to the HLA-G binding D1 and D2 domains, but rather to the membrane proximal domains of PIRB [Matsushita et al, (2014) *J. Biol. Chem* 286:25739].

4. Chimeric Antigen Receptors

Chimeric antigen receptors (or CARs) are artificial receptors designed to convey antigen specificity to cells. They generally include an antigen-specific component, a transmembrane component, and an intracellular component selected to activate the cell. CAR-expressing cells may be used in various therapies, including cancer therapies.

A CAR is, for example, a chimeric polypeptide which comprises a polypeptide sequence that recognizes a target antigen (an antigen-recognition domain) linked to a transmembrane polypeptide and an intracellular domain polypeptide selected to activate the cell, and thereby provide specific immunity. The antigen-recognition domain may be a single-chain variable fragment (scFv), or may, for example, be derived from other molecules such as, for example, a T cell receptor or camelid VhH domain. The intracellular domain comprises at least one polypeptide which causes activation of the cell (a "signaling region"), such as, for example, but not limited to, CD3 zeta (CD3ζ) (see, e.g., SEQ ID NO: 33), and, optionally, costimulatory molecules (a "costimulatory region") (for example, but not limited to, CD28 (see, e.g., SEQ ID NO: 49), OX40, and 4-1 BB (see, e.g., SEQ ID NO: 35)).

Thus, in typical examples of CAR usage, cells are modified to express a CAR that comprises a single chain antibody variable fragment (scFv) fused with a transmembrane domain containing a linker region and an intracellular domain derived from the CD3 zeta component (see, e.g., SEQ ID NO: 33). In natural T cells and NK cells, signals from CD3 zeta drive the initial activation of the T cell through signaling to the NF-ATc transcription factor. These signals drive targeted cell killing in cytotoxic T lymphocytes and synergize with costimulatory signaling pathways to drive the robust cell proliferation of T cell immune response. The genetically modified cells may be modified by transduction or transfection with a nucleic acid that expresses the CAR and a nucleic acid (the same or different) that comprises a polynucleotide that encodes a chimeric signaling polypeptide (see below). In other embodiments, a CAR is expressed without also expressing a chimeric signaling polypeptide.

Chimeric antigen receptors can be expressed in NK cells, iNKT cells or in macrophages to generate antigen specific cytotoxicity.

CARs include chimeric receptors that are derived from antibodies, but also include chimeric T cell receptors. These chimeric T cell receptors may comprise a polypeptide sequence that recognizes a target antigen, where the recognition sequence may be, for example, but not limited to, the recognition sequence derived from a T cell receptor or a scFv. The intracellular domain polypeptides are those that act to activate the T cell. Chimeric T cell receptors are discussed in, for example, Gross & Eshar *FASEB Journal* (1992) 6:3370-3378, and Zhang et al., (2010) *PLOS Pathogens* 6:1-13.

5. Chimeric Receptors Targeted by ILT Proteins (i.e., a "Chimeirc ILT Receptor" or "CIR")

Redirection of the cytotoxic specificity of T or NK cells can be controlled by engagement of an antigen-scFv (or TCR) interaction, but can also be controlled by a receptor-ligand pairing such that the receptor for the targeted ligand can be formed into a chimeric protein that can maintain a high affinity interaction with the cell while capably maintaining signal transduction to activate the immune cell (we use T cells and NK cells as an example hereafter). Essential to the use of such receptors as binding agents for CAR-like proteins is high affinity interaction with the target protein (<50 nM) to permit stable adhesion of the immune cell with the target and stable signalling to activate the T or NK cell. Further, in highly preferred embodiments the receptor or portions of the receptor used to engage the target are specific for the target alone to prevent off-tumor targeting. Third, similar to scFv and similar binders, it is essential that high level expression of the target protein or ligand be maintained on target tissue (for example, a tumor) relative to normal tissues.

(i) Targeting Region

The extracellular domains (D1-D4) of ILT2 (see, e.g., SEQ ID NO: 31, which includes D1-D4 plus the transmembrane region of ILT2) can be engineered to target HLA-G expressing tumor cells and generate activating signal transduction in immune cells expressing a chimeric version of ILT2 that replaces the naturally inhibitory ITIM-containing ILT2 intracellular domain (ICD) with signalling components that drive activating signals (for example the ICD of CD3ζ and 4-11BB).

Similarly, the extracellular domains (D1-D4) of ILT4 (see, e.g., SEQ ID NO: 55, which includes D1-D4 plus the transmembrane region of ILT4) can be engineered to generate activating signals in immune cells by replacement of the ILT4 ICD with activation signalling moieties (for example the ICD of CD3ζ and 4-1 BB). Using the D1-D4 extracellular domain of ILT2 or ILT4 for the targeting region would create an ILT2 D1-D4 chimeric receptor (i.e., ILT2 D1-D4 CIR) or an ILT4 D1-D4 chimeric receptor (i.e., ILT4 D1-D4 CIR) (see FIG. 4A). Thus, in some cases, the targeting region of a subject chimeric ILT receptor (CIR) includes an ILT2 or ILT4 D1-D4 domain (which therefore targets HLA-G).

ILT4 maintains more contacts with 03 on the HLA heavy chain and can interact with free heavy chain forms of HLA-G while ILT2 D1/D2 requires contact with β2-M and α3 to maintain interaction with HLA-G (FIG. 4B).

Because ILT2 and ILT4 maintain high affinity ($K_D$ low nM) interactions with dimeric HLA-G and low affinity ($K_D$ is μM for interaction with other MHC-I proteins including monomeric HLA-G and CD1d), specificity for tumors carrying high levels of HLA-G increases proportionately the amount of HLA-G in dimeric form and permits selection of tumor tissue over normal tissue expressing high levels of classical MHC-I, but little or no HLA-G. Mutation of HLA-G1 at positions Cys42 to Ser or Cys147 to Ser blocks HLA-G1 dimerization and severely reduces targeting by ILT2 or ILT4 CIR-T cells or CIR-NK cells.

It is appreciated by the inventors that HLA-G exists in several different isoforms. CARs which include an antibody-based targeting region (such as an scFv), would only be able to target HLA-G isoforms that include the epitope targeted by the antigen binding region (e.g., scFv). This could place a selection for tumor cells expressing HLA-G isoforms that lack the targeted epitope—thus allowing the cancer to evade treatment. To the contrary, a subject ILT2 or ILT4 based chimeric receptor protein (which targets HLA-G) should target many more, and perhaps all, HLA-G isoforms because ILT2 and ILT4 naturally bind those isoforms.

Construction of an ILT2 D1/D2 CIR and an ILT4 D1/D2 CIR

The D1 and D2 domains are sufficient to direct binding of ILT2 and ILT4 to HLA-G while the D3 and D4 domains are likely to serve as a scaffold to display D1 and D2 to HLA-G [Shiroishi et al, (2006) *J. Biol. Chem* April 14; 281(15): 10439-47]. In some embodiments, the D3 and D4 domains can be deleted from an ILT2 CIR or and ILT4 CIR and maintain functional interactions through the D1-D2 domains from ILT2 (see, e.g., Seq ID NO: 71) or ILT4 (see, e.g., Seq ID NO: 75) with HLA-G forms (see FIG. 4A). Thus, in some cases, the targeting region of a subject ILT2 or ILT4 chimeric receptor will include the D1-D2 domains of ILT2 or ILT4 (see, e.g., SEQ ID NO: 71 for D1-D2 of ILT2 and SEQ ID NO: 75 for D1-D2 of ILT4), and in some such cases the targeting region will not include (i.e., will lack) the D3-D4 domains.

In some embodiments, the targeting region (the region including the D1-D2 domains) of a subject ILT2 chimeric receptor includes an amino acid sequence that has 80% or more sequence identity (e.g., 85% or more, 90% or more, 95% or more, 96% or more, 97% or more, 98% or more, 99% or more, or 100%) with the ILT2 sequence set forth in any one of SEQ ID Nos: 37, 70, 71, and 72, which sequences are as follows:

```
                                              (SEQ ID NO: 37)
MHLPKPTLWAEPGSVITQGSPVTLRCQGGQETQEYRLYREKKTAPWITRI

PQELVKKGQFPIPSITWEHTGRYRCYYGSDTAGRSESSDPLELVVTGAYI

KPTLSAQPSPVVNSGGNVTLQCDSQVAFDGFILCKEGEDEHPQCLNSQPH

ARGSSRAIFSVGPVSPSRRWWYRCYAYDSNSPYEWSLPSDLLELLVLG (SEQ ID NO: 70)
MHLPKPTLWAEPGSVITQGSPVTLRCQGGQETQEYRLYREKKTALWITRI

PQELVKKGQFPIPSITWEHAGRYRCYYGSDTAGRSESSDPLELVVTGAYI

KPTLSAQPSPVVNSGGNVILQCDSQVAFDGFSLCKEGEDEHPQCLNSQPH

ARGSSRAIFSVGPVSPSRRWWYRCYAYDSNSPYEWSLPSDLLELLVLG
```

(SEQ ID NO: 71)
PKPTLWAEPGSVITQGSPVTLRCQGGQETQEYRLYREKKTAPWITRIPQE

LVKKGQFPIPSITWEHTGRYRCYYGSDTAGRSESSDPLELVVTGAYIKPT

LSAQPSPVVNSGGNVTLQCDSQVAFDGFILCKEGEDEHPQCLNSQPHARG

SSRAIFSVGPVSPSRRWWYRCYAYDSNSPYEWSLPSDLLELLVLG (SEQ ID NO: 72)
PKPTLWAEPGSVITQGSPVTLRCQGGQETQEYRLYREKKTALWITRIPQE

LVKKGQFPIPSITWEHAGRYRCYYGSDTAGRSESSDPLELVVTGAYIKPT

LSAQPSPVVNSGGNVILQCDSQVAFDGFSLCKEGEDEHPQCLNSQPHARG

SSRAIFSVGPVSPSRRWWYRCYAYDSNSPYEWSLPSDLLELLVLG

In some cases, the targeting region includes an amino acid sequence that has 90% or more sequence identity (e.g., 95% or more, 96% or more, 97% or more, 98% or more, 99% or more, or 100%) with the sequence set forth in any one of SEQ ID Nos: 37, 70, 71, and 72. In some cases, the targeting region includes an amino acid sequence that has 95% or more sequence identity (e.g., 96% or more, 97% or more, 98% or more, 99% or more, or 100%) with the sequence set forth in any one of SEQ ID Nos: 37, 70, 71, and 72. In some cases, the targeting region includes the amino acid sequence set forth in any one of SEQ ID Nos: 37, 70, 71, and 72.

In some cases, the targeting region (the region including the D1-D2 domains) of an ILT2 chimeric receptor includes an amino acid sequence that has 80% or more sequence identity (e.g., 85% or more, 90% or more, 95% or more, 96% or more, 97% or more, 98% or more, 99% or more, or 100%) with the sequence set forth as SEQ ID No: 37. In some cases, the targeting region includes an amino acid sequence that has 90% or more sequence identity (e.g., 95% or more, 96% or more, 97% or more, 98% or more, 99% or more, or 100%) with the sequence set forth as SEQ ID No: 37. In some cases, the targeting region includes an amino acid sequence that has 95% or more sequence identity (e.g., 96% or more, 97% or more, 98% or more, 99% or more, or 100%) with the sequence set forth as SEQ ID No: 37. In some cases, the targeting region includes the amino acid sequence set forth as SEQ ID No: 37.

In some embodiments, the targeting region (the region including the D1-D2 domains) of a subject ILT4 chimeric receptor includes an amino acid sequence that has 80% or more sequence identity (e.g., 85% or more, 90% or more, 95% or more, 96% or more, 97% or more, 98% or more, 99% or more, or 100%) with the ILT4 sequence set forth in any one of SEQ ID Nos: 57, 74, and 75, which sequences are as follows:

(SEQ ID NO: 57)
MTPIVTVLICLGLSLGPRTHVQTGTIPKPTLWAEPDSVITQGSPVTLSCQ

GSLEAQEYRLYREKKSASWITRIRPELVKNGQFHIPSITWEHTGRYGCQY

YSRARWSELSDPLVLVMTGAYPKPTLSAQPSPVVTSGGRVTLQCESQVAF

GGFILCKEGEDEHPQCLNSQPHARGSSRAIFSVGPVSPNRRWSHRCYGYD

LNSPYVWSSPSDLLELLVPG (SEQ ID NO: 74)
MTPIVTVLICLGLSLGPRTRVQTGTIPKPTLWAEPDSVITQGSPVTLSCQ

GSLEAQEYRLYREKKSASWITRIRPELVKNGQFHIPSITWEHTGRYGCQY

YSRARWSELSDPLVLVMTGAYPKPTLSAQPSPVVTSGGRVTLQCESQVAF

GGFILCKEGEDEHPQCLNSQPHARGSSRAIFSVGPVSPNRRWSHRCYGYD

LNSPYVWSSPSDLLELLVPG (SEQ ID NO: 75)
PKPTLWAEPDSVITQGSPVTLSCQGSLEAQEYRLYREKKSASWITRIRPE

LVKNGQFHIPSITWEHTGRYGCQYYSRARWSELSDPLVLVMTGAYPKPTL

SAQPSPVVTSGGRVTLQCESQVAFGGFILCKEGEDEHPQCLNSQPHARGS

SRAIFSVGPVSPNRRWSHRCYGYDLNSPYVWSSPSDLLELLVPG

In some cases, the targeting region includes an amino acid sequence that has 90% or more sequence identity (e.g., 95% or more, 96% or more, 97% or more, 98% or more, 99% or more, or 100%) with the sequence set forth in any one of SEQ ID Nos: 57, 74, and 75. In some cases, the targeting region includes an amino acid sequence that has 95% or more sequence identity (e.g., 96% or more, 97% or more, 98% or more, 99% or more, or 100%) with the sequence set forth in any one of SEQ ID Nos: 57, 74, and 75. In some cases, the targeting region includes the amino acid sequence set forth in any one of SEQ ID Nos: 57, 74, and 75.

In some cases, the targeting region (the region including the D1-D2 domains) of an ILT4 chimeric receptor includes an amino acid sequence that has 80% or more sequence identity (e.g., 85% or more, 90% or more, 95% or more, 96% or more, 97% or more, 98% or more, 99% or more, or 100%) with the sequence set forth as SEQ ID No: 57. In some cases, the targeting region includes an amino acid sequence that has 90% or more sequence identity (e.g., 95% or more, 96% or more, 97% or more, 98% or more, 99% or more, or 100%) with the sequence set forth as SEQ ID No: 57. In some cases, the targeting region includes an amino acid sequence that has 95% or more sequence identity (e.g., 96% or more, 97% or more, 98% or more, 99% or more, or 100%) with the sequence set forth as SEQ ID No: 57. In some cases, the targeting region includes the amino acid sequence set forth as SEQ ID No: 57.

For any of the above embodiments discussed in this section, in some cases the subject ILT2 or ILT4 chimeric receptor lacks a D3 and D4 domain (i.e., lacks a region corresponding to the D3-D4 domains of ILT2 (SEQ ID NO: 73) or ILT4 (SEQ ID NO: 76), respectively). For ILT2, the region with the D3-D4 domains is:

(SEQ ID NO: 73)
PLDILIAGQFYDRVSLSVQPGPTVASGENVTLLCQSQGWMQTFLLTKEGA

ADDPWRLRSTYQSQKYQAEFPMGPVTSAHAGTYRCYGSQSSKPYLLT.

For ILT4, the region with the D3-D4 domains is:

(SEQ ID NO: 76)
QPGPVMAPGESLTLQCVSDVGYDRFVLYKEGERDLRQLPGRQPQAGLSQA

NFTLGPVSRSYGGQYRCYGAHNLSSECSAPSDPLDILITGQIRGTPFISV

QPGPTVASGENVTLLCQSWRQFHTFLLTKAGAADAPLRLRSIHEYPKYQA

EFPMSPVTSAHAGTYRCYGSLNSDPYLLSHPSEPLEL.

In some cases, a subject CIR lacks an amino acid sequence having 85% or more (e.g., 90% or more, 95% or more, 98% or more, 99% or more, or 100%) sequence identity with the sequence set forth as SEQ ID NO: 73. In some cases, a subject CIR lacks an amino acid sequence having 85% or more (e.g., 90% or more, 95% or more, 98% or more, 99% or more, or 100%) sequence identity with the sequence set forth as SEQ ID NO: 76. In some cases, a subject CIR lacks an amino acid sequence having 85% or more (e.g., 90% or more, 95% or more, 98% or more, 99% or more, or 100%) sequence identity with the sequence set forth in any one of SEQ ID NOs: 73 and 76.

In some embodiments a linker may be fused as a chimera with D1-D2 domains from ILT2 or ILT4 to the plasma membrane and serves as a stalk that replaces D3 and D4 domains. In these embodiments, deletion of D3-D4 may prevent interaction of a CIR with proteins other than HLA-G that interact with native ILT2 or ILT4 through the D3 or D4 domains, for examples the interactions of ANGPTL2 and ANGPTL5 with ILT4 D4 and the interaction of nogo, Omgp and MAG with ILT4 D3-D4. Prevention of such interactions may reduce potentially toxic mistargeting of a CIR-expressing cell with non-tumor tissue such as bone marrow stroma, myelin and endothelium.

Stalk Domains

In the embodiment described above, replacement of D3-D4 can be made with any protein or portion of a protein that properly displays the ILT2 or ILT4 D1-D2 binder in a context for HLA-G expressed on a separate cell. In certain embodiments a short polypeptide linker may form the linkage between the transmembrane domain and the intracellular domain of the chimeric ILT receptor. Thus, the chimeric ILT receptors may further comprise a stalk, that is, an extracellular region of amino acids between the extracellular domain and the transmembrane domain. The purpose of the stalk domain is to extend the D1/D2 domains away from the plasma membrane and toward the target protein HLA-G. For example, the stalk may be a sequence of amino acids naturally associated with a selected transmembrane domain. In some embodiments, the chimeric ILT receptor comprises a CD8 transmembrane domain, in certain embodiments, the chimeric ILT receptor comprises a CD8 transmembrane domain together with additional amino acids on the extracellular portion of the transmembrane domain. In certain embodiments, the CAR comprises a CD8 transmembrane domain and a CD8 stalk. In a specific embodiment, a CD8 transmembrane domain comprises (or consists of) a sequence disclosed herein (see Tables 4-42). In another specific embodiment, a CD8 stalk comprises (or consists of) a sequence disclosed herein (see Tables 4-42). The chimeric ILT receptor may further comprise a region of amino acids between the transmembrane domain and the cytoplasmic domain, which are naturally associated with the polypeptide from which the transmembrane domain is derived.

Following transduction, cells now express the CIR on their surface, and upon contact and ligation with HLA-G, signal through the CD3 zeta chain inducing cytotoxicity and cellular activation. It is important that such a domain not have affinity for other proteins thereby causing potential mistargeting of a CIR-expressing immune cell. Examples of such chimeric stalk moieties include, but are not limited to membrane proximal portions of CD8α (see, e.g., SEQ ID NOs: 43 and 107), the CH2/CH3 domains of IgG (e.g., IgG1, IgG4) (see, e.g., SEQ ID NOs: 51 and 98), the CH3 domain of IgG (e.g., IgG1, IgG4)(see, e.g., SEQ ID NO: 102), HER2, mGluR2, CD28 (see, e.g., SEQ ID NOs: 47 and 106) and CTLA4 (see FIG. 5A).

For example, in some cases the stalk domain of a subject CIR is selected from: an ILT2, ILT4, CD28, CH2/CH3, CH3, and CD8 stalk domain. See, for example:

(SEQ ID NO: 39)
VVSGPSGGPSSPTTGPTSTSGPEDQPLTPTGSDPQSGLGRHLGVVIGILV

AVILLLLLLLLLFLILRHRRQ, which includes an ILT2 stalk and TM domain;

(SEQ ID NO: 107)
PAPRPPTPAPTIASQPLSLRPEACRPAAGGAVHTRGLDFACD, which includes a CD8 stalk domain;

(SEQ ID NO: 43)
PAPRPPTPAPTIASQPLSLRPEACRPAAGGAVHTRGLDFACDIYIWAPLA

GTCGVLLLSLVITLYCNHRNRRRVCKCPR, which includes a CD8 stalk and TM domain;

(SEQ ID NO: 106)
IEVMYPPPYLDNEKSNGTIIHVKGKHLCPSPLFPGPSKP, which includes a CD28 stalk;

(SEQ ID NO: 47)
IEVMYPPPYLDNEKSNGTIIHVKGKHLCPSPLFPGPSKPFWVLVVVGGV

LACYSLLVTVAFIIFWV, which includes a CD28 stalk and TM domain;

(SEQ ID NO: 98)
VDKRVESKYGPPCPSCPAPPVAGPSVFLFPPKPKDTLMISRTPEVTCVV

VDVSQEDPEVQFNWYVDGVEVHNAKTKPREEQFQSTYRVVSVLTVLHQD

WLNGKEYKCKVSNKGLPSSIEKTISKAKGQPREPQVYTLPPSQEEMTKN

QVSLTCLVKGFYPSDIAVEWESNGQPENNYKTTPPVLDSDGSFFLYSRL

TVDKSRWQEGNVFSCSVMHEALHNHYTQKSLSLSLEL, which includes a CH2CH3 stalk;

(SEQ ID NO: 102)
VDKRVESKYGPPCPGQPREPQVYTLPPSQEEMTKNQVSLTCLVKGFYPS

DIAVEWESNGQPENNYKTTPPVLDSDGSFFLYSRLTVDKSRWQEGNVFS

CSVMHEALHNHYTQKSLSLSLEL, which includes a CH3 stalk;

(SEQ ID NO: 51)
DPAEPKSPDKTHTCPPCPAPELLGGPSVFLFPPKPKDTLMISRTPEVTC

VVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYS

KLTVDKSRWQQGNVFSCSVMHEALHNHYTQKSLSLSPGKKDPFWVLVVV

GGVLACYSLLVTVAFIIFWV, which includes a CH2CH3 stalk and CD28 TM domain;

(SEQ ID NO: 59)
VVSGPSMGSSPPPTGPISTPAGPEDQPLTPTGSDPQSGLGRHLGVVIGI
LVAVVLLLLLLLLLFLILRHRRQ, which includes an ILT4 stalk and TM domain.

In some embodiments, the stalk of domain of a subject CIR includes an amino acid sequence having 80% or more sequence identity (e.g., 85% or more, 90% or more, 95% or more, 96% or more, 97% or more, 98% or more, 99% or more, or 100%) with the stalk sequence portion of the amino acid sequence set forth in any one of SEQ ID NOs: 39, 43, 47, 51, and 59. In some embodiments, the stalk of domain of a subject CIR includes an amino acid sequence having 95% or more sequence identity (e.g., 96% or more, 97% or more, 98% or more, 99% or more, or 100%) with the stalk sequence portion of the amino acid sequence set forth in any one of SEQ ID NOs: 39, 43, 47, 51, and 59. In some embodiments, the stalk of domain of a subject CIR includes the stalk sequence portion of the amino acid sequence set forth in any one of SEQ ID NOs: 39, 43, 47, 51, and 59.

In some embodiments, the stalk of domain of a subject CIR includes an amino acid sequence having 80% or more sequence identity (e.g., 85% or more, 90% or more, 95% or more, 96% or more, 97% or more, 98% or more, 99% or more, or 100%) with the stalk sequence set forth in any one of SEQ ID NOs: 98, 102, 106, and 107. In some embodiments, the stalk of domain of a subject CIR includes an amino acid sequence having 95% or more sequence identity (e.g., 96% or more, 97% or more, 98% or more, 99% or more, or 100%) with the stalk sequence set forth in any one of SEQ ID NOs: 98, 102, 106, and 107. In some embodiments, the stalk of domain of a subject CIR includes the stalk sequence set forth in any one of SEQ ID NOs: 98, 102, 106, and 107.

Interaction of the D1/D2 stalk-containing CIR with dimeric HLA-G will have the effect of dimerizing the intracellular signalling domains that in certain embodiments can stimulated ICD activation and cell signalling (FIG. 5B).

Mutant Forms of an ILT2 D1/D2 CIR or an ILT4 D1/D2 CIR

In further embodiments mutations may be made within the ILT2 or ILT 4 D1 or D2 domains contained within a CIR to increase the specificity of the CIR toward HLA-G over other potentially interacting proteins. For example, a mutation may be made to encode an amino acid other than tyrosine at the correlating position of native amino acid 96 (Y96) of ILT4 SEQ ID NO: 57) or ILT2 (SEQ ID NO: 31) (e.g., Y96A). The effect of such a mutant form is to reduce potential interaction with ANGPTL2 and ANGPTL5 while retaining binding affinity for HLA-G. In yet another further embodiment a similar mutation may be placed in a full-length ILT4 CIR containing D1-D4 domains together with a mutation in domain D4 (at a position corresponding to tyrosine394 (Y394) of SEQ ID NO: 55) that further destabilizes interaction with ANGPTL2 and ANGPTL5 (for example Y394A mutation, see SEQ ID NO: 61). The corresponding position of ILT2 is tyrosine395 (Y395) of SEQ ID NO: 31.

As such, in some cases, a subject ILT4 CIR includes a mutation at an amino acid position corresponding to Y96 of SEQ ID NO: 57 (e.g., Y96A). In some cases, a subject ILT2 CIR includes a mutation at an amino acid position corresponding to Y96 of SEQ ID NO: 31 (e.g., Y96A). In some cases, a subject ILT4 CIR includes a mutation at an amino acid position corresponding to Y394 of SEQ ID NO: 55 (e.g., Y394A). In some cases, a subject ILT2 CIR includes a mutation at an amino acid position corresponding to Y395 of SEQ ID NO: 31 (e.g., Y395A). In some cases, a subject ILT4 CIR includes a mutation at an amino acid position corresponding to Y96 of SEQ ID NO: 55 (e.g., Y96A) and a mutation at an amino acid position corresponding to Y394 of SEQ ID NO: 55 (e.g., Y394A) (e.g., Y96A/Y394A). In some cases, a subject ILT2 CIR includes a mutation at an amino acid position corresponding to Y96 of SEQ ID NO: 31 (e.g., Y96A) and a mutation at an amino acid position corresponding to Y395 of SEQ ID NO: 31 (e.g., Y395A) (e.g., Y96A/Y395A).

Other embodiments along similar lines may limit interaction with classical HLA proteins or CD1 while retaining binding for HLA-G. These mutations may replace interacting sites with α3 domains that are specific to the heavy chains of these HLAs or on a surface bound to β2-M.

(ii) Transmembrane (TM) Region

A CIR may include a single-pass or multiple-pass transmembrane sequence (e.g., at the N-terminus or C-terminus of the chimeric protein, or within the protein, e.g., connecting the extracellular targeting region to the intracellular domain). Single pass transmembrane regions are found in certain CD molecules, tyrosine kinase receptors, serine/threonine kinase receptors, TGFβ, BMP, activin and phosphatases. Single pass transmembrane regions often include a signal peptide region and a transmembrane region of about 20 to about 25 amino acids, many of which are hydrophobic amino acids and can form an alpha helix. A short track of positively charged amino acids often follows the transmembrane span to anchor the protein in the membrane. Multiple pass proteins include ion pumps, ion channels, and transporters, and include two or more helices that span the membrane multiple times. All or substantially all of a multiple pass protein sometimes is incorporated in a chimeric protein. Sequences for single pass and multiple pass transmembrane regions are known and can be selected for incorporation into a chimeric protein molecule.

In some embodiments, the transmembrane domain is fused to the extracellular domain of the CIR. In some embodiments, the transmembrane domain is fused to the extracellular region and the intracellular region, thereby connecting the extracellular and intracellular regions to one another. In one embodiment, the transmembrane domain that naturally is associated with one of the domains in the CIR is used. In other embodiments, a transmembrane domain that is not naturally associated with one of the domains in the CIR is used. In some instances, the transmembrane domain can be selected or modified by amino acid substitution (e.g., typically changed to a hydrophobic residue) to avoid binding of such domains to the transmembrane domains of the same or different surface membrane proteins to minimize interactions with other members of the receptor complex.

Transmembrane (TM) domains may, for example, be derived from the alpha, beta, or zeta chain of the T cell receptor, CD3-ε, CD3ζ, CD4, CD5, CD8, CD8α, CD9, CD16, CD22, CD28, CD33, CD38, CD64, CD80, CD86, CD134, CD137, ILT2, HER2, ILT4 or CD154—or transmembrane regions containing functional variants thereof such as those retaining a substantial portion of the structural, e.g., transmembrane, properties thereof can be used. See e.g., Kahlon et al. (2004) Cancer Res. 64:9160-9166; Schambach et al. (2009) Methods Mol. Biol. 506: 191-205; Jensen et al. (1998) Biol. Blood Marrow Transplant 4:75-83; Patel et al. (1999) Gene Ther. 6:412; Song et al. (2012) Blood 119:696-706; Carpenito et al. (2009) Proc. Natl.

Acad. Sci. USA 106:3360-5; Hombach et al. (2012) Oncoimmunology 1:458-66) and Geiger et al. (2001) Blood 98:2364-71.

Or, in some examples, the transmembrane domain may be synthesized de novo, comprising mostly hydrophobic residues, such as, for example, leucine, isoleucine, phenylalanine and valine. Suitable CD8 stalk sequences, transmembrane sequences, and CD3ζ sequences for use with the invention are disclosed in Tables 4-42.

For example, in some cases the TM domain of a subject CIR is selected from: an ILT2 (see, e.g., SEQ ID NO: 39), ILT4 (see, e.g., SEQ ID NO: 59), CD28 (see, e.g., SEQ ID NOs: 47 and 104), and CD8 (see, e.g., SEQ ID NOs: 43 and 100) TM domain. See, for example:

```
                                            (SEQ ID NO: 39)
VVSGPSGGPSSPTTGPTSTSGPEDQPLTPTGSDPQSGLGRHLGVVIGIL
VAVILLLLLLLLLFLILRHRRQ,
``` which includes an ILT2 stalk and TM domain;

```
                                           (SEQ ID NO: 100)
       IYIWAPLAGTCGVLLLSLVITLYCNHRNRRRVCKCPR,
``` which includes a CD8 TM domain;

```
                                            (SEQ ID NO: 43)
PAPRPPTPAPTIASQPLSLRPEACRPAAGGAVHTRGLDFACDIYIWAPL
AGTCGVLLLSLVITLYCNHRNRRRVCKCPR,
``` which includes a CD8 stalk and TM domain;

```
                                           (SEQ ID NO: 104)
            FWVLVVVGGVLACYSLLVTVAFIIFWV,
``` which includes a CD28 TM domain;

```
                                            (SEQ ID NO: 47)
IEVMYPPPYLDNEKSNGTIIHVKGKHLCPSPLFPGPSKPFWVLVVVGGV
LACYSLLVTVAFIIFWV,
``` which includes a CD28 stalk and TM domain;

```
                                            (SEQ ID NO: 51)
DPAEPKSPDKTHTCPPCPAPELLGGPSVFLFPPKPKDTLMISRTPEVTC

VVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYS

KLTVDKSRWQQGNVFSCSVMHEALHNHYTQKSLSLSPGKKDPFWVLVVV

GGVLACYSLLVTVAFIIFWV,
``` which includes a CH2CH3 stalk and CD28 TM domain; and

```
                                            (SEQ ID NO: 59)
VVSGPSMGSSPPPTGPISTPAGPEDQPLTPTGSDPQSGLGRHLGVVIGI
LVAVVLLLLLLLLLFLILRHRRQ,
``` which includes an ILT4 stalk and TM domain.

In some embodiments, the TM domain of a subject CIR includes an amino acid sequence having 80% or more sequence identity (e.g., 85% or more, 90% or more, 95% or more, 96% or more, 97% or more, 98% or more, 99% or more, or 100%) with the TM domain sequence portion of the amino acid sequence set forth in any one of SEQ ID NOs: 39, 43, 47, 51, and 59. In some embodiments, the TM domain of a subject CIR includes an amino acid sequence having 95% or more sequence identity (e.g., 96% or more, 97% or more, 98% or more, 99% or more, or 100%) with the TM domain sequence portion of the amino acid sequence set forth in any one of SEQ ID NOs: 39, 43, 47, 51, and 59. In some embodiments, the TM domain of a subject CIR includes the TM domain sequence portion of the amino acid sequence set forth in any one of SEQ ID NOs: 39, 43, 47, 51, and 59.

In some embodiments, the stalk domain plus the TM domain (stalk/TM domain) of a subject CIR includes an amino acid sequence having 80% or more sequence identity (e.g., 85% or more, 90% or more, 95% or more, 96% or more, 97% or more, 98% or more, 99% or more, or 100%) with the amino acid sequence set forth in any one of SEQ ID NOs: 39, 43, 47, 51, and 59. In some embodiments, the stalk domain plus the TM domain (stalk/TM domain) of a subject CIR includes an amino acid sequence having 95% or more sequence identity (e.g., 96% or more, 97% or more, 98% or more, 99% or more, or 100%) with the amino acid sequence set forth in any one of SEQ ID NOs: 39, 43, 47, 51, and 59. In some embodiments, the stalk domain plus the TM domain (stalk/TM domain) of a subject CIR includes an amino acid sequence having the amino acid sequence set forth in any one of SEQ ID NOs: 39, 43, 47, 51, and 59.

In some embodiments, the TM domain of a subject CIR includes an amino acid sequence having 80% or more sequence identity (e.g., 85% or more, 90% or more, 95% or more, 96% or more, 97% or more, 98% or more, 99% or more, or 100%) with the TM domain sequence set forth in any one of SEQ ID NOs: 100 and 104. In some embodiments, the TM domain of a subject CIR includes an amino acid sequence having 95% or more sequence identity (e.g., 96% or more, 97% or more, 98% or more, 99% or more, or 100%) with the TM domain sequence set forth in any one of SEQ ID NOs: 100 and 104. In some embodiments, the TM domain of a subject CIR includes the TM domain sequence set forth in any one of SEQ ID NOs: 100 and 104.

(iii) Intracellular Domain (ICD)

As noted above, a subject chimeric ILT receptor (ILT2 or ILT4 based) includes an intracellular region (Intracellular domain or ICD) that replaces the natural intracellular portion of ILT2 or ILT4, which is inhibitory, with an ICD of a CAR, which is activating. As such, the ICD of a subject CIR (ILT2 version or ILT4 version) includes a "signaling region", which has at least one signaling domain that causes activation of the cell, and can optionally include a "costimulatory region", which can include one or more costimulatory domains.

Signaling Region

The "signaling region" (or "intracellular signaling domain") of a CIR refers to the part of a CIR that participates in transducing the signal from CIR binding to a target molecule (HLA-G in the case of a subject CIR) into the interior of the immune effector cell to elicit effector cell function, e.g., activation, cytokine production, proliferation and/or cytotoxic activity, including the release of cytotoxic factors to the CIR-bound target cell, or other cellular responses elicited with target molecule binding to the extracellular CIR domain. Accordingly, the term "signaling region" ("intracellular signaling domain") refers to the portion of a protein which transduces the effector function signal and that directs the cell to perform a specialized function. To the extent that a truncated portion of an intracellular signaling domain is used, such truncated portion may be used in place of a full-length intracellular signaling domain as long as it transduces the effector function signal. The term signaling region is meant to include any truncated portion of an intracellular signaling domain sufficient for transducing effector function signal. In some cases, the signaling region includes signaling motifs which are known as immunoreceptor tyrosine-based activation motifs (or "ITAMs").

Examples of intracellular domain sequences that can be used in a signaling region of a subject CIR include those derived from an intracellular signaling domain of a lymphocyte receptor chain, a TCR/CD3 complex protein, an Fc receptor subunit, an IL-2 receptor subunit, CD3ζ, FcRγ, FcRβ, CD3γ, CD3δ, CD3ε, CD5, CD22, CD79a, CD79b, CD66d, CD278(ICOS), FcsRI, DAP10, and DAP12.

In some embodiments, the signaling region of a subject CIR includes a CD3 zeta (CD3ζ) signaling domain (see, e.g., SEQ ID NO: 33). Thus, in some cases, the ICD of a subject chimeric ILT receptor (ILT2-version or ILT4-version) includes a signaling region that includes an amino acid sequence having 80% or more sequence identity (e.g., 85% or more, 90% or more, 95% or more, 96% or more, 97% or more, 98% or more, 99% or more, or 100%) with SEQ ID NO: 33. In some embodiments, the signaling region includes an amino acid sequence having 90% or more sequence identity (e.g., 95% or more, 96% or more, 97% or more, 98% or more, 99% or more, or 100%) with SEQ ID NO: 33. In some embodiments, the signaling region includes an amino acid sequence having 95% or more sequence identity (e.g., 96% or more, 97% or more, 98% or more, 99% or more, or 100%) with SEQ ID NO: 33. In some embodiments, the signaling region includes the amino acid sequence set forth as SEQ ID NO: 33.

In some embodiments, the signaling region of a subject CIR includes a DAP10 signaling domain. In some embodiments, the signaling region of a subject CIR includes a DAP12 signaling domain.

Costimulatory Region

In some embodiments, the ICD of a subject CIR also includes a costimulatory region. The costimulatory region includes at least one costimulatory domain (e.g., one, two, three, one or more, two or more, or three or more costimulatory domains). Examples of costimulatory domains include, but are not limited to: CD40, CD27, CD28, 4-11BB, HVEM, TRANCE, RANK, OX40, DAP10, and ICOS costimulatory domains. Examples of costimulatory domains include, but are not limited to: 4-11BB, OX40, ICOS, CD28, CD27, MyD88, IL-1 Rα, HVEM, TRANCE, IL-1 Rβ, CD70, IL-18Rα, CD40, IL-18Rβ, IL-33Rα, CD30, and IL-33Rβ. Examples of costimulatory domains include, but are not limited to: 4-1BB, OX40, ICOS, RANK, DAP10, DAP12, CD28, CD27, MyD88, IL-1 Rα, HVEM, TRANCE, IL-1 Rβ, CD70, IL-18Rα, CD40, IL-18Rβ, IL-33Rα, CD30, and IL-33Rβ. In some cases, the costimulatory region includes one or more (e.g., one, two, three, one or more, or two or more) costimulatory domains selected from the group consisting of: CD28 (see, e.g., SEQ ID NO: 49), 4-1 BB (see, e.g., SEQ ID NO: 35), and OX40—or any combination thereof. In some cases, a CD28 costimulatory domain is used. In some cases, a 4-1 BB costimulatory domain is used. In some cases, both a CD28 costimulatory domain and a 4-1 BB costimulatory domain is used (i.e., they are both used). In some cases, a CD28 costimulatory domain and an OX40 costimulatory domain is used.

In some cases, the costimulatory region includes a truncated MyD88 polypeptide fused with signaling domains of receptor mediators of costimulation, such as, for example, CD40, CD27, CD28, 4-1BB, HVEM, TRANCE, RANK, OX40, or ICOS. In some cases, the costimulatory region includes a MyD88 polypeptide or a truncated MyD88 polypeptide and a costimulatory domain selected from the group consisting of CD27, ICOS, RANK, TRANCE, CD28, 4-11BB, OX40, and DAP10.

In some embodiments, the ICD of a subject chimeric ILT receptor (ILT2-version or ILT4-version) includes a costimulatory region that includes an amino acid sequence having 80% or more sequence identity (e.g., 85% or more, 90% or more, 95% or more, 96% or more, 97% or more, 98% or more, 99% or more, or 100%) with SEQ ID NO: 49. In some embodiments, the signaling region includes an amino acid sequence having 90% or more sequence identity (e.g., 95% or more, 96% or more, 97% or more, 98% or more, 99% or more, or 100%) with SEQ ID NO: 49. In some embodiments, the signaling region includes an amino acid sequence having 95% or more sequence identity (e.g., 96% or more, 97% or more, 98% or more, 99% or more, or 100%) with SEQ ID NO: 49. In some embodiments, the signaling region includes the amino acid sequence set forth as SEQ ID NO: 49.

In some embodiments, the ICD of a subject chimeric ILT receptor (ILT2-version or ILT4-version) includes a costimulatory region that includes an amino acid sequence having 80% or more sequence identity (e.g., 85% or more, 90% or more, 95% or more, 96% or more, 97% or more, 98% or more, 99% or more, or 100%) with SEQ ID NO: 35. In some embodiments, the signaling region includes an amino acid sequence having 90% or more sequence identity (e.g., 95% or more, 96% or more, 97% or more, 98% or more, 99% or more, or 100%) with SEQ ID NO: 35. In some embodiments, the signaling region includes an amino acid sequence having 95% or more sequence identity (e.g., 96% or more, 97% or more, 98% or more, 99% or more, or 100%) with SEQ ID NO: 35. In some embodiments, the signaling region includes the amino acid sequence set forth as SEQ ID NO: 35.

In some embodiments, the ICD of a subject chimeric ILT receptor (ILT2-version or ILT4-version) includes a costimulatory region that includes an amino acid sequence having 80% or more sequence identity (e.g., 85% or more, 90% or more, 95% or more, 96% or more, 97% or more, 98% or more, 99% or more, or 100%) with SEQ ID NO: 35 and an amino acid sequence having 80% or more sequence identity (e.g., 85% or more, 90% or more, 95% or more, 96% or more, 97% or more, 98% or more, 99% or more, or 100%) with SEQ ID NO: 49. In some embodiments, the signaling region includes an amino acid sequence having 90% or more sequence identity (e.g., 95% or more, 96% or more, 97% or more, 98% or more, 99% or more, or 100%) with SEQ ID NO: 35 and. an amino acid sequence having 90% or more sequence identity (e.g., 95% or more, 96% or more, 97% or more, 98% or more, 99% or more, or 100%) with SEQ ID NO: 49. In some embodiments, the signaling region includes an amino acid sequence having 95% or more sequence identity (e.g., 96% or more, 97% or more, 98% or more, 99% or more, or 100%) with SEQ ID NO: 35 and an amino acid sequence having 95% or more sequence identity (e.g., 96% or more, 97% or more, 98% or more, 99% or more, or 100%) with SEQ ID NO: 49. In some embodiments, the signaling region includes the amino acid sequence set forth as SEQ ID NO: 35 and the amino acid sequence set forth as SEQ ID NO: 49.

In some embodiments, the signaling region of a subject CIR includes a CD3 zeta (CD3ζ) signaling domain and the costimulatory region includes a CD28 costimulatory domain. In some embodiments, the signaling region of a subject CIR includes a CD3 zeta (CD3ζ) signaling domain and the costimulatory region includes a 4-1 BB costimulatory domain. In some embodiments, the signaling region of a subject CIR includes a CD3 zeta (CD3ζ) signaling domain and the costimulatory region includes a 4-1 BB costimulatory domain and a CD28 costimulatory domain. In some embodiments, the signaling region of a subject CIR includes a CD3 zeta (CD3ζ) signaling domain and the costimulatory region includes a CD28 costimulatory domain and an OX40 costimulatory domain.

Non-limiting examples of a 4-1 BB, CD28, and OX40 costimulatory signaling domains can be found in U.S. 20130266551, U.S. Pat. No. 5,686,281; Geiger, T. L. et al., Blood 98: 2364-2371 (2001); Hombach A. et al., J Immunol 167: 6123-6131 (2001); Maher J. et al. Nat Biotechnol 20: 70-75 (2002); Haynes N. M. et al., J Immunol 169: 5780-5786 (2002); Haynes N. M. et al., Blood 100: 3155-3163 (2002); and in U.S. 2012/20148552, all of which are incorporated by reference herein for their teachings related to costimulatory domains.

Non-limiting examples of chimeric polypeptides useful for inducing cell activation, and related methods for inducing therapeutic cell activation including, for example, expression constructs, methods for constructing vectors, and assays for activity or function, may also be found in the following patents and patent applications: US2014-0286987-A1; WO2014/151960; US2016/0046700; WO2015/123527; US2004/0209836; U.S. Pat. No. 7,404,950; WO2004/073641; US2011/0033388; U.S. Pat. No. 8,691,210; WO2008/049113; US2014/0087468; U.S. Pat. No. 9,315,559; WO2010/033949; US2011/0287038; WO2011/130566; US2016/0175359; WO2016/036746; WO2016/100241; US2017/0166877; WO2017/106185; and WO2018/208849—each of which is incorporated by reference herein in its entirety, including all text, tables and drawings, for all purposes, including for purposes related to describing cell activation domains (e.g., cell signaling and costimulatory domains).

Example CIRs

The different regions/domains of a subject CIR are modular and can be mixed and matched as is convenient. FIG. 6A and FIG. 10 provide examples of various forms a subject CIR can take—and those depicted in the Figures were produced and tested in various assays throughout the examples section. For example, FIG. 6A introduces formats CIR1, CIR2, CIR3, and CIR4 while FIG. 10 introduces formats CIR6, CIR7, CIR8, CIR9, and CIR10. FIG. 10 only depicts these formats for ILT4, but one of ordinary skill in the art would understand that the same formats can be used to produce ILT2 CIRs if desired.

In some cases, a subject CIR will be an ILT2 CIR4 or an ILT4 CIR4 (i.e., an ILT2 or ILT4 D1-D2 targeting domain, a CD8 stalk and TM, a CD3-zeta (CD3ζ) signaling domain, and a 4-1 BB costimulatory domain (a T2A-delta-CD19 region is optional, i.e., in some cases will be absent). See, e.g., FIG. 6A.

In some cases, a subject CIR will be an ILT2 CIR3 or an ILT4 CIR3 (i.e., an ILT2 or ILT4 D1-D4 targeting domain, a CD8 stalk and TM, a CD3-zeta (CD3ζ) signaling domain, and a 4-1 BB costimulatory domain (a T2A-delta-CD19 region is optional, i.e., in some cases will be absent). See, e.g., FIG. 6A.

In some cases, a subject CIR will be an ILT2 CIR2 or an ILT4 CIR2 (i.e., an ILT2 or ILT4 D1-D2 targeting domain, an ILT2 or ILT4 stalk and TM, a CD3-zeta (CD3ζ) signaling domain, and a 4-1 BB costimulatory domain (a T2A-delta-CD19 region is optional, i.e., in some cases will be absent). See, e.g., FIG. 6A.

In some cases, a subject CIR will be an ILT2 CIR1 or an ILT4 CIR1 (i.e., an ILT2 or ILT4 D1-D4 targeting domain, an ILT2 or ILT4 stalk and TM, a CD3-zeta (CD3ζ) signaling domain, and a 4-1 BB costimulatory domain (a T2A-delta-CD19 region is optional, i.e., in some cases will be absent). See, e.g., FIG. 6A.

CIR Variations

Included in the scope of the invention are functional portions of the inventive CIRs described herein. The term "functional portion" when used in reference to a CIR refers to any part or fragment of the CIR of the invention, which part or fragment retains the biological activity of the CIR of which it is a part (the parent CIR). Functional portions encompass, for example, those parts of a CIR that retain the ability to recognize the target (HLA-G) or target cells, or detect, treat, or prevent a disease, to a similar extent, the same extent, or to a higher extent, as the parent CIR. In reference to the parent CIR, the functional portion can comprise, for instance, about 10%, 25%, 30%, 50%, 68%, 80%, 90%, 95%, or more, of the parent CIR.

The functional portion can comprise additional amino acids at the amino or carboxy terminus of the portion, or at both termini, which additional amino acids are not found in the amino acid sequence of the parent CIR. Desirably, the additional amino acids do not interfere with the biological function, e.g., recognize target cells, detect cancer, treat or prevent cancer, etc. More desirably, the additional amino acids enhance the biological activity, as compared to the biological activity of the parent CIR.

Included in the scope of the invention are functional variants or biological equivalent of the inventive CIRs disclosed herein. A functional variant can, for example, comprise the amino acid sequence of the parent polypeptide with at least one conservative amino acid substitution. Alternatively or additionally, the functional variants can comprise the amino acid sequence of the parent polypeptide with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent polypeptide.

Such biological variant (including functional portions thereof) can comprise synthetic amino acids in place of one or more naturally-occurring amino acids.

Such biological variant (including functional portions thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

Such biological variant (including functional portions thereof) can be obtained by methods known in the art. The polypeptides may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001 and U.S. Pat. No. 5,449,752. Also, polypeptides and proteins can be recombinantly produced using the nucleic acids described herein using standard recombinant methods. See, for instance, Sambrook et al, Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994.

6. Costimulatory Polypeptides

Genetically modified cells that express a subject chimeric ILT receptor (CIR) may further express a costimulatory polypeptide (e.g. in addition to expressing a CIR). Expression of the costimulatory polypeptide may be inducible or constitutive.

The costimulatory polypeptide may comprise one or more costimulatory signaling regions such as CD27, ICOS, RANK, IL-18R, DAP12, HVEM, TRANCE, CD28, 4-1BB, IL-1R, OX40, DAP10, IL-33R, MyD88, or CD40 or, for example, the cytoplasmic regions thereof. The costimulatory polypeptide may comprise one or more suitable costimulatory signaling regions that activate the signaling pathways activated by CD27, ICOS, RANK, IL-18R, DAP-12, HVEM, TRANCE, CD28, 4-1BB, IL-1R, OX40, DAP10, IL-33R, MyD88, or CD40. Costimulating polypeptides include any molecule or polypeptide that activates the NF-κB pathway, MyD88 pathway, STAT5 pathway, STAT1 pathway, Akt pathway, and/or p38 pathway of tumor necrosis factor receptor (TNFR) family (i.e., CD40, RANK/TRANCE-R, OX40, 4-1 BB) and CD28 family members (CD28, ICOS). More than one costimulating polypeptide or costimulating polypeptide cytoplasmic region may be expressed in the modified cells.

Suitable CD28, OX40, 4-1 BB and ICOS sequences for use with the invention are disclosed in Tables 4d-36.

Cells may include chimeric signaling polypeptides, including, for example, chimeric signaling polypeptides where a truncated MyD88 polypeptide has also been fused with signaling domains of receptor mediators of costimulation, such as, for example, CD40, CD27, CD28, 4-1BB, OX40, or ICOS.

7. Safety Switches

Genetically modified cells that express a subject chimeric ILT receptor (CIR) may also express a safety switch, also known as an inducible suicide gene or suicide switch, which can be used to eradicate the therapeutic cells in vivo if desired e.g. if GvHD develops. In some examples, therapeutic cells may trigger an adverse event, such as off-target toxicity due to a CIR, or a patient might experience a negative symptom during therapy using modified cells, or there may be side effects due to non-specific attacks on healthy tissue; or, sometimes, the therapeutic cells may no longer be needed, or the therapy is intended for a specified amount of time, for example, the therapeutic cells may work to decrease the tumor cell, or tumor size, and may no longer be needed. Thus it can be useful if genetically modified cells can also inducibly express a polypeptide which causes the cells to die, such as an inducible caspase-9 polypeptide. If there is a need, for example, to reduce the number of therapeutic cells, the switch can be triggered.

These switches respond to a trigger, such as a pharmacological agent, which is supplied when it is desired to eradicate the therapeutic cells, and which leads to cell death (e.g. by triggering necrosis or apoptosis). These agents can lead to de novo expression of a toxic gene product, but a more rapid response can be obtained if the genetically modified cells already express a protein which is switched into a toxic form in response to the agent.

In some embodiments, a safety switch is based on a pro-apoptotic protein that can be triggered by administering a trigger molecule (also referred to as a ligand inducer) to a subject. If the pro-apoptotic protein is fused to a polypeptide sequence which binds to the trigger molecule, delivery of this trigger molecule can bring two pro-apoptotic proteins into proximity such that they trigger apoptosis. For instance, caspase-9 can be fused to a modified human FK-binding protein which can be induced to dimerize in response to the pharmacological agent rimiducid (AP1903). The use of a safety switch based on a human pro-apoptotic protein, such as, for example, caspase-9 minimizes the risk that cells expressing the switch will be recognized as foreign by a human subject's immune system. Delivery of rimiducid to a subject can therefore trigger apoptosis of cells which express the caspase-9 switch.

Further non-limiting examples of chimeric polypeptides useful for inducing cell death or apoptosis may be found in the following patents and patent applications, each of which is incorporated by reference herein in its entirety for all purposes. U.S. Patent Application US2011/0286980; U.S. Pat. No. 9,089,520; U.S. Patent Application US2014/0255360; U.S. Pat. No. 9,434,935; WO2014/16438; US2016/0151465; WO2014/197638; US2015/0328292; WO2015/134877; US2016/0166613; WO2016/100236; US2016/0175359; WO2016/100241; US2017/0166877; WO2017/106185; each of which is incorporated by reference herein in its entirety, including all text, tables and drawings, for all purposes. Details about some specific switches and approaches are also given below:

Inducible Caspase 9 (iC9): This proapoptotic switch includes a fusion of caspase-9 with FKBP12 or derivatives. It is latent in the absence of ligand but drives dimerization of the initiator caspase, caspase-9, from the intrinsic pathway for cell apoptosis. Dimerization leads to caspase-9 activation, cleavage and activation of the effector caspase, caspase-3, and rapid cell death by apoptosis. Inducible caspase-9 has particular utility as a safety switch in cell therapies to block toxic responses.

Caspase-9 switches: Examples are described in Di Stasi et al. (2011) *supra*; see also Yagyu et al. (2015) *Mol Ther* 23(9):1475-85; Rossigloni et al. (2018) *Cancer Gene Ther* doi.org/10.1038/s41417-018-0034-1; Jones et al. (2014) *Front Pharmacol* doi.org/10.3389/fphar.2014.00254; U.S. Pat. Nos. 9,434,935; 9,913,882; 9,393,292; and patent application US2015/0328292.

The safety switch may comprise a modified Caspase-9 polypeptide having modified activity, such as, for example, reduced basal activity in the absence of the homodimerizer ligand. Modified Caspase-9 polypeptides are discussed in, for example, U.S. Pat. No. 9,913,882 and US2015/0328292, supra, and may include, for example, amino acid substitutions at position 330 (e.g., D330E or D330A) or, for example, amino acid substitutions at position 450 (e.g., N405Q), or combinations thereof, including, for example, D330E-N405Q and D330A-N405Q. Caspase-9 polypeptide with lower basal activity have been described previously, e.g. in U.S. Pat. Nos. 9,434,935, 9,932,572 and 9,913,882, and U.S. Patent Application Nos. 62/668,223, 62/756,442, 62/816,799, Ser. Nos. 15/901,556, 15/888,948.

In some embodiments the safety switch may be, for example, iCasp9 discussed in Di Stasi et al. (2011) supra, which consists of the sequence of the human FK506-binding protein (FKBP12) (GenBank AH002 818) with an F36V mutation, connected through a SGGGS (SEQ ID NO: 108) linker to a modified human caspase 9 (CASP9) which lacks its endogenous caspase activation and recruitment domain.

The F36V mutation increases the binding affinity of FKBP12 to synthetic homodimerizers AP20187 and rimiducid.

FKBP12-allele specific binding by rimiducid: Rimiducid binds with high affinity (~0.1 nM) to the valine-36 allele of FKBP12 but with low affinity (~500 nM) to the wild-type phenylalanine-36 FKBP12 allele. Rapamycin and rapalogs can bind to either FKBP allele. Rimiducid has two identical, protein-binding surfaces arranged tail-to-tail, each with high affinity and specificity for the valine-36 form (known variously as FKBP12(F36V), FKBP12v36, FKBPV, $F_{V36}$, or simply $F_v$). See Jemal et al., *CA Cancer J. Clinic.* 58, 71-96 (2008); Scher & Kelly *Journal of Clinical Oncology* 11, 1566-72 (1993)). Two tandem copies of the protein may also be used in the construct so that higher-order oligomers are induced upon cross-linking by rimiducid. Attachment of one or more $F_V$ domains onto one or more cell signaling molecules that normally rely on homodimerization can convert that protein to a rimiducid-controlled switch. FKBP12 variants may also be used. Variants may bind to rapamycin, or rapalogs, but with less affinity to rimiducid than, for example, FKBP12v36. Examples of FKBP12 variants include those from many species, including, for example, yeast. In one embodiment, the FKBP12 variant is FKBP12.6 (calstablin).

The suicide switch may be controlled by a pharmaceutical composition comprising a trigger molecule (such as a dimerizing or multimerizing ligand). An effective amount of a pharmaceutical composition comprising the trigger molecule is an amount that achieves the desired result of killing the genetically-modified cells. The degree of killing may be high (e.g. over 60%, 70%, 80%, 85%, 90%, 95%, or 97%) or complete; conversely, sometimes only partial removal will be desired (e.g. under 80%, 70%, 60%, 50%, 40%, 30%, 20%, or 10% of the genetically modified cells are killed). Thus genetically-modified may display a range of sensitivities to a trigger molecule. The trigger molecule may thus be used to eradicate only a portion of the cells (e.g. at least 10%) while permitting some of the cells (e.g. at least 10%) to survive. The concentration of the trigger molecule can be selected according to the desired balance of cell death and survival e.g. a higher concentration will be delivered if a higher proportion of cell eradication (or complete eradication) is desired.

These concentrations can be determined by simple dose-ranging experiments, monitoring levels of cell death in response to the trigger molecule. Any appropriate assay may be used to determine the percent of genetically modified cells that are killed. An assay may include the steps of obtaining a first sample from a subject before administration of the trigger molecule and obtaining a second sample from the subject after administration of the trigger molecule and comparing the number or concentration of therapeutic cells in the first and second samples to determine the percent of therapeutic cells that are killed. One can empirically determine the effective amount of a particular composition presented herein without undue experimentation.

Cells may include chimeric signaling polypeptides, including, for example, chimeric signaling polypeptides where a truncated MyD88 polypeptide has also been fused with signaling domains of receptor mediators of costimulation, such as, for example, CD40, CD27, CD28, 4-1BB, HVEM, TRANCE, RANK, OX40, or ICOS.

In some embodiments, a chimeric signaling polypeptide comprises cytoplasmic signaling regions from two costimulatory polypeptides, such as, for example, 4-1BB and CD28, or one, or two or more costimulatory polypeptide cytoplasmic signaling regions selected from the group consisting of CD27, ICOS, RANK, TRANCE, CD28, 4-11BB, OX40, DAP10. In some embodiments, the chimeric signaling polypeptide comprises a MyD88 polypeptide or a truncated MyD88 polypeptide and a costimulatory polypeptide cytoplasmic signaling region selected from the group consisting of CD27, ICOS, RANK, TRANCE, CD28, 4-1BB, OX40, and DAP10.

As noted above, non-limiting examples of chimeric polypeptides useful for inducing cell activation, and related methods for inducing therapeutic cell activation including, for example, expression constructs, methods for constructing vectors, and assays for activity or function, may also be found in the following patents and patent applications, each of which is incorporated by reference herein in its entirety for all purposes: US2014-0286987-A1; WO2014/151960; US2016/0046700; WO2015/123527; US2004/0209836; U.S. Pat. No. 7,404,950; WO2004/073641; US2011/0033388; U.S. Pat. No. 8,691,210; WO2008/049113; US2014/0087468; U.S. Pat. No. 9,315,559; WO2010/033949; US2011/0287038; WO2011/130566; US2016/0175359; WO2016/036746; WO2016/100241; US2017/0166877; WO2017/106185; and WO2018/208849—each of which is incorporated by reference herein in its entirety, including all text, tables and drawings, for all purposes.

In some embodiments, cells are designed to provide constitutively active therapy. In some embodiments, genetically modified cells comprise a nucleic acid comprising a first polynucleotide encoding a Chimeric ILT2 or ILT4 Receptor (or CIR), and a second polynucleotide encoding a chimeric signaling polypeptide. In some embodiments, the second polynucleotide is positioned 5' of the first polynucleotide. In some embodiments, the second polynucleotide is positioned 3' of the first polynucleotide. In some embodiments, a third polynucleotide encoding a linker polypeptide is positioned between the first and second polynucleotides. Where the third polynucleotide is positioned 3' of the first polynucleotide and 5' of the second polynucleotide, the linker polypeptide, may remain intact following translation, or may separate the polypeptides encoded by the first and second polynucleotides during, or after translation. In some embodiments, the linker polypeptide is a 2A polypeptide (see elsewhere herein), which may separate the polypeptides encoded by the first and second polynucleotides during, or after translation. High level costimulation is provided constitutively through an alternate mechanism in which a leaky 2A cotranslational sequence (see elsewhere herein). is used to separate the CIR from the chimeric signaling polypeptide. Where the 2A separation is incomplete, for example from a leaky 2A sequence, most of the expressed chimeric signaling polypeptide molecules are separated from the chimeric antigen receptor polypeptide and may remain cytosolic, and some portion or the chimeric signaling polypeptide molecules remain attached, or linked, to the CIR.

By "constitutively active" is meant that the chimeric stimulating polypeptide's cell activation activity is active even in the absence of an inducer. One method to generate constitutively active signalling is to tether the activation protein factor to the plasma membrane via a transmembrane domain or lipid targeting moiety.

Immune cell therapies may also be designed to provide constitutively active therapy, such as constitutively active T cells or NK-cells, but provide an inducible safety switch, to stop, or reduce the level of, the therapy when needed (see above). In some embodiments, immune cells, such as CIR-T cells or CIR-NK cells, express a chimeric antigen receptor, and a chimeric signaling polypeptide.

8. Linker Polypeptides

Where it is desired to encode two polypeptides in a single gene, such that they are encoded on a single transcript, the two polypeptides can be joined by a linker polypeptide. For instance, these may be included between MyD88 and CD40 in a MyD88-CD40 chimeric polypeptide, or between the costimulatory polypeptide cytoplasmic signaling region and the CD3ζ portion of a CAR or CIR. A linker can be positioned between any of the regions/domains described herein, where desired. For example, in some cases, a linker is positioned: between the TM domain and the signaling region or costimulatory region, between the ILT2 or ILT4 targeting region (e.g., D1-D2 domain) and the stalk, between a signaling region and a costimulatory region, between two costimularoty domains, between a costimulatory or signaling region and a T2A sequence, or any combination thereof.

Linker polypeptides include cleavable and non-cleavable linker polypeptides. Examples of linkers include, but are not limited to: SGR, GS, VD, and PRGSG (SEQ ID NO: 67). Additional linkers will be known to one of ordinary skill in the art and any convenient linker can be used.

Linker polypeptides include those for example, consisting of about 2 to about 30 amino acids e.g. furin cleavage site, $(GGGGS)_n$ (SEQ ID NO: 109). In some embodiments, the linker polypeptide consists of about 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids. In some embodiments, the linker polypeptide consists of about 18 to 22 amino acids. In some embodiments, the linker polypeptide consists of 20 amino acids.

Cleavable linkers include linkers that are cleaved by an enzyme in the modified cells. The enzyme may be exogenous to the cells, for example, an enzyme encoded by a polynucleotide that is introduced into the cells by transfection or transduction, either at the same time or a different time as the polynucleotide that encodes the linker. In some embodiments, cleavable linkers include linkers that are cleaved by an enzyme endogenous to the modified cells in the population, including, for example, enzymes that are naturally expressed in the cell, and enzymes encoded by polynucleotides native to the cell, such as, for example, lysozyme. The term "cleavable linker" also extends to a linker which is cleaved by any means, including, for example, non-enzymatic means, such as peptide skipping.

One advantage of a cleavable linker is that it permits an essentially fixed stoichiometric ratio of expression of two polypeptides (a 1:1 ratio if two mature polypeptides are linked by a single cleavable linker).

The linker polypeptide may be a 2A-like sequence, which can be derived from many different viruses, including, for example, from the *Thosea asigna* insect virus. These sequences are sometimes also known as "peptide skipping sequences." When this type of sequence is placed within a cistron, between two polypeptides that are intended to be separated, the ribosome appears to skip a peptide bond, in the case of *Thosea asigna* sequence; the bond between the Gly and Pro amino acids at the carboxy terminal "P-G-P" is omitted. This may leave two to three polypeptides, for example, an inducible chimeric pro-apoptotic polypeptide and a chimeric antigen receptor, or, for example, a marker polypeptide and an inducible chimeric pro-apoptotic polypeptide. When this sequence is used, the polypeptide that is encoded 5' of the 2A sequence may end up with additional amino acids at the carboxy terminus, including the Gly residue and any upstream residues in the 2A sequence. The peptide that is encoded 3' of the 2A sequence may end up with additional amino acids at the amino terminus, including the Pro residue and any downstream residues following the 2A sequence.

In some embodiments, the cleavable linker is a 2A polypeptide derived from porcine teschovirus-1 (β2A). In some embodiments, the 2A cotranslational sequence is a 2A-like sequence. In some embodiments, the 2A cotranslational sequence is T2A (*Thosea asigna* virus 2A), F2A (foot and mouth disease virus 2A), β2A (porcine teschovirus-1 2A), BmCPV 2A (cytoplasmic polyhedrosis virus 2A) BmIFV 2A (flacherie virus of *B. mori* 2A), or E2A (equine rhinitis A virus 2A). In some embodiments, the 2A cotranslational sequence is T2A-GSG, F2A-GSG, β2A-GSG, or E2A-GSG. In some embodiments, the 2A cotranslational sequence is selected from the group consisting of T2A, P2A and F2A. In a specific embodiment, a 2TA comprises (or consists of) a sequence disclosed herein. comprises (consists of) a sequence disclosed herein (e.g., a sequence disclosed in the Examples below).

2A-like sequences are sometimes "leaky" in that some of the polypeptides are not separated during translation, and instead, remain as one long polypeptide following translation. One theory as to the cause of the leaky linker, is that the short 2A sequence occasionally may not fold into the required structure that promotes ribosome skipping (a "2A fold"). In these instances, ribosomes may not miss the proline peptide bond, which then results in a fusion protein. To reduce the level of leakiness, and thus reduce the number of fusion proteins that form, a GSG (or similar) linker may be added to the amino terminal side of the 2A polypeptide; the GSG linker blocks secondary structures of newly-translated polypeptides from spontaneously folding and disrupting the '2A fold'. A leaky 2A sequence can be used, for example, so that the same encoded polypeptide can sometimes be directed to the cell surface but other times remain in the cytosol.

In certain embodiments, a 2A linker includes the amino acid sequence of SEQ ID NO: 11. In certain embodiments, the 2A linker further includes a GSG amino acid sequence at the amino terminus of the polypeptide, in other embodiments, the 2A linker includes a GSGPR (SEQ ID NO: 68) amino acid sequence at the amino terminus of the polypeptide. Thus, by a "2A" sequence, the term may refer to a 2A sequence in an example described herein or may also refer to a 2A sequence as listed herein further comprising a GSG or GSGPR (SEQ ID NO: 68) sequence at the amino terminus of the linker.

In some embodiments, the linker, for example, the 2A linker, is cleaved in about 10, 20, 30, 40, 50, 60, 70, 75, 80, 85, 90, 95, 98, or 99% of the translated polypeptides.

Suitable linker polypeptides (including T2A linkers) for use with the invention are disclosed in Tables 4-42 (including the 'flex' linker polypeptide sequences).

9. Membrane-Targeting Sequences

A membrane-targeting sequence provides for transport of a chimeric protein to the cell surface membrane. Molecules in association with cell membranes contain certain regions that facilitate the membrane association, and such regions can be incorporated into a chimeric protein molecule to generate membrane-targeted molecules. In some embodiments a CIR can be transported to the cell surface through signal-dependent translation into the lumen of the endoplasmic reticulum through the natural signal peptide of ILT2 or ILT4. In other embodiments this natural signal peptide can be replaced by that of other secreted proteins. In these embodiments, the signal peptide may be derived from GM- CSF or an Immunoglobulin light-chain, but is not limited to derivation from these proteins.

For example, some proteins contain sequences at the N-terminus or C-terminus that are acylated, and these acyl moieties facilitate membrane association. Such sequences are recognized by acyltransferases and often conform to a particular sequence motif. Certain acylation motifs are capable of being modified with a single acyl moiety (often followed by several positively charged residues (e.g. human c-Src: MGSNKSKPKDASQRRR, SEQ ID NO: 69) to improve association with anionic lipid head groups) and others are capable of being modified with multiple acyl moieties. For example, the N-terminal sequence of the protein tyrosine kinase Src can comprise a single myristoyl moiety. Dual acylation regions are located within the N-terminal regions of certain protein kinases, such as a subset of Src family members (e.g., Yes, Fyn, Lck) and G-protein alpha subunits. Such dual acylation regions often are located within the first eighteen amino acids of such proteins, and conform to the sequence motif Met-Gly-Cys-Xaa-Cys (SEQ ID NO: 110), where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can be modified with C15 or C10 isoprenyl moieties, from the C-terminus of G-protein gamma subunits and other proteins (e.g., "ht" followed "tps" followed by ":/" followed by "/" followed by "ww" followed by "w.ebi.ac.uk" followed by "/interpro/entry/InterPro/IPR031771/"; or "ht" followed "tps" followed by ":/" followed by "/" followed by "prosite.exp" followed by "asy.org/PS00294") also can be utilized. These and other acylation motifs include, for example, those discussed in Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997), and can be incorporated in chimeric molecules to induce membrane localization.

In some embodiments, the membrane-targeting region comprises a myristoylation region. In some embodiments, the membrane-targeting region is selected from the group consisting of myristoylation-targeting sequence, palmitoylation-targeting sequence, prenylation sequences (i.e., farnesylation, geranyl-geranylation, CAAX Box), protein-protein interaction motifs or transmembrane sequences (utilizing signal peptides) from receptors. Examples include those discussed in, for example, ten Klooster et al, Biology of the Cell (2007) 99, 1-12, or Vincent et al., Nature Biotechnology 21:936-40, 1098 (2003).

Where a polypeptide does not include a membrane-targeting region, or lacks a membrane-targeting region, such as certain chimeric polypeptides provided herein, the polypeptide does not include a region that provides for transport of the chimeric protein to a cell membrane. The polypeptide may, for example, not include a sequence that transports the polypeptide to the cell surface membrane, or the polypeptide may, for example, include a dysfunctional membrane-targeting region, that does not transport the polypeptide to the cell surface membrane, for example, a myristoylation region that includes a proline that disrupts the function of the myristoylation-targeting region. (see, for example, Resh, M. D., Biochim. Biophys. Acta. 1451:1-16 (1999)). Polypeptides that are not transported to the membrane are considered to be cytoplasmic polypeptides.

Suitable myristoylation sequences for use with the invention are disclosed in Tables 4-42.

10. Genetically Modified Cells

The genetically modified cells (cells such as immune cells that express, e.g., include a nucleic acid that encodes, a subject chimeric ILT receptor) may be any cells useful in cell therapy, e.g., immune cells. The cells may be, for example, T cells, natural killer (NK) cells, B cells, macrophages, peripheral blood cells, hematopoietic progenitor cells, or bone marrow cells. In preferred embodiments, the modified cells are T cells, natural killer cells, or natural killer T cells.

Cells which are genetically modified as disclosed herein (cells such as immune cells that express, e.g., include a nucleic acid that encodes, a subject chimeric ILT receptor) are useful for administering to subjects who can benefit from receiving them e.g. who can benefit from donor lymphocyte administration. These subjects will typically be humans, so the invention will typically be performed using human cells.

Sources of Cells

Cells to be genetically modified may be autologous, syngeneic, or allogeneic. Allogeneic cells can be derived from any healthy donor, and syngeneic cells from any healthy donor who is appropriately related to the intended recipient. The donor will generally be an adult (at least 18 years old) but children are also suitable as cell donors (e.g. see Styczynski 2018, *Transfus Apher Sci* 57(3):323-330).

The term "autologous" means a cell derived from the same individual to which it is later administered. The term "allogeneic" refers to HLA or MHC loci that are antigenically distinct between the host and donor cells. Thus, cells from the same species can be antigenically distinct. The term "syngeneic" refers to cells that have genotypes that are identical or closely related enough to allow tissue transplant, or are immunologically compatible. For example, identical twins or close relatives can be syngeneic.

The cells may be blood cells. For example, the source of the cells may be, for example, umbilical cord blood, bone marrow, or peripheral blood, and they may be peripheral blood mononuclear cells (PBMCs). These include lymphocytes (e.g. T cells, B cells, NK cells) or monocytes. The term "peripheral blood" as used herein, refers to cellular components of blood (e.g., red blood cells, white blood cells and platelets), which are obtained or prepared from the circulating pool of blood and not sequestered within the lymphatic system, spleen, liver or bone marrow. Umbilical cord blood is distinct from peripheral blood and blood sequestered within the lymphatic system, spleen, liver or bone marrow, and it refers to blood that remains in the placenta and in the attached umbilical cord after child birth. Cord blood often contains stem cells including hematopoietic cells.

A suitable process for obtaining T cells from a human is described in the published protocol which accompanied Di Stasi et al. (2011) *N Engl J Med* 365:1673-83 ('The Protocol'). In general terms, T cells are obtained, subjected to genetic modification and selection, and can then be administered to recipient subjects. A useful source of T cells is a person's peripheral blood. Peripheral blood samples will generally be subjected to leukapheresis to provide a sample enriched for white blood cells. This enriched sample (also known as a leukopak) can be composed of a variety of blood cells including monocytes, lymphocytes, platelets, plasma, and red cells. A leukopak typically contains a higher concentration of cells as compared to venipuncture or buffy coat products.

Although the sample may be subjected to allodepletion (as discussed in The Protocol), it is preferred that the sample is not subjected to allodepletion. Preferred samples are thus alloreplete, as discussed in Zhou et al. (2015) *Blood* 125: 4103-13. These populations can provide a more robust T cell repertoire for therapeutic purposes. Preferred compositions of the invention are thus not T cell allodepleted, and have not been subject to a step of allodepletion.

T cells are generally cultured (usually under activating conditions e.g. using anti-CD3 and/or anti-CD28 antibodies, optionally with IL-2) prior to being genetically modified. This step provides higher yields of T cells at the end of the modification process.

A process for obtaining and expanding NK cells from a human is described in Cho & Campana (2009) *Korean J Lab Med* 29:89-96, Somanchi et al. (2011) *J Vis Exp* 48:2540 and in Wang et al (2020) *Blood Adv.* 4:1950.

CD4+ and CD8+ T Cells

A subject composition can include CD4+ and CD8+ T cells. Whereas the ratio of CD4+ cells to CD8+ cells in a leukopak is typically above 2, in some embodiments the ratio of genetically-modified CD4+ cells to genetically-modified CD8+ cells in a composition of the invention is less than 2 e.g. less than 1.5. Ideally there are more genetically-modified CD8+ T cells than genetically-modified CD4+ T cells in the composition i.e. the ratio is less than 1 e.g. less than 0.9, less than 0.8, less than 0.7, less than 0.6, or preferably even less than 0.5. Thus an overall procedure starting from donor cells and producing genetically-modified T cells ideally enriches for CD8+ cells T cells relative to CD4+ T cells. Preferably at least 60% of the genetically-modified T cells are CD8+ T cells, and more preferably at least 65%. Within the population of genetically-modified CD3+ T cells a preferred range for CD8+ T cells is between 55-75% e.g. from 63-73%. The proportions of CD8+ and CD4+ T cells can easily be assessed by flow cytometry, and methods for sorting and counting CD4+ and CD8+ T cells are conventional in the art.

Memory T Cell Subsets (See Mahnke et al. (2013) *Eur J Immunol* 43:2797-809)

A population of genetically-modified T cells can include terminal effector memory T cells (defined as CD45RA+ CD45RO−CCR7− cells; 'TEMRA'), T-effector memory cells (defined as CD45RA−CD45RO+CCR7− cells; 'EM'), T-central memory cells (defined as CD45RA−CD45RO+ CCR7+ cells; 'CM'), and naïve T cells (defined as CD45RA+CD45RO−CCR7+ cells). These cells can be assessed by flow cytometry using the CD45RA/RO and CCR7 markers. Labelled reagents which recognise CCR7 and which can distinguish between the CD45RA and CD45RO isoforms are readily available from commercial suppliers.

An average leukopak typically contains ~20% each of terminal effector and T-effector memory cells. An overall procedure from donor cells to genetically-modified T cells may enrich for terminal effector memory T cells relative to T-effector memory cells.

In some embodiments, less than 60% of the genetically-modified T cells are naïve T cells e.g. less than 58%, preferably less than 55%, and more preferably less than 50%. Within the population of genetically-modified CD3+ T cells a preferred range for naïve T cells is between 30-60%, more preferably 42-49%, and most preferably from 43-46%. This proportion of naïve T cells has been seen to correlate with favourable outcomes in T cell recipients. Naïve EM cells can be assessed by flow cytometry using the CD45RA/RO and CCR7 markers.

Within a population of genetically modified T cells, in addition to TEMRA, EM and naïve T cells, the proportion of T-central memory cells is generally <10%.

In some embodiments, a population of genetically-modified T cells in a composition comprises about 10% to about 40% CD4+ T cells and about 60% to about 90% CD8+ T cells. The population of genetically-modified CD3+ T cells can comprise about 15% to about 40% CD4+ T cells and about 60% to about 85% CD8+ T cells, more preferably about 20% to about 40% CD4+ T cells and about 60% to about 80% CD8+ T cells.

NK Cells

NK cells, also known as natural killer cells or large granular lymphocytes (LGL), are cytotoxic lymphocytes critical to the innate immune system. The role of NK cells is analogous to that of cytotoxic T cells in the vertebrate adaptive immune response. NK cells provide rapid responses to virus-infected cells and respond to tumor formation.

T cells rely on priming interactions between the T-cell receptor (TCR) and MHC-peptide complexes on target cells as a necessary first step in T-cell activation. As a result, T cells can recognize a single antigen, and tumor cells may avoid T-cell recognition through mutations that significantly reduce antigen presentation. In contrast, NK cells are capable of recognizing a multitude of transformed and infected cells without being dependent on the presentation of a single antigen. Therefore, treatment with NK cells can bypass some of the resistance mechanisms to T-cell based therapy.

As innate cells, NK cells can secrete proinflammatory chemokines and cytokines to recruit and activate the body's adaptive immune system, consisting of T and B cells, creating a second wave of durable antitumor response. Furthermore, NK cells are not associated with certain toxicities associated with CAR-T cell therapy such as cytokine release syndrome and central nervous system toxicity.

NK cells can be useful as a source for antigen or receptor-based directed cell therapy because of their innate cytotoxic mechanisms. NK cells comprise approximately 10-15% of the lymphocytes in peripheral blood of a typical donor and can be readily purified, expanded and virally transduced. In instances of loss of the target of a directed cell therapy, for example HLA-G, on a cells within a tumor, an activated NK cell has alternative inate mechanisms to direct cytotoxic function including NKG2D, p46, p44, p30, DNAM and CD16.

Genetic Modification of Cells

Cells are genetically modified by transferring an expression construct (encoding a subject chimeric ILT receptor) into them. Such transfer may employ viral or non-viral methods of gene transfer. This section provides a discussion of methods and compositions of gene transfer.

An expression vector can be introduced into a cell by various means. The term "transfection" and "transduction" are interchangeable and refer to the process by which an exogenous nucleic acid sequence is introduced into a eukaryotic host cell. Transfection (or transduction) can be achieved by any one of a number of means including electroporation, microinjection, gene gun delivery, retroviral infection, lipofection, superfection and the like.

Any appropriate method may be used to transfect or transform the cells (e.g. the T cells or NK cells). Certain non-limiting examples are presented herein. In some embodiments, the viral vector is an SFG-based viral vector, as discussed in Tey et al. (2007) *Biol Blood Marrow Transpl* 13:913-24 and by Di Stasi et al., (2011) *N Engl J Med* 365:1673-83.

The cells can be transduced using a viral vector encoding polypeptides described herein. Suitable transduction techniques may involve fibronectin fragment CH-296. As an alternative to transduction using a viral vector, cells can be transfected with any suitable method known in the art such as with DNA encoding the relevant polypeptides e.g. using calcium phosphate, cationic polymers (such as PEI), magnetic beads, electroporation and commercial lipid-based reagents such as Lipofectamine™ and Fugene™. One result of the transduction/transfection step is that various donor cells will now be genetically-modified cells which can express the CIR and any other desired polypeptides.

In some embodiments, the viral vector used for transduction is the retroviral vector disclosed by Tey et al. (2007) *Biol Blood Marrow Transpl* 13:913-24 and by Di Stasi et al. (2011) *supra*. This vector is based on Gibbon ape leukemia virus (Gal-V) pseudotyped retrovirus encoding an iCasp9 suicide switch and a ΔCD19 cell surface transgene marker (see further below). It can be produced in the PG13 packaging cell line, as discussed by Tey et al. (2007) *supra*. Other viral vectors encoding the desired proteins can also be used. In some embodiments, retroviral vectors that can provide a high copy number of proviral integrants per cell are used for transduction.

After transduction/transfection, cells can be separated from transduction/transfection materials and cultured again, to permit the genetically-modified cells to expand. Cells can be expanded so that a desired minimum number of genetically-modified cells is achieved.

Genetically-modified cells can then be selected from the population of cells which has been obtained. The CIR may not be suitable for positive selection of desired cells, so in some embodiments, the genetically-modified cells should express a cell surface transgene marker of interest (see below). Cells which express this surface marker can be selected e.g. using immunomagnetic techniques. For instance, paramagnetic beads conjugated to monoclonal antibodies which recognise the cell surface transgene marker of interest can be used, for example, using a CliniMACS system (available from Miltenyi Biotec).

In an alternative procedure, genetically-modified cells are selected after a step of transduction, are cultured, and are then fed. Thus, the order of transduction, feeding, and selection can be varied.

The result of these procedures is a composition containing cells which have been genetically modified, and which can thus express the Chimeric ILT receptor (and any other desired polypeptides e.g. a costimulatory polypeptide, a suicide switch, a cell surface transgene marker, etc.). These genetically-modified cells can be administered to a recipient, but they might first be preserved (e.g. cryopreserved), optionally after further expansion, before being administered.

Selectable Markers

Cells may be modified to express polypeptides whose expression can be identified in vitro or in vivo, thereby permitting selection of genetically-modified cells e.g. to separate them from unmodified cells. Such markers confer an identifiable change to the cell, permitting easy identification of cells containing the desired expression construct.

Inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as Herpes Simplex Virus thymidine kinase (tk) are employed.

Immunologic surface markers containing the extracellular, non-signaling domains or various proteins (e.g. CD34, CD19, LNGFR) also can be employed, permitting a straightforward method for magnetic or fluorescence antibody-mediated sorting. These markers can be detected e.g. using a labelled antibody which binds to the protein.

The selectable marker employed is not believed to be important, so long as it is capable of being expressed simultaneously with the nucleic acid encoding a desired gene product e.g. a subject CIR. Moreover, the marker should ideally be a polypeptide which is not expressed by the initial (donor) cells, although difference in expression levels can be used in situations where the marker is indeed endogenous to the initial cells.

Ideally the marker is based on a human proteins as this minimises the risk that cells expressing the marker will be recognised as foreign by a human subject's immune system (e.g. after they are administered therapeutically). For instance, where T cells are the desired type of cell, human CD proteins which are not naturally expressed by T cells can be used for this purpose.

The genetically modified cells provided herein may express a cell surface transgene marker, present on an expression vector that expresses a subject CIR, and/or, in some embodiments, present on an expression vector that encodes a protein other than the CIR, such as, for example a CAR, a pro-apoptotic polypeptide safety switch, or a costimulatory polypeptide.

In one embodiment, the cell surface transgene marker is a truncated CD19 (ΔCD19) polypeptide (Di Stasi et al. (2011) supra) that comprises a human CD19 truncated at amino acid 333 to remove most of the intracytoplasmic domain (see, e.g., SEQ ID Nos. 12 (nucleotides) and 13 (protein)). The extracellular CD19 domain can still be recognised (e.g. in flow cytometry, FACS or MACS) but the potential to trigger intracellular signalling is minimised. CD19 is normally expressed by B cells, rather than by T cells or NK cells, so selection of CD19+ cells permits genetically-modified cells (e.g. T cells, NK cells or NKT cells) to be separated from unmodified cells.

Another useful marker is CD34, which has a 16 amino acid minimal epitope (SEQ ID NO 41) that is useful as a marker.

By encoding a desired protein at the 5' end of an encoding gene, and a marker at the 3' end, the risk of selecting cells which do not have the desired polypeptide (e.g. due to premature termination of translation) is minimised. In this manner, expression of the marker and of the desired polypeptide run in parallel.

Suitable CD34 marker sequences for use with the invention are disclosed in Tables 4-42.

11. Engineering Expression Constructs

Provided are nucleic acids that include a nucleotide sequence encoding a subject chimeric ILT receptor (CIR). In some cases, such a nucleic acid is an expression construct. Expression constructs for expressing the Chimeric ILT Receptor (and optionally, other desired polypeptides such as chimeric antigen receptors, signaling polypeptides, safety switches, etc.) are provided herein. In some examples, one or more polypeptides is said to be "operably linked" to a promoter, which indicates that the promoter sequence is functionally linked to a second sequence, wherein the promoter sequence is in the correct location and orientation in relation to that second sequence to control RNA polymerase initiation and transcription of the DNA corresponding to the second sequence, whereby the resulting transcript encodes a polypeptide of interest.

A "promoter" is a DNA sequence recognized by the synthetic machinery of the cell, or introduced synthetic machinery, required to initiate the specific transcription of a gene. In some embodiments, the promoter is a developmentally regulated promoter i.e. a promoter that acts as the initial binding site for RNA polymerase to transcribe a gene which is expressed under certain conditions that are controlled, initiated by or influenced by a developmental program or pathway.

The term "expression construct" is any type of genetic construct containing a nucleic acid coding for gene products in which part or all of the nucleic acid encoding sequence is capable of being transcribed. The transcript can be translated into a protein, but it need not be. In certain embodiments, expression includes both transcription of a gene and translation of mRNA into a gene product. In other embodiments, expression only includes transcription of the nucleic acid encoding genes of interest. Expression vectors can contain a variety of control sequences, which refer to nucleic acid sequences necessary for the transcription and possibly translation of an operatively linked coding sequence in a particular host organism.

A "vector" is capable of transferring nucleic acid sequences to target cells (e.g., viral vectors, non-viral vectors, particulate carriers, and liposomes). Typically, "vector construct," "expression vector," "expression construct," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

In certain examples, a polynucleotide coding for the CIR is included in the same vector, such as, for example, a viral or plasmid vector, as a polynucleotide coding for a second polypeptide. This second polypeptide may be, for example (and as described elsewhere herein), a downregulator of endogenous proteins, a blocking antibody or scFv for inhibitory receptors, a signaling polypeptide, an inducible suicide switch, or a marker polypeptide. In other examples added expressed transcription products may not encode proteins, but instead generate short hairpin RNA products designed to remove the expression of certain endogenous RNAs that encode unwanted proteins in the cell product.

A construct may be designed with one promoter operably linked to a nucleic acid comprising a polynucleotide coding for a fusion protein of the polypeptides, linked by a linker polypeptide (e.g. a cleavable linker polypeptide, such as a 2A polypeptide). In this example, the first and second polypeptides are produced during a single translation event, but they may then be separated. In other examples, the two polypeptides may be expressed separately from the same vector, where each nucleic acid comprising a polynucleotide coding for one of the polypeptides is operably linked to a separate promoter. In yet other examples, one promoter may be operably linked to the two polynucleotides, directing the production of two separate RNA transcripts, and thus two polypeptides; in one example, the promoter may be bi-directional, and the coding regions may be in opposite directions 5'-3'. Therefore, expression constructs discussed herein may comprise at least one, or at least two promoters.

In yet other examples, two polypeptides (such as, for example, the CIR and a marker protein) may be expressed in a cell using two separate vectors. The cells may be co-transfected or co-transformed with the vectors, or the vectors may be introduced to the cells at different times.

Any combinations of these approaches may be used, in order to achieve expression of desired polypeptides in a genetically modified cell.

In some embodiments, a nucleic acid construct is contained within a viral vector. In certain embodiments, the viral vector is a retroviral vector. In certain embodiments, the viral vector is an adenoviral vector or a lentiviral vector. It is understood that in some embodiments, a cell is contacted with the viral vector ex vivo, and in some embodiments, the cell is contacted with the viral vector in vivo. Thus, an expression construct may be inserted into a vector, for example a viral vector or plasmid. The steps of the methods provided may be performed using any suitable method; these methods include, without limitation, methods of transducing, transforming, or otherwise providing nucleic acid to the cell, described herein.

The particular promoter employed to control the expression of a polynucleotide sequence of interest is generally not of particular importance, so long as it is capable of directing the expression of the polynucleotide in a desired cell. Thus, where a human cell is targeted the polynucleotide sequence-coding region may, for example, be placed adjacent to and under the control of a promoter that is capable of being expressed in a human cell. Generally speaking, such a promoter might include either a human or viral promoter. Promoters may be selected that are appropriate for the vector used to express the CIRs and other polypeptides provided herein.

In various embodiments, where, for example, the expression vector is a retrovirus, an example of an appropriate promoter is the Murine Moloney leukemia virus promoter. In other embodiments, the promoter may be, for example, the CMV immediate early gene promoter, the SV40 early promoter, the Rous sarcoma virus long terminal repeat, β2-microglobulin, ribosomal protein 31, phosphoglycerate kinase, EF1α, □-actin, rat insulin promoter and glyceraldehyde-3-phosphate dehydrogenase can be used to obtain high-level expression of the coding sequence of interest. The use of other viral or mammalian cellular promoters which are well known in the art to achieve expression of a coding sequence of interest is contemplated as well, provided that the levels of expression are sufficient for a given purpose. By employing a promoter with well-known properties, the level and pattern of expression of the polypeptide of interest following transfection or transformation can be optimized.

In other embodiments the expression vector is a transposon such that the genetic elements encoding a CIR and associated marker proteins, coactivation proteins or inhibitors of endogenous factors or the tumor microenvironment a carried on a plasmid vector carrying elements recognized by a transiently coexpressed transposase. The action of the transposase is to catalyse the fusion of the transgenes carried between repeated elements recognized by the transposase with the cells genome. Examples of transposon systems that can be used in these embodiments are the Sleeping Beauty system and the Piggyback system. Promoter elements carried within the transposon direct transgene expression. The promoter may be, for example the CMV immediate early gene promoter, the SV40 early promoter, the Rous sarcoma virus long terminal repeat, β2-microglobulin, ribosomal protein 31, phosphoglycerate kinase, EF1α, β-actin, rat insulin promoter and glyceraldehyde-3-phosphate dehydrogenase. The methods for introduction of the plasmids for the transposon and transposase to cells is transfection rather than viral transduction.

Promoters, and other regulatory elements, are selected such that they are functional in the desired cells or tissue. In addition, this list of promoters should not be construed to be exhaustive or limiting; other promoters that are used in conjunction with the promoters and methods disclosed herein.

It is understood that the order of the polynucleotides may vary and may be tested to determine the suitability of the construct for any particular method, thus, the nucleic acid may include the polynucleotides in varying orders, which also take into account a variation in the order of components (a) to (d). And, the nucleic acid may include the first through fourth polynucleotides in any of the following orders, where 1, 2, 3 & 4 (representing, e.g., the arrangement of components in the intracellular region, e.g., (1) a signaling region, (2) a first costimulatory domain, (3) a second costimulatory domain, and (4) a surface marker) indicate the first, second, third and fourth order of the polynucleotides in the nucleic acid from the 5' to 3' direction. It is understood that other polynucleotides, such as those that code for a 2A polypeptide, for example, may be present between the listed polynucleotides when appropriate.

TABLE 1

| (a) | (b) | (c) | (d) | (a) | (b) | (c) | (d) | (a) | (b) | (c) | (d) | (a) | (b) | (c) | (d) |
|---|---|---|---|---|---|---|---|---|---|---|---|---|---|---|---|
| 1 | 2 | 3 | 4 | 2 | 1 | 3 | 4 | 3 | 1 | 2 | 4 | 4 | 1 | 2 | 3 |
| 1 | 2 | 4 | 3 | 2 | 1 | 4 | 3 | 3 | 1 | 4 | 2 | 4 | 2 | 1 | 3 |
| 1 | 3 | 2 | 4 | 2 | 3 | 1 | 4 | 3 | 2 | 1 | 4 | 4 | 2 | 1 | 3 |
| 1 | 3 | 4 | 2 | 2 | 3 | 4 | 1 | 3 | 2 | 4 | 1 | 4 | 2 | 3 | 1 |
| 1 | 4 | 2 | 3 | 2 | 4 | 1 | 3 | 3 | 4 | 1 | 2 | 4 | 3 | 1 | 2 |
| 1 | 4 | 3 | 2 | 2 | 4 | 3 | 1 | 3 | 4 | 2 | 1 | 4 | 3 | 2 | 1 |

Similarly, the nucleic acids may include only three of the polynucleotides coding for three of the polypeptides provided in the table above. In some examples, a cell is transfected or transduced with a nucleic acid comprising the four polynucleotides included in Table 1 above. In other examples, a cell is transfected or transduced with a nucleic acid that encodes three of the polynucleotides, coding for three of the polypeptides, as provided, for example, in Table 2.

TABLE 2

| (a) | (b) | (c) | (d) | (a) | (b) | (c) | (d) | (a) | (b) | (c) | (d) |
|---|---|---|---|---|---|---|---|---|---|---|---|
| 1 | 2 | 3 |   | 2 | 1 | 3 |   | 3 | 1 | 2 |   |
| 1 | 2 |   | 3 | 2 | 1 |   | 3 | 3 | 1 |   | 2 |
| 1 | 3 | 2 |   | 2 | 3 | 1 |   | 3 | 2 | 1 |   |
| 1 | 3 |   | 2 | 2 | 3 |   | 1 | 3 | 2 |   | 1 |
| 1 |   | 2 | 3 | 2 |   | 1 | 3 | 3 |   | 1 | 2 |
| 1 |   | 3 | 2 | 2 |   | 3 | 1 | 3 |   | 2 | 1 |

Similarly, the nucleic acids may include only two of the polynucleotides, coding for two of the polypeptides provided in the tables above.

TABLE 3

| (a) | (b) | (c) | (d) |
|---|---|---|---|
| 1 | 2 |   |   |
| 1 |   | 2 |   |
| 1 |   |   | 2 |

Modifying the order of various polypeptide elements is visible, for instance, in Tables 4-42.

In some embodiments, the cell is transfected or transduced with the nucleic acid that encodes two of the polynucleotides, and the cell also comprises a nucleic acid comprising a polynucleotide coding for the third polypeptide and/or the cell also comprises a nucleic acid comprising a polynucleotide coding for the fourth polypeptide. In some embodiments, the cell is transfected or transduced with the nucleic acid that encodes three of the polynucleotides, and the cell also comprises a nucleic acid comprising a polynucleotide coding for the fourth polypeptide. For example, a cell may comprise a nucleic acid comprising the first, second and third polynucleotides, and the cell may also comprise a nucleic acid comprising a polynucleotide coding for a chimeric Caspase-9 polypeptide. Also, a cell may comprise a nucleic acid comprising the first, second and fourth polynucleotides, and the cell may also comprise a nucleic acid comprising a polynucleotide coding for a Chimeric ILT receptor, an scFv modulator of natural ILT2 function or Interleukin-15.

12. Methods for Treating a Disease

Also provided are methods of treatment or prevention of a disease where administration of cells (e.g., cells expressing a subject CIR) by, for example, infusion, may be beneficial. The cells may, for example, be used in regeneration, for example, to replace the function of diseased cells. The genetically-modified cells described herein may be used for cell therapy.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

An "effective amount" or "sufficient amount" refers to an amount (e.g., an effective amount of cells) providing, in single or multiple doses, alone or in combination, with one or more other compositions (therapeutic agents such as a drug), treatments, protocols, or therapeutic regimens, a detectable response of any duration of time (long or short term), an expected or desired outcome in or a benefit to a subject of any measurable or detectable degree or for any duration of time (e.g., for minutes, hours, days, months, years, or cured).

The doses of an "effective amount" or "sufficient amount" for treatment (e.g., to ameliorate or to provide a therapeutic benefit or improvement) typically are effective to provide a response to one, multiple or all adverse symptoms, consequences or complications of a disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is also a satisfactory outcome.

Genetically-modified cells provided herein (i.e., cells expressing a subject CIR) can be used in methods for treating human subjects in need thereof, and can be used to prepare medicaments for treating such subjects. The cells will usually be delivered to the recipient subject by infusion.

The genetically-modified cells may be T cells, iNKT cells, macrophage or NK cells. A typical dose of T or NK cells for therapy in a subject is between $10^5$-$10^7$ cells/kg. Pediatric patients will generally receive a dose of around $10^6$ cells/kg, whereas adult patients will receive a higher dose e.g. $3\times10^6$ cells/kg.

In general terms, genetically modified T and NK cells of the invention can be used in the same manner as known donor leukocyte infusion (DLI), but they have the added benefit of the CIR.

Subjects receiving genetically-modified T cells or NK cells will typically also receive other tissue from an allogeneic donor e.g. they can receive haematopoietic cells and/or haematopoietic stem cells (e.g. CD34+ cells). This allograft tissue and the genetically-modified T cells are ideally derived from the same donor, such that they will be genetically matched. Furthermore, the donor and the recipient are preferably haploidentical e.g. a matched unrelated donor, or a suitable family member. For instance, the donor may be the recipient's parent or child. Where a subject is identified as being in need of genetically-modified T cells, therefore, a suitable donor can be identified as a T cell donor.

A recipient may undergo lymphodepletive conditioning prior to receiving the genetically-modified T cells (and prior to receiving an allograft). Thus the recipient's own α/β T cells (and B cells) can be depleted prior to receiving the genetically-modified T cells or NK cells.

The recipient may have a hematological cancer (such as a treatment-refractory hematological cancer) or an inherited blood disorder. For instance, the recipient may have acute lymphoblastic leukemia (ALL), acute myeloid leukemia (AML), severe combined immune-deficiency (SCID), Wiskott-Aldrich syndrome (WA), Fanconi Anemia, chronic myelogenous leukemia (CML), non-Hodgkin lymphoma (NHL), Hodgkin lymphoma (HL), or multiple myeloma.

The recipient of CIR-expressing T cells or NK cells may have non-hematological cancer expressing HLA-G. For instance, the recipient may have renal cell cancer (RCC), non-small cell lung cancer (NSCLC), colorectal cancer (CRC), breast cancer, neuroblastoma, hepatocellular cancer (HCC).

Other cell-types can also be used in therapy, and include any cell administered to a patient for a desired therapeutic result. The therapeutic cells may be, for example, immune cells such as, for example, T cells, natural killer cells, B cells, tumor infiltrating lymphocytes, or macrophages, or a combination thereof; the therapeutic cells may be, for example, peripheral blood cells, hematopoietic progenitor cells, bone marrow cells, or tumor cells. To further improve the tumor microenvironment to be more immunogenic, the treatment may be combined with one or more adjuvants (e.g., IL-12, TLRs, IDO inhibitors, etc.). In some embodiments, the cells may be delivered to treat a solid tumor, such as, for example, delivery of the cells to a tumor bed.

Also provided in some embodiments are nucleic acids which may be administered to a subject, thereby transforming or transducing target cells in vivo to form the genetically-modified cells in situ.

An effective amount of genetically-modified cells is administered. To determine if an effective amount of ligand or modified cells is administered, any means of assaying or measuring the number of target cells, or amount of target antigen, or size of a tumor may be used to determine whether the number of target cells, amount of target antigen or size of a tumor has increased, decreased, or remained the same. Samples, images, or other means of measurement taken before administration of the modified cells or ligand may be used to compare with samples, images, or other means of measurement taken after administration of the modified cells or ligand. Thus, for example, to determine whether the amount or concentration of cells expressing a target antigen has increased, decreased, or remained the same, a first sample may be obtained from a subject before administration of the ligand or modified cells, and a second sample may be obtained from a subject after administration of the ligand or modified cells. The amount or concentration of cells expressing the target antigen in the first sample may be compared with the amount or concentration of cells expressing the target antigen in the second sample, in order to determine whether the amount or concentration of cells expressing the target antigen has increased, decreased, or remained the same following administration of the ligand or modified cell.

The effective amount for any particular application can vary depending on such factors as the disease or condition being treated, the particular composition being administered, the size of the subject, and/or the severity of the disease or condition. One can empirically determine the effective amount of a particular composition presented herein.

In order to increase the effectiveness of the modified cells presented herein, it may be desirable to combine these compositions and methods with an agent effective in the treatment of the disease.

The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein, and one or more agents may be employed.

Diseases that may be treated or prevented include diseases caused by viruses, bacteria, yeast, parasites, protozoa, cancer cells and the like. Exemplary diseases that can be treated and/or prevented include, but are not limited, to infections of viral etiology such as HIV, influenza, herpes, viral hepatitis, Epstein Barr, polio, viral encephalitis, measles, chicken pox, papillomavirus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc. Preneoplastic or hyperplastic states which may be treated or prevented using the pharmaceutical composition (transduced cells, expression vector, expression construct, etc.) include but are not limited to preneoplastic or hyperplastic states such as colon polyps, Crohn's disease, ulcerative colitis, breast lesions and the like.

Cancers, including solid tumors, which may be treated using the cells include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases, including solid tumors, that may be treated using the therapeutic cells and other therapeutic cell activation system presented herein include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

Solid tumors from any tissue or organ may be treated using the present methods, including, for example, any tumor expressing a target antigen, for example, HLA-G, in the vasculature, for example, solid tumors present in, for example, lungs, bone, liver, prostate, or brain, and also, for example, in breast, ovary, bowel, testes, colon, pancreas, kidney, bladder, neuroendocrine system, soft tissue, boney mass, and lymphatic system. Other solid tumors that may be treated include, for example, glioblastoma, and malignant multiple myeloma.

Subjects may be given a zinc supplement to ensure that any zinc-dependent factors contained within a CIR or the cofactors expressed in a cell therapy product including a CIR have an adequate source of this ion to permit their full activity.

Also provided are methods of making the cells of the present disclosure. In some embodiments, such methods include transfecting or transducing cells with a nucleic acid or expression vector of the present disclosure (e.g., one encoding for a subject CIR). The term "transfection" is used to refer to the uptake of foreign DNA by a cell. A cell has been "transfected" when exogenous DNA has been introduced inside the cell membrane. A number of transfection techniques are generally known in the art. See, e.g., Sambrook et al. (2001) Molecular Cloning, a laboratory manual, 3$^{rd}$ edition, Cold Spring Harbor Laboratories, New York, Davis et al. (1995) Basic Methods in Molecular Biology, 2$^{nd}$ edition, McGraw-Hill, and Chu et al. (1981) Gene 13:197. Such techniques can be used to introduce one or more exogenous DNA moieties into suitable host cells. The term refers to both stable and transient uptake of the genetic material.

In some embodiments, a cell of the present disclosure is produced by transducing the cell with a viral vector encoding a CIR. In certain aspects, the polypeptide includes a CIR and the cell is a T cell, such that provided are methods of producing a CIR T cell. In some embodiments, such methods include activating a population of T cells (e.g., T cells obtained from an individual to which a CIR T cell therapy will be administered), stimulating the population of T cells to proliferate, and transducing the T cell with a viral vector encoding the polypeptide including the CIR. In some embodiments, an immune cell (e.g., T cells, NK cells, macrophages) is transduced with a retroviral vector, e.g., a gamma retroviral vector, or lentiviral vector, or AAV encoding a CIR. In certain aspects, the immune cell T cells are transduced with a lentiviral vector encoding the polypeptide. In certain aspects, the polypeptide includes a CIR and the cell is an NK cell, such that provided are methods of producing a CIR NK cell (e.g., by using a viral vector such as an AAV, lentiviral, or retroviral vector).

13. General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

The term "between" with reference to two values includes those two values e.g. the range "between" 10 mg and 20 mg encompasses inter alia 10, 15, and 20 mg.

Unless specifically stated, a method comprising a step of mixing two or more components does not require any specific order of mixing. Thus components can be mixed in any order. Where there are three components then two components can be combined with each other, and then the combination may be combined with the third component, etc.

The various steps of methods may be carried out at the same or different times, in the same or different geographical locations, e.g. countries, and by the same or different people or entities.

The term "pharmaceutically acceptable" refers to molecular entities and compositions that do not produce unwanted adverse, allergic, or other untoward reactions when administered to an animal or a human.

The extent of similarity between two sequences can be based on percent sequence identity. "Sequence identity" herein means the extent to which two nucleotide or amino acid sequences are invariant. "Sequence alignment" means the process of lining up two or more sequences to achieve maximal levels of identity for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using any of these programs, the settings may be selected that result in the highest sequence similarity.

14. Examples of Particular Nucleic Acid and Amino Acid Sequences

The following sections and tables include examples of polypeptide and nucleotide sequences coding for chimeric signaling polypeptides. It is understood that sequences of individual polypeptides provided in these examples, such as, for example, the truncated ILT2 and ILT4 polypeptides, costimulatory polypeptide cytoplasmic signaling regions, safety switches, may be used to construct other expression vectors that encode chimeric signaling polypeptides of the present embodiments.

Table 4 includes an example of the complete vector sequences for delivery of a γ-retrovirus containing HLA-G1 sequences together with a marker protein ΔCD19.

Tables 5-20 include only the transgenese expressed by the same example γ-retrovirus vector.

TABLE 4

Plasmid A: pNT101-SFG-HLAG1-T2A-ΔCD19

| Fragment | SEQ ID NO: | Nucleotide | SEQ ID NO: | Peptide |
|---|---|---|---|---|
| 5'LTR | 1 | | | |
| Linker | 2 | | | |
| MMLV psi | 3 | | | |
| LInker | 4 | | | |
| Gag | 5 | | | |
| Linker | | CCATATGG | | |
| Pol | 6 | | | |
| Linker | 7 | | | |
| HLA-G1 | 8 | | 9 | |
| Linker | | GGCAGTGGA | | GSG |
| T2A | 10 | | 11 | |
| ΔCD19 | 12 | | 13 | |
| STOP | | TAA | | STOP |
| 3' Viral vector sequence | 64 | | | |
| 3' UTR | 65 | | | |

TABLE 5

Plasmid B: pNT102-SFG-HLAG2-T2A-ΔCD19

| Fragment | SEQ ID NO: | Nucleotide | SEQ ID NO: | Peptide |
|---|---|---|---|---|
| HLA-G2 | 14 | | 15 | |
| Linker | | GGCAGTGGA | | GSG |
| T2A | 10 | | 11 | |
| ΔCD19 | 12 | | 13 | |
| STOP | | TAA | | STOP |

TABLE 6

Plasmid C: pNT103-SFG-HLAG3-T2A-ΔCD19

| Fragment | SEQ ID NO: | Nucleotide | SEQ ID NO: | Peptide |
|---|---|---|---|---|
| HLA-G3 | 16 | | 17 | |
| Linker | | GGCAGTGGA | | GSG |
| T2A | 10 | | 11 | |
| ΔCD19 | 12 | | 13 | |
| STOP | | TAA | | STOP |

TABLE 7

Plasmid D: pNT104-SFG-HLAG4-T2A-ΔCD19

| Fragment | SEQ ID NO: | Nucleotide | SEQ ID NO: | Peptide |
|---|---|---|---|---|
| HLA-G4 | 18 | | 19 | |
| Linker | | GGCAGTGGA | | GSG |
| T2A | 10 | | 11 | |
| ΔCD19 | 12 | | 13 | |
| STOP | | TAA | | STOP |

TABLE 8

Plasmid E: pNT105-SFG-HLAG5-T2A-ΔCD19

| Fragment | SEQ ID NO: | Nucleotide | SEQ ID NO: | Peptide |
|---|---|---|---|---|
| HLA-G5 | 20 | | 21 | |
| Linker | | GGCAGTGGA | | GSG |
| T2A | 10 | | 11 | |
| ΔCD19 | 12 | | 13 | |
| STOP | | TAA | | STOP |

TABLE 9

Plasmid F: pNT106-SFG-HLAG5C42S-T2A-ΔCD19

| Fragment | SEQ ID NO: | Nucleotide | SEQ ID NO: | Peptide |
|---|---|---|---|---|
| HLA-G5 (C42S) | 22 | | 23 | |
| Linker | | GGCAGTGGA | | GSG |
| T2A | 10 | | 11 | |
| ΔCD19 | 12 | | 13 | |
| STOP | | TAA | | STOP |

TABLE 10

Plasmid G: pNT107-SFG-HLAG1C42S-T2A-ΔCD19

| Fragment | SEQ ID NO: | Nucleotide | SEQ ID NO: | Peptide |
|---|---|---|---|---|
| HLA-G1 (C42S) | 24 | | 25 | |
| Linker | | GGCAGTGGA | | GSG |
| T2A | 10 | | 11 | |
| ΔCD19 | 12 | | 13 | |
| STOP | | TAA | | STOP |

TABLE 11

Plasmid H: pNT108-SFG-HLAG1C42SC147S-T2A-ΔCD19

| Fragment | SEQ ID NO: Nucleotide | Nucleotide | SEQ ID NO: Peptide | Peptide |
|---|---|---|---|---|
| HLA-G1 (C42S/C147S) | 44 | | 45 | |
| Linker | | GGCAGTGGA | | GSG |
| T2A | 10 | | 11 | |
| ΔCD19 | 12 | | 13 | |
| STOP | | TAA | | STOP |

TABLE 12

Plasmid I: pNT109-SFG-HLAG1C147S-T2A-ΔCD19

| Fragment | SEQ ID NO: Nucleotide | Nucleotide | SEQ ID NO: Peptide | Peptide |
|---|---|---|---|---|
| HLA-G1 (C147S) | 26 | | 27 | |
| Linker | | GGCAGTGGA | | GSG |
| T2A | 10 | | 11 | |
| ΔCD19 | 12 | | 13 | |
| STOP | | TAA | | STOP |

TABLE 13A

Plasmid K: pNT-110 SFG-ILT2-T2A-ΔCD19

| Fragment | SEQ ID NO: Nucleotide | Nucleotide | SEQ ID NO: Peptide | Peptide |
|---|---|---|---|---|
| ILT2 | 28 | | 29 | |
| Linker | | GGCAGTGGA | | GSG |
| T2A | 10 | | 11 | |
| ΔCD19 | 12 | | 13 | |
| STOP | | TAA | | STOP |

TABLE 13B

Plasmid K: pNT-110 SFG-ILT2-T2A-ΔCD19 [ILT2 FL; see FIG. 6A]

| Fragment | SEQ ID NO: Nucleotide | Nucleotide | SEQ ID NO: Peptide | Peptide |
|---|---|---|---|---|
| ILT2 | 77 | | 78 | |
| Linker | | GGCTCTGGA | | GSG |
| T2A | 79 | | 11 | |
| ΔCD19 | 80 | | 13 | |
| STOP | | TGA | | STOP |

*note: This table is similar to the one above, but the nucleotide sequences were codon-optimized. The sequences in this table are those that were used in the Examples section. The codon-optimized ILT2 sequence also inserted a QT amino acid sequence into the ILT2 protein (for purposes of cloning efficiency).

TABLE 14

Plasmid L: pNT-111 SFG-ILT2.ζ-T2A-ΔCD19

| Fragment | SEQ ID NO: Nucleotide | Nucleotide | SEQ ID NO: Peptide | Peptide |
|---|---|---|---|---|
| ILT2 (D1-D4-TM) | 30 | | 31 | |
| Linker | | GTCGAC | | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 15A

Plasmid M: pNT-112 SFG-ILT2.BB.ζ-T2A-ΔCD19

| Fragment | SEQ ID NO: Nucleotide | Nucleotide | SEQ ID NO: Peptide | Peptide |
|---|---|---|---|---|
| ILT2 (D1-D4-TM) | 30 | | 31 | |
| Linker | | GGATCC | | GS |
| 41BB | 34 | | 35 | |
| Linker | | GTCGAC | | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 15B

Plasmid M: pNT-112 SFG-ILT2.BB.ζ-T2A-ΔCD19
[ILT2 CIR1; see FIG. 6A]

| Fragment | SEQ ID NO: | Nucleotide | SEQ ID NO: | Peptide |
|---|---|---|---|---|
| ILT2 (D1-D4-TM) | 81 | | 82 | |
| Linker | | GGATCC | | GS |
| 41BB | 83 | | 35 | |
| Linker | | GTCGAC | | VD |
| CD3ζ | 32 | | 33 | |
| Linker | | GGCTCTGGA | | GSG |
| T2A | 79 | | 11 | |
| ΔCD19 | 80 | | 13 | |
| STOP | | TGA | | STOP |

*note: This table is similar to the one above, but the nucleotide sequences were optimized. The sequences in this table are those that were used in the Example section. The codon-optimized ILT2 sequence also inserted a QT amino acid sec into the ILT2 protein sequences (for purposes of cloning efficiency)

TABLE 16A

Plasmid N: pNT-113 SFG-ILT2D1D2STM.BB.ζ-T2A-ΔCD19

| Fragment | SEQ ID NO: | Nucleotide | SEQ ID NO: | Peptide |
|---|---|---|---|---|
| ILT2 (D1-D2) | 36 | | 37 | |
| Linker | | AGCGGCCGC | | SGR |
| ILT2 StalkTM | 38 | | 39 | |
| Linker | | GGATCC | | GS |
| 41BB | 34 | | 35 | |
| Linker | | GTCGAC | | VD |
| CD3ζ | 32 | | 33 | |
| Linker | 66 | CCGCGGGGCAGTGGA | 67 | PRGSG |
| T2A | 10 | | 11 | |
| ΔCD19 | 12 | | 13 | |
| STOP | | TAA | | STOP |

TABLE 16B

Plasmid N: pNT-113 SFG-ILT2D1D2STM.BB.ζ-T2A-ΔCD19
[ILT2 CIR2; see FIG. 6A]

| Fragment | SEQ ID NO: | Nucleotide | SEQ ID NO: | Peptide |
|---|---|---|---|---|
| ILT2 (D1-D2) | 84 | | 37 | |
| Linker | | AGCGGCCGC | | SGR |
| ILT2 | 85 | | 39 | |
| StalkTM | | | | |
| Linker | | GGATCC | | GS |
| 41BB | 83 | | 35 | |
| Linker | | GTCGAC | | VD |
| CD3ζ | 32 | | 33 | |
| Linker | 66 | CCGCGGGGCAGTGGA | 67 | PRGSG |
| T2A | 79 | | 11 | |
| ΔCD19 | 80 | | 13 | |
| STOP | | TGA | | STOP |

*note: This table is similar to the one above, but the nucleotide sequences were codon-optimized. The sequences in this table are those that were used in the Examples section

TABLE 17

Plasmid O: pNT-114 SFG-ILT2D1D2.Q.8STM.BB.ζ-T2A-ΔCD19

| Fragment | SEQ ID NO: | Nucleotide | SEQ ID NO: | Peptide |
|---|---|---|---|---|
| ILT2 (D1-D2) | 36 | | 37 | |
| Linker | | AGCGGCCGC | | SGR |
| Q epitope | 40 | | 41 | |
| CD8StalkTM | 42 | | 43 | |
| Linker | | GGATCC | | GS |
| 41BB | 34 | | 35 | |
| Linker | | GTCGAC | | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 18

Plasmid P: pNT-115 SFG-ILT2D1D2.Q.28STM.CD28.ζ-T2A-ΔCD19

| Fragment | SEQ ID NO: | Nucleotide | SEQ ID NO: | Peptide |
|---|---|---|---|---|
| ILT2 (D1-D2) | 36 | | 37 | |
| Linker | | AGCGGCCGC | | SGR |
| Q epitope | 40 | | 41 | |
| CD28Stalk TM | 46 | | 47 | |
| Linker | | GGATCC | | GS |
| CD28 | 48 | | 49 | |
| Linker | | GTCGAC | | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 19

Plasmid R: pNT-116 SFG-ILT2D1D2.Q.CH2CH3.8TM.BB.ζ-T2A-ΔCD19

| Fragment | SEQ ID NO: | Nucleotide | SEQ ID NO: | Peptide |
|---|---|---|---|---|
| ILT2 (D1-D2) | 36 | | 37 | |
| Linker | | AGCGGCCGC | | SGR |
| Q epitope | 40 | | 41 | |
| CH2CH3 | 50 | | 51 | |
| CD28TM | | | | |
| Linker | | GGATCC | | GS |
| 41BB | 34 | | 35 | |
| Linker | | GTCGAC | | VD |
| CD3ζ | 32 | | 33 | |

TABLE 20A

Plasmid S: pNT-117 SFG-ILT2D1D2.CD8STM.BB.ζ-T2A-ΔCD19

| Fragment | SEQ ID NO: | Nucleotide | SEQ ID NO: | Peptide |
|---|---|---|---|---|
| ILT2 (D1-D2) | 36 | | 37 | |
| Linker | | AGCGGCCGC | | SGR |
| CD8StalkTM | 42 | | 43 | |
| Linker | | GGATCC | | GS |
| 41BB | 34 | | 35 | |
| Linker | | GTCGAC | | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 20B

Plasmid S: pNT-117 SFG-ILT2D1D2.CD8STM.BB.ζ-T2A-ΔCD19
[ILT2 CIR4; see FIG. 6A]

| Fragment | SEQ ID NO: | Nucleotide | SEQ ID NO: | Peptide |
|---|---|---|---|---|
| ILT2 (D1-D2) | 84 | | 37 | |
| Linker | | AGCGGCCGC | | SGR |
| CD8StalkTM | 86 | | 43 | |
| Linker | | GGATCC | | GS |
| 41BB | 83 | | 35 | |
| Linker | | GTCGAC | | VD |
| CD3ζ | 32 | | 33 | |
| Linker | | GGCAGTGGA | | GSG |
| T2A | 79 | | 11 | |
| ΔCD19 | 80 | | 13 | |
| STOP | | TGA | | STOP |

*note: This table is similar to the one above, but the nucleotide sequences were codon-optimized. The sequences in this table are those that were used in the Examples section

TABLE 21A

Plasmid T: pNT-118 SFG-ILT4-T2A-ΔCD19

| Fragment | SEQ ID NO: | Nucleotide | SEQ ID NO: | Peptide |
|---|---|---|---|---|
| ILT4 | 52 | | 53 | |
| Linker | | GGCAGTGGA | | GSG |
| T2A | 10 | | 11 | |

TABLE 21A-continued

Plasmid T: pNT-118 SFG-ILT4-T2A-ΔCD19

| Fragment | SEQ ID NO: | Nucleotide | SEQ ID NO: | Peptide |
|---|---|---|---|---|
| ΔCD19 | 12 | | 13 | |
| STOP | | TAA | | STOP |

TABLE 21B

Plasmid T: pNT-118 SFG-ILT4-T2A-ΔCD19
[ILT4 FL; see FIG. 6A]

| Fragment | SEQ ID NO: | Nucleotide | SEQ ID NO: | Peptide |
|---|---|---|---|---|
| ILT4 | 87 | | 88 | |
| Linker | | GGCTCTGGA | | GSG |
| T2A | 79 | | 11 | |
| ΔCD19 | 80 | | 13 | |
| STOP | | TGA | | STOP |

*note: This table is similar to the one above, but the nucleotide sequences were codon-optimized. The sequences in this table are those that were used in the Examples section. The codon-optimized ILT4 sequence also inserted a QT amino acid sequence into the ILT4 protein (for purposes of cloning efficiency).

TABLE 22

Plasmid U: pNT-119 SFG-ILT4.ζ-T2A-ΔCD19

| Fragment | SEQ ID NO: | Nucleotide | SEQ ID NO: | Peptide |
|---|---|---|---|---|
| ILT4 (D1-D4-TM) | 54 | | 55 | |
| Linker | 35 | GTCGAC | 36 | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 23A

Plasmid V: pNT-120 SFG-ILT4.BB.ζ-T2A-ΔCD19

| Fragment | SEQ ID NO: | Nucleotide | SEQ ID NO: | Peptide |
|---|---|---|---|---|
| ILT4 (D1-D4-TM) | 54 | | 55 | |
| Linker | | GGATCC | | GS |
| 41BB | 34 | | 35 | |
| Linker | | GTCGAC | | VD |
| CD3ζ | 32 | | 33 | |

TABLE 23A-continued

Plasmid V: pNT-120 SFG-ILT4.BB.ζ-T2A-ΔCD19

| Fragment | SEQ ID NO: | Nucleotide | SEQ ID NO: | Peptide |
|---|---|---|---|---|
| Linker | | GGCAGTGGA | | GSG |
| T2A | 10 | | 11 | |
| ΔCD19 | 12 | | 13 | |
| STOP | | TAA | | STOP |

TABLE 23B

Plasmid V: pNT-120 SFG-ILT4.BB.ζ-T2A-ΔCD19
[ILT4 CIR1; see FIG. 6A]

| Fragment | SEQ ID NO: | Nucleotide | SEQ ID NO: | Peptide |
|---|---|---|---|---|
| ILT4 (D1-D4-TM) | 89 | | 90 | |
| Linker | | GGATCC | | GS |
| 41BB | 83 | | 35 | |
| Linker | | GTCGAC | | VD |
| CD3ζ | 32 | | 33 | |
| Linker | | GGCAGTGGA | | GSG |
| T2A | 79 | | 11 | |
| ΔCD19 | 80 | | 13 | |
| STOP | | TGA | | STOP |

*note: This table is similar to the one above, but the nucleotide sequences were codon-optimized. The sequences in this table are those that were used in the Examples section. The codon-optimized ILT4 sequence also inserted a QT amino acid sequence into the ILT4 protein sequences (for purposes of cloning efficiency).

TABLE 24A

Plasmid W: pNT-121 SFG-ILT4D1D2STM.BB.ζ-T2A-ΔCD19

| Fragment | SEQ ID NO: | Nucleotide | SEQ ID NO: | Peptide |
|---|---|---|---|---|
| ILT4 (D1-D2) | 56 | | 57 | |
| Linker | | AGCGGCCGC | | SGR |
| ILT4 StalkTM | 58 | | 59 | |
| Linker | | GGATCC | | GS |
| 41BB | 34 | | 35 | |
| Linker | | GTCGAC | | VD |
| CD3ζ | 32 | | 33 | |
| Linker | 66 | CCGCGGGGCAGTGGA | 67 | PRGSG |
| T2A | 10 | | 11 | |

TABLE 24A-continued

Plasmid W: pNT-121 SFG-ILT4D1D2STM.BB.ζ-T2A-ΔCD19

| Fragment | SEQ ID NO: Nucleotide | SEQ ID NO: Peptide |
|---|---|---|
| ΔCD19 | 12 | 13 |
| STOP | TAA | STOP |

TABLE 24B

Plasmid W: pNT-121 SFG-ILT4D1D2STM.BB.ζ-T2A-ΔCD19 [ILT4 CIR2; see FIG. 6A]

| Fragment | SEQ ID NO: Nucleotide | SEQ ID NO: Peptide |
|---|---|---|
| ILT4 (D1-D2) | 91 | 57 |
| Linker | AGCGGCCGC | SGR |
| ILT4 StalkTM | 58 | 59 |
| Linker | GGATCC | GS |
| 41BB | 34 | 35 |
| Linker | GTCGAC | VD |
| CD3ζ | 32 | 33 |
| Linker | CCGCGGGGCAGTGGA | PRGSG |
| T2A | 79 | 11 |
| ΔCD19 | 80 | 13 |
| STOP | TGA | STOP |

*note: This table is similar to the one above, but the nucleotide sequences were codon-optimized. The sequences in this table are those that were used in the Examples section

TABLE 25

Plasmid X: pNT-122 SFG-ILT4D1D2.Q.8STM.BB.ζ-T2A-ΔCD19

| Fragment | SEQ ID NO: Nucleotide | SEQ ID NO: Peptide |
|---|---|---|
| ILT4 (D1-D2) | 56 | 57 |
| Linker | AGCGGCCGC | SGR |
| Q epitope | 40 | 41 |
| CD8StalkTM | 42 | 43 |
| Linker | GGATCC | GS |
| 41BB | 34 | 35 |
| Linker | GTCGAC | VD |
| CD3ζ | 32 | 33 |
| Linker | GGCAGTGGA | GSG |

TABLE 25-continued

Plasmid X: pNT-122 SFG-ILT4D1D2.Q.8STM.BB.ζ-T2A-ΔCD19

| Fragment | SEQ ID NO: Nucleotide | SEQ ID NO: Peptide |
|---|---|---|
| T2A | 10 | 11 |
| ΔCD19 | 12 | 13 |
| STOP | TAA | STOP |

TABLE 26

Plasmid Y: pNT-123 SFG-ILT4D1D2.Q.28STM.CD28.ζ-T2A-ΔCD19

| Fragment | SEQ ID NO: Nucleotide | SEQ ID NO: Peptide |
|---|---|---|
| ILT4 (D1-D2) | 56 | 57 |
| Linker | AGCGGCCGC | SGR |
| Q epitope | 40 | 41 |
| CD28StalkTM | 46 | 47 |
| Linker | GGATCC | GS |
| CD28 | 48 | 49 |
| Linker | GTCGAC | VD |
| CD3ζ | 32 | 33 |
| Linker | GGCAGTGGA | GSG |
| T2A | 10 | 11 |
| ΔCD19 | 12 | 13 |
| STOP | TAA | STOP |

TABLE 27

Plasmid Z: pNT-124 SFG-ILT4D1D2.Q.CH2CH3.8TM.BB.ζ-T2A-ΔCD19

| Fragment | SEQ ID NO: Nucleotide | SEQ ID NO: Peptide |
|---|---|---|
| ILT4 (D1-D2) | 56 | 57 |
| Linker | AGCGGCCGC | SGR |
| Q epitope | 40 | 41 |
| CH2CH3 | 50 | 51 |
| CD28TM | | |
| Linker | GGATCC | GS |
| 41BB | 34 | 35 |
| Linker | GTCGAC | VD |
| CD3ζ | 32 | 33 |

TABLE 28A

Plasmid AA: pNT-124 SFG-ILT4D1D2.CD8STM.BB.ζ-T2A-ΔCD19

| Fragment | SEQ ID NO: | Nucleotide | SEQ ID NO: | Peptide |
|---|---|---|---|---|
| ILT4 (D1-D2) | 56 | | 57 | |
| Linker | | AGCGGCCGC | | SGR |
| CD8StalkTM | 42 | | 43 | |
| Linker | | GGATCC | | GS |
| 41BB | 34 | | 35 | |
| Linker | | GTCGAC | | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 28B

Plasmid AA: pNT-124 SFG-ILT4D1D2.CD8STM.BB.ζ-T2A-ΔCD19 [ILT4 CIR4; see FIG. 6A]

| Fragment | SEQ ID NO: | Nucleotide | SEQ ID NO: | Peptide |
|---|---|---|---|---|
| ILT4 (D1-D2) | 91 | | 57 | |
| Linker | | AGCGGCCGC | | SGR |
| CD8StalkTM | 86 | | 43 | |
| Linker | | GGATCC | | GS |
| 41BB | 83 | | 35 | |
| Linker | | GTCGAC | | VD |
| CD3ζ | 32 | | 33 | |
| Linker | | GGCAGTGGA | | GSG |
| T2A | 79 | | 11 | |
| ΔCD19 | 80 | | 13 | |
| STOP | | TGA | | STOP |

*note: This table is similar to the one above, but the nucleotide sequences were codon-optimized. The sequences in this table are those that were used in the Examples section

TABLE 29

Plasmid U: pNT-119 SFG-ILT4Y394A.ζ-T2A-ΔCD19

| Fragment | SEQ ID NO: | Nucleotide | SEQ ID NO: | Peptide |
|---|---|---|---|---|
| ILT4 Y394A (D1-D4-TM) | 60 | | 61 | |
| Linker | 35 | GTCGAC | 36 | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 30

Plasmid AC: pNT-126 SFG-ILT4Y394A.BB.ζ-T2A-ΔCD19

| Fragment | SEQ ID NO: | Nucleotide | SEQ ID NO: | Peptide |
|---|---|---|---|---|
| ILT4 Y394A (D1-D4-TM) | 60 | | 61 | |
| Linker | | GGATCC | | GS |
| 41BB | 34 | | 35 | |
| Linker | | GTCGAC | | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 31

Plasmid AD: pNT-128 SFG-ILT4D1D2Y96A.STM.BB.ζ-T2A-ΔCD19

| Fragment | SEQ ID NO: | Nucleotide | SEQ ID NO: | Peptide |
|---|---|---|---|---|
| ILT4 (D1-D2) | 62 | | 63 | |
| Linker | | AGCGGCCGC | | SGR |
| ILT4 StalkTM | 58 | | 59 | |
| Linker | | GGATCC | | GS |
| 41BB | 34 | | 35 | |
| Linker | | GTCGAC | | VD |
| CD3ζ | 32 | | 33 | |

TABLE 31-continued

Plasmid AD: pNT-128 SFG-ILT4D1D2Y96A.STM.BB.ζ-T2A-ΔCD19

| Fragment | SEQ ID NO: | Nucleotide | SEQ ID NO: | Peptide |
|---|---|---|---|---|
| Linker | 66 | | 67 | |
| T2A | 10 | | 11 | |
| ΔCD19 | 12 | | 13 | |
| STOP | | TAA | | STOP |

TABLE 32

Plasmid AE: pNT-129 SFG-ILT4D1D2Y96A.Q.8STM.BB.ζ-T2A-ΔCD19

| Fragment | SEQ ID NO: | Nucleotide | SEQ ID NO: | Peptide |
|---|---|---|---|---|
| ILT4 (D1-D2) | 62 | | 63 | |
| Linker | | AGCGGCCGC | | SGR |
| Q epitope | 40 | | 41 | |
| CD8StalkTM | 42 | | 43 | |
| Linker | | GGATCC | | GS |
| 41BB | 34 | | 35 | |
| Linker | | GTCGAC | | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 33

Plasmid AF: pNT-130 SFG-ILT4D1D2Y96A.Q.28STM.CD28.ζ-T2A-ΔCD19

| Fragment | SEQ ID NO: | Nucleotide | SEQ ID NO: | Peptide |
|---|---|---|---|---|
| ILT4 (D1-D2) | 62 | | 63 | |
| Linker | | AGCGGCCGC | | SGR |
| Q epitope | 40 | | 41 | |
| CD28StalkTM | 46 | | 47 | |
| Linker | | GGATCC | | GS |
| CD28 | 48 | | 49 | |
| Linker | | GTCGAC | | VD |
| CD3ζ | 32 | | 33 | |

TABLE 33-continued

Plasmid AF: pNT-130 SFG-ILT4D1D2Y96A.Q.28STM.CD28.ζ-T2A-ΔCD19

| Fragment | SEQ ID NO: | Nucleotide | SEQ ID NO: | Peptide |
|---|---|---|---|---|
| Linker | | GGCAGTGGA | | GSG |
| T2A | 10 | | 11 | |
| ΔCD19 | 12 | | 13 | |
| STOP | | TAA | | STOP |

TABLE 34

Plasmid AG: pNT-131 SFG-ILT4D1D2Y96A.Q.CH2CH3.8TM.BB.ζ-T2A-ΔCD19

| Fragment | SEQ ID NO: | Nucleotide | SEQ ID NO: | Peptide |
|---|---|---|---|---|
| ILT4 (D1-D2) | 62 | | 63 | |
| Linker | | AGCGGCCGC | | SGR |
| Q epitope | 40 | | 41 | |
| CH2CH3 CD28TM | 50 | | 51 | |
| Linker | | GGATCC | | GS |
| 41BB | 34 | | 35 | |
| Linker | | GTCGAC | | VD |
| CD3ζ | 32 | | 33 | |

TABLE 35

Plasmid AH: pNT-132 SFG-ILT4D1D2Y96A.CD8STM.BB.ζ-T2A-ΔCD19

| Fragment | SEQ ID NO: | Nucleotide | SEQ ID NO: | Peptide |
|---|---|---|---|---|
| ILT4 (D1-D2) | 62 | | 63 | |
| Linker | | AGCGGCCGC | | SGR |
| CD8StalkTM | 42 | | 43 | |
| Linker | | GGATCC | | GS |
| 41BB | 34 | | 35 | |
| Linker | | GTCGAC | | VD |
| CD3ζ | 32 | | 33 | |
| Linker | | GGCAGTGGA | | GSG |
| T2A | 10 | | 11 | |
| ΔCD19 | 12 | | 13 | |
| STOP | | TAA | | STOP |

TABLE 36 pNT133-pSFG-ILT2(D1-D4).CD8StalkTM.BB.z.T2A-dCD19
[ILT2 CIR3; see FIG. 6A]

| Fragment | SEQ ID NO: | Nucleotide | SEQ ID NO: | Peptide |
|---|---|---|---|---|
| ILT2 (D1-D4) | 93 | | 94 | |
| Linker | | AGCGGCCGC | | SGR |
| CD8StalkTM | 86 | | 43 | |
| Linker | | GGATCC | | GS |
| 41BB | 83 | | 35 | |
| Linker | | GTCGAC | | VD |
| CD3ζ | 32 | | 33 | |
| Linker | | GGCAGTGGA | | GSG |
| T2A | 79 | | 11 | |
| ΔCD19 | 80 | | 13 | |
| STOP | | TGA | | STOP |

TABLE 37 pNT134-pSFG-ILT4(D1-D4).CD8StalkTM.BB.z.T2A-dCD19
[ILT4 CIR3; see FIG. 6A]

| Fragment | SEQ ID NO: | Nucleotide | SEQ ID NO: | Peptide |
|---|---|---|---|---|
| ILT4 (D1-D4) | 95 | | 96 | |
| Linker | | AGCGGCCGC | | SGR |
| CD8StalkTM | 86 | | 43 | |
| Linker | | GGATCC | | GS |
| 41BB | 83 | | 35 | |
| Linker | | GTCGAC | | VD |
| CD3ζ | 32 | | 33 | |
| Linker | | GGCAGTGGA | | GSG |
| T2A | 79 | | 11 | |
| ΔCD19 | 80 | | 13 | |
| STOP | | TGA | | STOP |

TABLE 38 pNT138 SFG-ILT4(D1-D2).CH2CH3(4-2NQ).CD8TM.BB.z.T2A-dCD19
[ILT4 CIR6; see FIG. 6A]

| Fragment | SEQ ID NO: | Nucleotide | SEQ ID NO: | Peptide |
|---|---|---|---|---|
| ILT4 (D1-D2) | 91 | | 57 | |
| Linker | | AGCGGCCGC | | SGR |
| IgG4 CH2CH3 | 97 | | 98 | |
| CD8a TM | 99 | | 100 | |
| Linker | | GGATCC | | GS |
| 41BB | 83 | | 35 | |
| Linker | | GTCGAC | | VD |
| CD3ζ | 32 | | 33 | |
| Linker | 66 | CCGCGGGGCAGTGGA | 67 | PRGSG |
| T2A | 79 | | 11 | |
| ΔCD19 | 80 | | 13 | |
| STOP | | TGA | | STOP |

TABLE 39 pNT139 SFG-ILT4(D1-D2).CH3.CD8tm.BB.z.T2A-dCD19
[ILT4 CIR7; see FIG. 6A]

| Fragment | SEQ ID NO: | Nucleotide | SEQ ID NO: | Peptide |
|---|---|---|---|---|
| ILT4 (D1-D2) | 91 | | 57 | |
| Linker | | AGCGGCCGC | | SGR |
| IgG4 CH3 | 101 | | 102 | |
| CD8a TM | 99 | | 100 | |
| Linker | | GGATCC | | GS |
| 41BB | 83 | | 35 | |
| Linker | | GTCGAC | | VD |
| CD3ζ | 32 | | 33 | |
| Linker | 66 | CCGCGGGGCAGTGGA | 67 | PRGSG |
| T2A | 79 | | 11 | |
| ΔCD19 | 80 | | 13 | |
| STOP | | TGA | | STOP |

TABLE 40 pNT-159 SFG-ILT4(D1-D2).CH2CH3(4-2NQ)s.
CD28tm.BB.z.T2A-dCD19
[ILT4 CIR8; see FIG. 6A]

| Fragment | SEQ ID NO: Nucleotide | Nucleotide | SEQ ID NO: Peptide | Peptide |
|---|---|---|---|---|
| ILT4 (D1-D2) | 91 | | 57 | |
| Linker | | AGCGGCCGC | | SGR |
| IgG4 CH2CH3 | 97 | | 98 | |
| CD28 TM | 103 | | 104 | |
| Linker | | GGATCC | | GS |
| 41BB | 83 | | 35 | |
| Linker | | GTCGAC | | VD |
| CD3ζ | 32 | | 33 | |
| Linker | 66 | CCGCGGGGCAGTGGA | 67 | PRGSG |
| T2A | 79 | | 11 | |
| ΔCD19 | 80 | | 13 | |
| STOP | | TGA | | STOP |

TABLE 41 pNT-160 SFG-ILT4(D1-D2).CH3s.CD28tm.BB.z.T2A-dCD19
[ILT4 CIR9; see FIG. 6A]

| Fragment | SEQ ID NO: Nucleotide | Nucleotide | SEQ ID NO: Peptide | Peptide |
|---|---|---|---|---|
| ILT4 (D1-D2) | 91 | | 57 | |
| Linker | | AGCGGCCGC | | SGR |
| IgG4 CH3 | 101 | | 102 | |
| CD28 TM | 103 | | 104 | |
| Linker | | GGATCC | | GS |
| 41BB | 83 | | 35 | |
| Linker | | GTCGAC | | VD |
| CD3ζ | 32 | | 33 | |
| Linker | 66 | CCGCGGGGCAGTGGA | 67 | PRGSG |
| T2A | 79 | | 11 | |
| ΔCD19 | 80 | | 13 | |
| STOP | | TGA | | STOP |

TABLE 42 pNT-158 SFG-ILT4(D1-D2).CD28s.CD28tm.BB.z.T2A-dCD19
[ILT4 CIR10; see FIG. 6A]

| Fragment | SEQ ID NO: Nucleotide | Nucleotide | SEQ ID NO: Peptide | Peptide |
|---|---|---|---|---|
| ILT4 (D1-D2) | 91 | | 57 | |
| Linker | | AGCGGCCGC | | SGR |
| CD28 stalk | 105 | | 106 | |
| CD28 TM | 103 | | 104 | |
| Linker | | GGATCC | | GS |
| 41BB | 83 | | 35 | |
| Linker | | GTCGAC | | VD |
| CD3ζ | 32 | | 33 | |
| Linker | 66 | CCGCGGGGCAGTGGA | 67 | PRGSG |
| T2A | 79 | | 11 | |
| ΔCD19 | 80 | | 13 | |
| STOP | | TGA | | STOP |

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below (see Set A and Set B). As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the invention.

Set A
1. A composition wherein genetically modified cells express a chimeric receptor protein specifically a targeting a protein or carbohydrate with a binding domain that is not derived from an antibody, VhH domain or synthetically derived polypeptide.
2. The composition of 1, wherein the chimeric receptor protein utilizes a recognition or binding domain to target HLA-G that is not derived from an antibody, VhH domain or synthetically derived polypeptide.
3. The composition of 1 or 2, wherein the chimeric receptor protein utilizes human receptor proteins that naturally recognize a target protein including HLA-G as part of their biological mechanism of action.
4. The composition of 3, wherein the chimeric receptor protein utilizes ILT2 derived from human or simian sequences.
5. The composition of 3, wherein the chimeric receptor protein utilizes ILT4 derived from human or simian sequences.
6. The composition of 4 wherein the chimeric receptor protein utilizes a natural polymorphic form of ILT2 derived from human or simian sequences.

7. The composition of 5 wherein the chimeric receptor protein utilizes a natural polymorphic form of ILT4 derived from human or simian sequences.
8. The composition of 4 and 6, wherein the chimeric receptor protein utilizes the D1 and D2 domains derived from ILT2.
9. The composition of 5 and 7, wherein the chimeric receptor protein utilizes the D1 and D2 domains derived from ILT4.
10. The composition of any preceding wherein the D1 or D2 domains of ILT2 or ILT4 are mutated to encode alternative amino acids with the purpose of reducing the affinity of proteins other than HLA-G while retaining affinity for HLA-G sufficient for activation of the chimeric receptor.
11. The composition of 10 where the mutations create amino acid substitutions at positions corresponding to amino acids 96 or 394 in ILT4.
12. The composition of any preceding claim, wherein the genetically modified cells further express a safety switch.
13. The composition of 12, wherein the safety switch is inducible.
14. The composition of 12, wherein the safety switch is triggered by rimiducid or by rapamycin or an analog of rapamycin.
15. The composition of any preceding claim, wherein the genetically modified cells further express a second chimeric antigen receptor.
16. The composition of any of 1-11, wherein the genetically modified cells further express a cytoplasmic signalling domain that drives activation of cytotoxicity to NK cells or T cells as a fused element with the compositions of 1-11.
17. The composition of 16, wherein the fused cytotoxic signalling elements contain ITAM sequences.
18. The composition of 16 or 17, wherein the fused signalling elements are derived from CD3ζ, DAP10 or DAP12.
19. The composition of any preceding claim, wherein the genetically modified cells further express a costimulatory polypeptide as part of the chimeric receptor.
20. The composition of any preceding claim, wherein the genetically modified cells further express a costimulatory polypeptide as a unit separated from the chimeric receptor protein.
21. The composition of 19 and 20, wherein the costimulatory polypeptide contains signalling elements derived from 4-11BB, OX40, ICOS, CD28, CD27, MyD88, IL-1Rα, HVEM, TRANCE, IL-1 Rβ, CD70, IL-18Rα, CD40, IL-18Rβ, IL-33Rα, CD30 or IL-33Rβ.
22. The composition of any preceding claim, wherein the genetically modified cells are (i) T cells (ii) NK cells (iii) iNKT cells or (iv) macrophages.
23. A method of treating a human subject, comprising administering to the patient a composition of any preceding claim.
24. A method of treating a human subject, comprising administering to the patient a composition of any preceding when the subject is a cancer patient.
25. An expression construct comprising a polynucleotide encoding the chimeric receptor protein of any one of 1-21.
26. A vector comprising the expression construct of 25 wherein the vector is a retroviral vector, a lentiviral vector or a plasmid vector.

Set B
1. A chimeric receptor protein, comprising:
    (a) a targeting region, that targets HLA-G, comprising a D1-D2 extracellular domain of immunoglulin-like transcript 2 (ILT2) or immunoglulin-like transcript 4 (ILT4);
    (b) a transmembrane (TM) region, comprising a transmembrane amino acid sequence; and
    (c) an intracellular domain (ICD), comprising a signaling region capable of transducing a signal, upon binding of said targeting region to HLA-G, into the interior of an immune effector cell to elicit effector cell function.
2. The chimeric receptor protein of 1, wherein the targeting region comprises an amino acid mutation at a position corresponding to Y96 of the ILT4 amnio acid sequence set forth in SEQ ID NO: 57 or Y96 of the ILT2 amnio acid sequence set forth in SEQ ID NO: 31.
3. The chimeric receptor protein of 1 or 2, wherein the D1-D2 extracellular domain is an ILT2 D1-D2 extracellular domain.
4. The chimeric receptor protein of 1 or 2, wherein the D1-D2 extracellular domain is an ILT4 D1-D2 extracellular domain.
5. The chimeric receptor protein of any one of 1-4, wherein the targeting region comprises a D3-D4 extracellular domain of ILT2 or ILT4.
6. The chimeric receptor protein of 5, wherein the targeting region comprises an amino acid mutation at a position corresponding to Y394 of the ILT4 amnio acid sequence set forth in SEQ ID NO: 55 or Y395 of the ILT2 amnio acid sequence set forth in SEQ ID NO: 31.
7. The chimeric receptor protein of any one of 1-4, wherein the targeting region lacks an ILT2 or ILT4 D3-D4 extracellular domain.
8. The chimeric receptor protein of 5, comprising a stalk domain.
9. The chimeric receptor protein of 8, wherein the stalk domain comprises a ILT2, ILT4, CD28, CH2/CH3, CH3, or CD8 stalk domain.
10. The chimeric receptor protein of any one of 1-9, wherein TM domain is an ILT2, ILT4, CD28, or CD8 TM domain.
11. The chimeric receptor protein of any one of 1-10, wherein said signaling region comprises immunoreceptor tyrosine-based activation motifs (ITAMs).
12. The chimeric receptor protein of any one of 1-10, wherein said signaling region comprises a CD3ζ signaling domain, a DAP10 signaling domain, a DAP12 signaling domain, or any combination thereof.
13. The chimeric receptor protein of any one of 1-10, wherein said signaling region comprises a CD3ζ signaling domain.
14. The chimeric receptor protein of any one of 1-13, wherein the ICD further comprises a costimulatory region comprising at least one costimulatory domain.
15. The chimeric receptor protein of 14, wherein said at least one costimulatory domain comprises a CD28 costimulatory domain.
16. The chimeric receptor protein of 14 or 15, wherein said at least one costimulatory domain comprises a 4-1 BB costimulatory domain.
17. The chimeric receptor protein of 14, wherein said at least one costimulatory domain comprises a 4-1BB, OX40, CD28, ICOS, RANK, DAP10, DAP12, CD27, MyD88, IL-1 Rα, HVEM, TRANCE, IL-1 Rβ, CD70, IL-18Rα, CD40, IL-18Rβ, IL-33Rα, CD30, or IL-33Rβ costimulatory domain, or any combination thereof.

18. The chimeric receptor protein of 1, wherein:
    the D1-D2 extracellular domain is an ILT2 D1-D2 extracellular domain,
    the extracellular domain lacks an ILT2 D3-D4 extracellular domain,
    the chimeric receptor protein comprises a CD8 stalk domain,
    the TM region is a CD TM,
    the signaling region comprises a CD3ζ signaling domain, and
    the chimeric receptor protein comprises a 4-1 BB costimulatory domain.

19. The chimeric receptor protein of 1, wherein:
    the D1-D2 extracellular domain is an ILT4 D1-D2 extracellular domain,
    the extracellular domain lacks an ILT4 D3-D4 extracellular domain,
    the chimeric receptor protein comprises a CD8 stalk domain,
    the TM region is a CD TM,
    the signaling region comprises a CD3ζ signaling domain, and
    the chimeric receptor protein comprises a 4-1 BB costimulatory domain.

20. The chimeric receptor protein of 1, wherein:
    the D1-D2 extracellular domain is an ILT2 D1-D2 extracellular domain,
    the extracellular domain comprises an ILT2 D3-D4 extracellular domain,
    the chimeric receptor protein comprises a CD8 stalk domain,
    the TM region is a CD TM,
    the signaling region comprises a CD3ζ signaling domain, and
    the chimeric receptor protein comprises a 4-1 BB costimulatory domain.

21. The chimeric receptor protein of 1, wherein:
    the D1-D2 extracellular domain is an ILT4 D1-D2 extracellular domain,
    the extracellular domain comprises an ILT4 D3-D4 extracellular domain,
    the chimeric receptor protein comprises a CD8 stalk domain,
    the TM region is a CD TM,
    the signaling region comprises a CD3ζ signaling domain, and
    the chimeric receptor protein comprises a 4-1 BB costimulatory domain.

22. A nucleic acid, comprising a nucleotide sequence encoding the chimeric receptor protein of any one of 1-21.

23. The nucleic acid of 22, wherein said nucleotide sequence is operably linked to a constitutive promoter.

24. The nucleic acid of 22, wherein said nucleotide sequence is operably linked to an inducible promoter.

25. The nucleic acid of any one of 22-24, wherein said nucleic acid is an expression vector.

26. The nucleic acid of 25, wherein the expression vector is a retroviral vector, a lentiviral vector or a plasmid vector.

27. A genetically modified cell, expressing the chimeric receptor protein of any one of 1-22.

28. The genetically modified cell of 27, wherein the genetically modified cell is an immune cell.

29. The genetically modified cell of 28, wherein the immune cell is a natural killer (NK) cell, a T cell, an iNKT cell, or a macrophage.

30. The genetically modified cell of 28, wherein the immune cell is a natural killer (NK) cell.

31. The genetically modified cell of 28, wherein the immune cell is a T cell.

32. The genetically modified cell of any one of 27-31, wherein said genetically modified cell expresses a safety switch.

33. The genetically modified cell of 32, wherein the safety switch is inducible.

34. The genetically modified cell of 33, wherein the safety switch is triggered by rimiducid or by rapamycin or an analog of rapamycin.

35. The genetically modified cell of any one of 27-34, wherein the genetically modified cell further expresses a chimeric antigen receptor.

36. The genetically modified cell of any one of 27-35, wherein the genetically modified cell further expresses a costimulatory polypeptide that is not fused to the chimeric receptor protein.

37. The genetically modified cell of 36, wherein said costimulatory polypeptide that is not fused to the chimeric receptor protein comprises a 4-11BB, OX40, CD28, ICOS, RANK, DAP10, DAP12, CD27, MyD88, IL-1 Rα, HVEM, TRANCE, IL-1Rβ, CD70, IL-18Rα, CD40, IL-18Rβ, IL-33Rα, CD30, or IL-33Rβ costimulatory domain, or any combination thereof.

38. A method of treatment, comprising administering the genetically modified cell of any one of 27-37 to an individual in need.

39. The method of 38, wherein the genetically modified cell is autologous to the individual.

40. The method of 38, wherein the genetically modified cell is allogeneic to the individual.

41. The method of any one of 38-40, wherein the individual has cancer.

42. The method of 41, wherein the individual has a solid tumor.

43. A method of producing a genetically modified cell, the method comprising:
    introducing the nucleic acid of any one of 22-26 into a cell, thus producing a genetically modified cell.

44. The method of 43, wherein the genetically modified cell is an immune cell.

45. The method of 44, wherein the immune cell is a natural killer (NK) cell, a T cell, an iNKT cell, or a macrophage.

46. The method of 44, wherein the immune cell is a natural killer (NK) cell.

47. The method of 44, wherein the immune cell is a T cell.

EXPERIMENTAL EXAMPLES

The following examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1: Expression of Engineered CIR Constructs in Primary Human T Cells

To demonstrate the utility of expression of chimeric receptors that target HLA-G through binding to its natural receptors altered to produce signals that activate immune function versus inhibitory signaling, recombinant DNA constructs were engineered in the SFG γ-retroviral vector (see Schematic diagram on FIG. 6A). In one example the full length gene encoding ILT4 was cloned 5' to a gene encoding the extracellular domain of CD19 (ΔCD19) (see Table 21B). The full length ΔCD19 was useful to mark the expression of transgenes introduced with this vector. The cistrons encoding ILT4 and CD19 were separated by the T2A cotranslational cleavage site derived from *Thosea asigna* virus to permit separate protein expressing from individual mRNA molecules. All other examples were similarly marked ΔCD19 separated by T2A sequences.

Another example of an expression construct encoded a Chimeric ILT Receptor (CIR) encoding the D1 through D4 domains and the transmembrane domains of ILT4 but replacing the native intracellular domains of ILT4 with a costimulatory domain derived from human 4-1 BB and the signaling domain derived from human CD3ζ (BB.ζ). This construct encoded a CIR protein denoted CIR1 in this example (see Table 23B). A further example encoded CIR2 which contained sequences encoding only the D1 and D2 domains that interact with HLA-G directly and not the D3 and D4 domains. These sequences were fused with those encoding the ILT4 transmembrane domain and the costimulatory domain for 4-1 BB and CD3ζ signaling domain (see Table 24B). Further examples replaced the sequences encoding the ILT4 stalk and transmembrane domains with those encoding the stalk and transmembrane domains of CD8α. These constructs encoded ILT4 CIR3 (see Table 37) and CIR4 (see Table 28B).

Figure 6B:
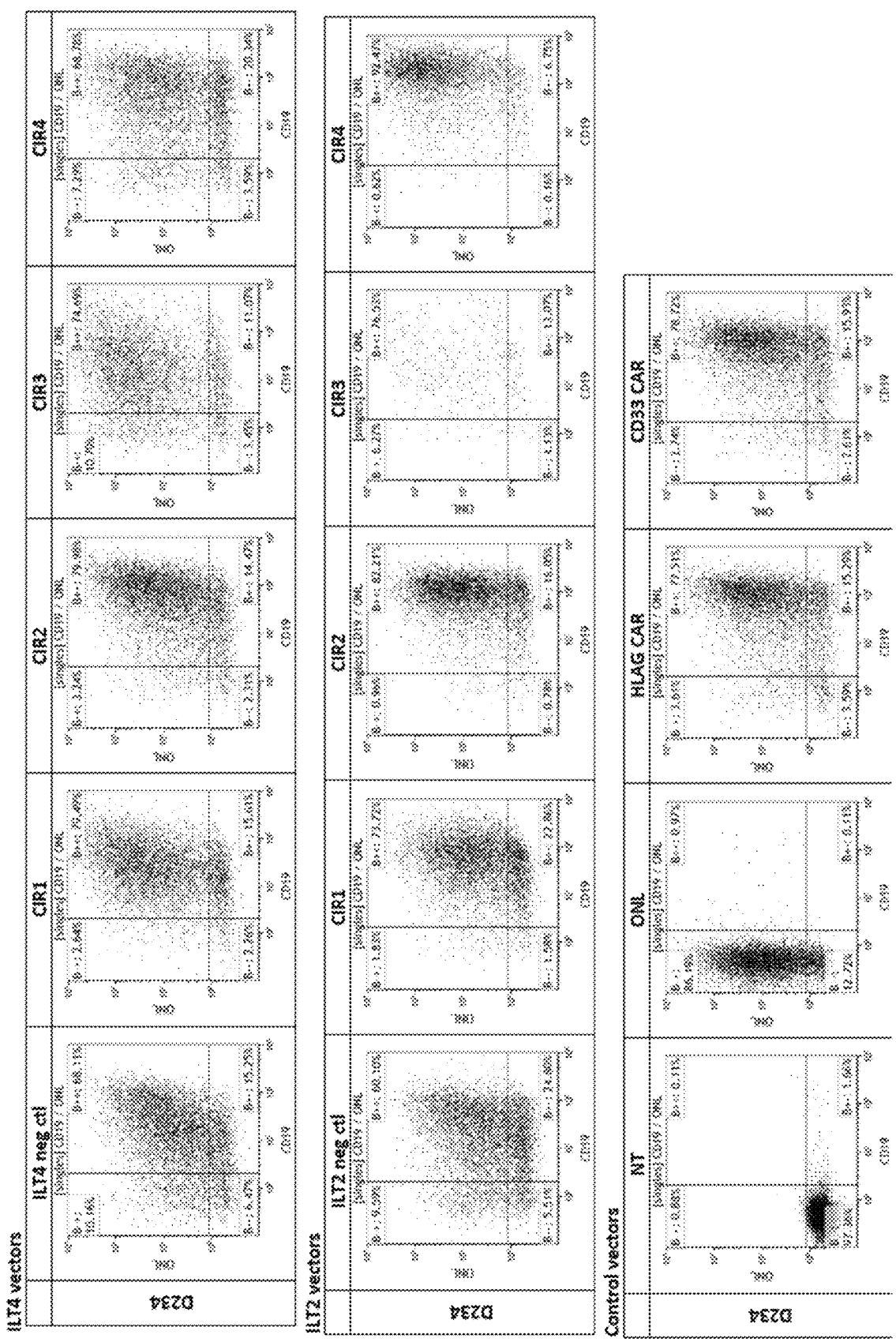
Figure 6C:
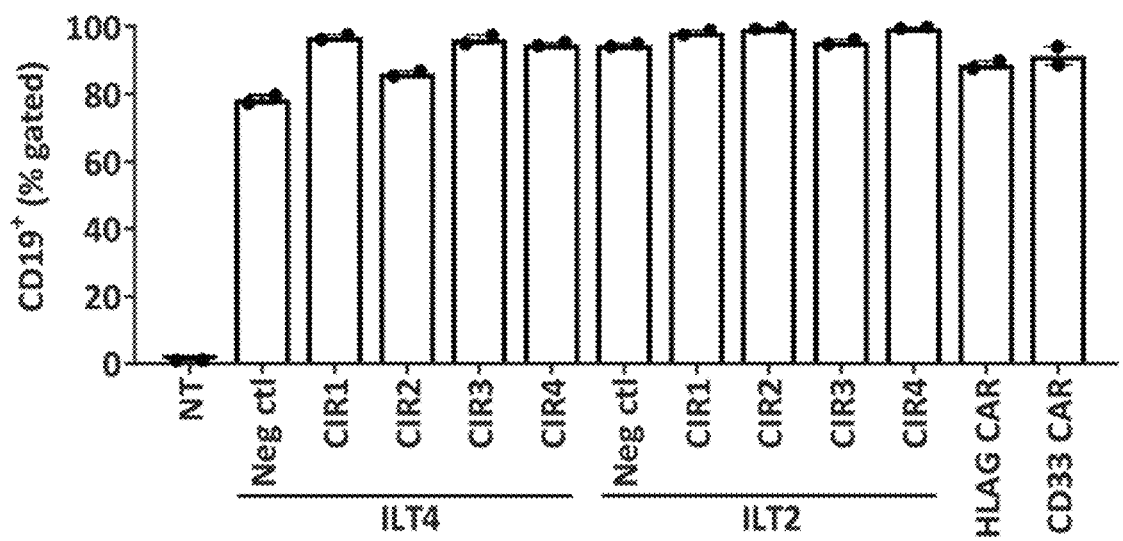
Figure 6D:
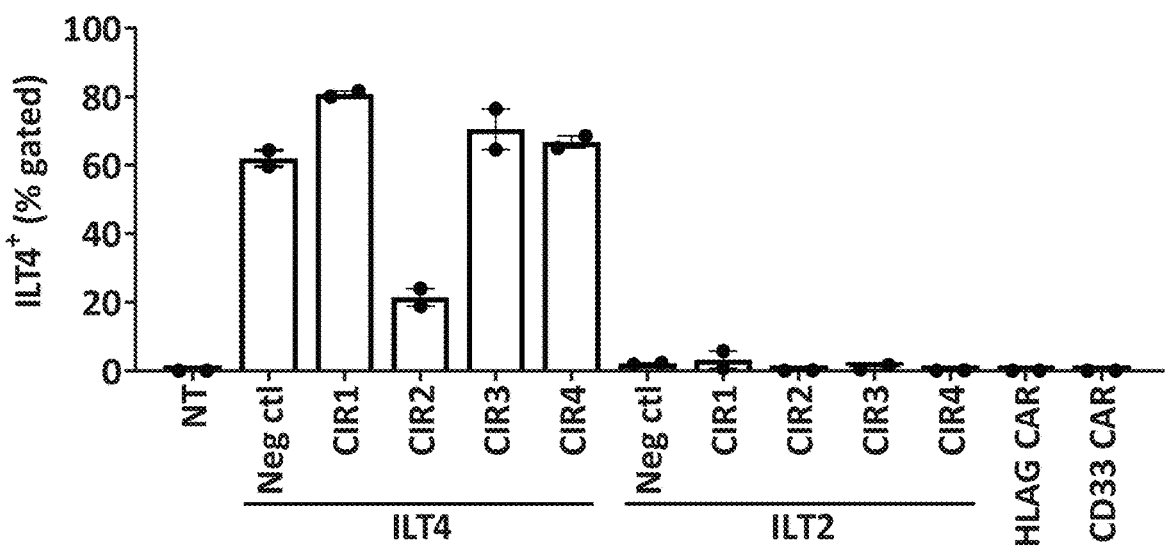

Yet further examples replaced the sequences encoding the D1 through D4 domains of ILT4 with those encoding ILT2 or only the D1 and D2 domains of ILT2. These constructs encoded ILT2 CIR1, CIR2, CIR3 and CIR4 (see Tables 15B, 16B, 36, and 20B, respectively). In ILT2 CIR1 and CIR2 the sequences encoding the stalk and transmembrane domain of ILT2 were utilized and CIR3 and CIR4 replaced these sequences with those encoding CD8α stalk and transmembrane domains. Two further constructs were generated as positive controls for further experimentation. They encoded the binding elements of an HLA-G specific antibody 15E7 (see U.S. patent Ser. No. 11/312,774B2) fused with the CD8α stalk and transmembrane domains of CD8α and BB.ζ intracellular domains. Together this encodes and HLA-G chimeric antigen receptor (HLA-G CAR). A second positive control construct encoded a CAR directed against CD33 (Duong et al, Mol. Ther. Onc. 12: 124), a target protein commonly expressed by acute myeloid leukemia cells (AML).

γ-Retroviruses were produced from these DNA constructs by transfection into HEK293 cells together with helper plasmids encoding reverse transcriptase and viral capsid and envelope proteins. These retroviral vectors were used to transduce primary human T cells derived from 2 healthy donors. The efficiency of transduction was marked by expression of the ΔCD19 marker protein detected by flow cytometry (see FIG. 6B). The efficiency of transduction was greater than 80% for each recombinant retrovirus (FIG. 6C). Expression of CIR constructs containing the extracellular domains of ILT4 and ILT2 was determined by flow cytometry with antibodies specific for ILT4 (FIG. 6D) and ILT2 (FIG. 6E) quantitated by the mean fluorescence intensity of populations of stained transduced cells. Stable expression of CIR proteins was readily detectable although the expression level of ILT2 CIR4 was notably reduced relative to other CIR proteins.

The experiments described in this example demonstrated that recombinant retroviruses encoding CIR proteins derived from ILT2 and ILT4 can be generated and that transduction of primary human immune cells with these retroviruses can be performed to generate immune cells expressing CIR proteins stably.

Methods: DNA constructs were designed with SnapGene software and DNA sequences were synthesized from GBlock fragments by IDT Laboratories. Synthetic DNA fragments were cloned with standard cloning techniques for recombinant DNA assembly into the SFG DNA vector for production of retrovirus based on Moloney Murine Leukemia Virus.

Example 2: Anti-Tumor Efficacy with CIR-T Cells

To generate tumor cell lines stably expressing different isoforms of HLA-G, recombinant retroviruses encoding HLA-G isoforms HLA-G1, HLA-G2 and HLA-G5 were generated. Each of these retroviruses also encoded a marker protein ΔEGFR separated from HLA-G with the T2A cotranslational cleavage element to detect the efficiency of viral transduction. These γ-retroviruses were used to transduce THP1 AML cells for stable, high level expression HLA-G isoforms. Transduction efficiency marked by staining with antibodies to EGFR was detected by flow cytometry and was high for each recombinant retrovirus. Expression of HLA-G in transduced THP1 cells was also determined by flow cytometry with the MEM-G/9 antibody specific for HLA-G1 and not HLA-G2, and expression was at a high level in transduced cells.

Expression of the GFP-ffluc marker protein in THP1-GFP cells also expressing HLA-G1 was at a high level (FIG. 7B). GFPffluciferase expression was useful to indirectly measure the loss of viability of THP1 cells in coculture experiments with CIR-T cells by a reduction in green fluorescence over time or a loss of luciferase enzymatic activity. HLA-G expressing THP1 cells were thereby appropriate target cells for determination of the cytotoxicity of CIR-expressing T cells.

Primary human T cells from two healthy donors were transduced with the same cohort of CIR- and CAR-encoding retroviruses described in example 1. CIR-T, CAR-T or mock transduced (NT) T cells were cocultured with HLA-G1 expressing THP1-GFP cells at an effector to target ratio of 5:1 and were placed in an Incucyte incubator that was equipped with a microscope capable of periodic imaging over 2 days. Green fluorescence from the THP1-HLAG1 GFP cells was quantitated every 12 hours during the coculture period as an indirect measure of tumor outgrowth or tumor cell killing (FIG. 8). Cocultures with mock transduced T cells or with T cells transduced to express full length ILT2 or ILT4 that contain the native inhibitor signaling domains (Neg control, Neg ctl) showed stable expression of GFP in the tumor targets. Coculture with HLA-G CAR-T cells or CD33 CAR-T cells showed a reduction of GFP fluorescence beginning with the first 12 hour timepoint indicating tumor control. These CAR-T cells served as positive controls in this experiment. ILT2 CIR-T cells derived from each donor also demonstrated reduced GFP fluorescence and effective tumor control. It was noted that CIR4 construct was reduced in its anti-tumor efficacy possibly due to the reduced expression level of this construct (see FIG. 6E). ILT4 CIR-T cells also exhibited effective control of THP-1 HLA-G1 expansion.

Anti-tumor efficacy over a short 24 hour time course against the same THP-1 HLA-G1 was determined by measurement of luciferase activity linked to GFP-luciferase expression in the tumor target in cocultures with transduced human T cells (FIG. 9). Cocultures with T cells (E:T—5:1 and 1:1) expressing full length ILT2 (Neg Ctl) had a measurable luciferase activity of over 100,000 light units and served as a reference for other ILT2 CIR constructs ability to kill THP1-HLA-G1-GFPffluc targets. ILT2 CIR-T cell cocultures had markedly reduced luciferase activity demonstrating the killing ability of ILT2 CIR-T cells. Again it was noted that ILT2 CIR4 cells demonstrated reduced anti-tumor cytotoxicity relative to other CIR-T cells and the CAR-T cell positive controls possibly due to reduced CIR expression. Cocultures with ILT4 CIR-T cells also demonstrated enhanced anti-THP1-HLAG1 cytotoxicity relative to the full length ILT4 (Neg Ctl). It was noted that in this case CIR4-T cells had superior anti-tumor cytotoxicity relative to other CIR-T cells and to CD33 CAR-T cells.

The experiments described in this example demonstrate that expression of CIR proteins in human immune cells (T cells in this particular example embodiment) can redirect the specificity of the immune cells (e.g., T cells) to HLA-G expressing tumor targets. Further, these experiments demonstrate that binding interaction between HLA-G and ILT2 or ILT4 sequences are not sufficient for anti-tumor efficacy, but rather that replacement of native ILT2 or ILT4 intracellular signaling domains with domains that activate T cell function are required for enhanced cytotoxicity. Further, it was demonstrated that the D1 and D2 domains of ILT2 or ILT4 are sufficient to target HLA-G in chimeric ILT receptor (CIR) constructs.

Example 3: Alteration of the Stalk and Transmembrane Domains in CIR Constructs In engineered chimeric proteins designed to promote both binding interaction with target cells and intracellular signal transduction upon engagement, selection of optimal linker domains can be important for obtaining increased efficiency. Stalk domains extend target-specific binding elements from the cell membrane and present the binding element in a context that does not inhibit engagement with the target protein. Transmembrane domains facilitate signal transduction to the intracellular domains upon engagement and maintain stable expression in the plasma membrane.

Examples 1 and 2 demonstrated that ILT4 CIR4 exhibited appropriate expression levels upon transduction in human T cells and enhanced antitumor cytotoxicity relative to other CIR constructs. This construct design containing the D1 and D2 domains of ILT4 together the BB.ζ signaling elements was used in 'mix and match' experiments replacing the CD8α stalk and transmembrane domains with stalks and transmembrane domains of other signaling receptors. The constructs that were created are depicted in FIG. 10. As an example CIR6 replaced the CD8α stalk with the CH2 and CH3 domains derived from the human immunoglobulin protein IgG4. A second example reduced the length of the stalk by encoding only the CH3 domain of human IgG4 also fused with the CD8α transmembrane domain. Another example fused the CH3CH2 stalk with the transmembrane domain derived from human CD28 with a fourth example also reducing the length of the stalk to the CH3 domain alone also fused with the CD28 TM. Yet a further example encoded a short CD28-derived stalk fused with the CD28 transmembrane domain. These CIR constructs were denoted CIR6, CIR7, CIR8, CIR9 and CIR10 (see Tables 38-42, respectively). Retroviral constructs encoding these alternative ILT4 CIR derivatives also encoded the ΔCD19 marker protein separated by the T2A cotranslational cleavage site.

γ-Retroviruses encoding the ILT4 CIR constructs were produced and primary human T cells were transduced. Transductions were performed with 2 or 8 millilitres (mL) of retroviral supernatant for a low and a high multiplicity of infection. Overall transduction efficiency was monitored by flow cytometry to detect ΔCD19 marker expression at day 7 and day 14 post transduction (FIG. 11A). Transduction efficiency was greater than 60% for control constructs encoding ILT2 CIR4, ILT4 CIR4 (the parent construct), and HLA-G CAR. Transduction efficiency was comparable for ILT4 CIR derivatives containing the CD28 transmembrane domain. However transduction efficiency was relatively poor for CIR constructs encoding the CD8α transmembrane domain matched with the CH2CH3 or CH3 stalk. Expression levels of ILT4 CIR derivatives were examined by flow cytometry with ILT4 specific antibodies (FIG. 11B, FIG. 11C). Expression of CIR4 containing the CD8α stalk and transmembrane domain was robust when examined as a % of cells gated above background (FIG. 11B) or as the mean fluorescence intensity (MFI) of the signal. Conversely, the MFI of ILT4 CIR derivatives with alternative stalks or transmembrane domains was not elevated above the background signals observed in T cells transduced with control constructs such as the HLA-G CAR or ILT2 CIR4 that do not express ILT4 CIR.

The experiments described in this example indicate that the context of presentation of D1 and D2 domains of ILT4 can be important for the stable expression of a CIR and, by extension, optimal functionality of CIR-T cells.

Example 4: Broad Specificity for CIR-T Cell Targeting of HLA-G Isoforms

Chimeic antigen receptors (CARs) engage their macromolecule target through binding domains typically derived from antibodies, VhH domains that are similar to antibodies or, less commonly, synthetic peptides selected for target affinity and screened for target specificity. In each of these cases the binding domain achieves specificity and affinity randomly and a binder is selected from the broad diversity of the pool of potential binders. Importantly, the epitope on the target engaged by the binder is most frequently a linear group of amino acids that can be removed or restructured by alterations in the sequence identity of different functional isoforms of the target protein produced by alternative mRNA splicing or post-translational modification. In the case of HLA-G, the HLA-G2 isoform removes the entire α2 domain, and any antibody that uses an epitope requiring α2 to be exposed will be masked from interaction with HLA-G2. We realized that conversely, receptor-ligand interactions between proteins tend to have broad regions of binding interaction that would be selected naturally. In the example of HLA-G interaction with ILT2 and ILT4, we realized that performance of the function of HLA-G as an agent of immune evasion by the fetal placenta or by tumor cells would likely require each functional isoform to interact with ILT2 and ILT4. Experiments were therefore designed to test whether this natural selection for broad specificity meant that chimeric ILT receptors (CIRs) would have a more broad specificity for HLA-G isoforms than a typical HLA-G targeted chimeric antigen receptor (CAR).

Molm13-GFPffluc and Molm14-GFPffluc cells are derived from AML tumors and each was stably transduced to express GFP as a fusion with firefly luciferase. Each was assessed for the expression of HLA-G by flow cytometry, and Molm14 cells were found to be HLA-G positive (FIG. 12). Primary human T cells from two donors were transduced with ILT4 CIR4, CIR6 and CIR7 constructs encoding ILT4 D1 and D2 domains as the HLA-G binder with CD8α transmembrane domains and CD8α stalks (CIR4), CH2CH3 stalk (CIR6) or CH3 stalk (CIR7). HLA-G CAR-T cells were also produced in these experiments.

Cocultures of transduced T cells and HLAG-expressing Molm14 targets were performed at an E:T ratio of 5:1. Cocultures were assessed for the ability of CIR-T or CAR-T cells to control tumor expansion by monitoring GFP fluorescence in an Incucyte incubator/microscope (FIG. 13A). Mock transduced T cells not expressing a CIR or CAR did not control Molm14 expansion over 48 hours, but ILT4 CIR4-T cocultures displayed far reduced GFP fluorescence relative to mock transduced cells. CIR 6 and CIR7-T cells displayed poor control of Molm14 cells as expected given the poor expression of these constructs displayed in Example 3. Surprisingly HLA-G CAR-T cells also demonstrated poor ability to control Molm14-GFPffluc cell growth.

Similar cocultures were performed to determine cytotoxicity of CIR-T and HLA-G CAR-T cells against Molm14-GFPffluc cells over 24 hours by reduction of luciferase activity (FIG. 13B). Luciferase activity produced by Molm14-GFPffluc cells cocultured with mock transduced T cells was identical to that of tumor cells cultured alone. Cocultures with HLA-G CAR-T cells produced had closely similar luciferase activity to those with mock transduced T cells indicating that HLA-G CAR-T cells in an independent assay for cytotoxicity failed to target Molm14 AML cells. Conversely, ILT4 CIR4-T cells had substantial cytotoxicity against Molm14-GFPffluc targets. These results led to the hypothesis that the HLA-G CAR-T cells may not recognize an HLA-G isoform present on Molm14 cells that is instead identified and targeted by an ILT4 D1D2 CIR.

To determine if ILT4 CAR-T cells display a broad specificity for targeting HLA-G isoforms, cocultures of ILT4 CIR-T cells expressing an optimal stalk and transmembrane domain (CIR4) or suboptimal domains that reduce expression (CIR6, CIR7) or HLA-G CAR-T cells were cocultured with THP1-GFPluc cells transduced to express HLA-G1 only (FIG. 14A) or HLA-G2 only (FIG. 14B). Upon engagement of a binder with a target protein and activation of signal transduction, proinflammatory cytokine production is induced. Interferon-γ (IFN-γ) secretion into the media was used as a proxy for the activation state of T cells in cocultures. As expected from the results displayed in Example 2, both cocultures of HLA-G1 expressing target cells with ILT4 CIR4-T cells and HLA-G CAR-T cells displayed enhanced IFN-γ production (FIG. 14A). Interestingly, IFN-γ production was only stimulated with ILT4 CIR4-T cells cocultured with THP1-HLA-G2-GFPffluc target cells and IFN-γ secretion was not supported in cocultures of HLA-G CAR-T cells with target cells expressing only HLA-G2 (FIG. 14B).

The results presented in this example indicated that the specificity of targeting of HLA-G isoforms can be enhanced (e.g., the range of isoforms that can be targeted can be broadened) by use of an ILT D1 and D2 containing binding agent (ILT4 D1-D2 was used in this particular example embodiment) compared to that of an antibody-derived binder in a classic chimeric antigen receptor (CAR).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

SEQUENCE LISTING

```
Sequence total quantity: 110
SEQ ID NO: 1            moltype = DNA   length = 250
FEATURE                 Location/Qualifiers
source                  1..250
                        mol_type = other DNA
                        organism = synthetic construct
SEQUENCE: 1
tgccccggct cagggccaag aacagatgga acagctgaat atgggccaaa caggatatct   60
gtggtaagca gttcctgccc cggctcaggg ccaagaacag atggtcccca gatgcggtcc  120
agccctcagc agtttctaga gaaccatcag atgtttccag ggtgccccaa ggacctgaaa  180
tgaccctgtg ccttatttga actaaccaat cagttcgctt ctcgcttctg ttcgcgcgct  240
tatgctcccc                                                         250

SEQ ID NO: 2            moltype = DNA   length = 243
FEATURE                 Location/Qualifiers
source                  1..243
                        mol_type = other DNA
                        organism = synthetic construct
SEQUENCE: 2
gagctcaata aaagagccca caaccccctca ctcggggcgc cagtcctccg attgactgag   60
tcgcccgggt acccgtgtat ccaataaacc ctcttgcagt tgcatccgac ttgtggtctc  120
gctgttcctt gggagggtct cctctgagtg attgactacc cgtcagcggg ggtctttcat  180
ttgggggctc gtccgggatc gggagacccc tgcccaggga ccaccgaccc accaccggga  240
ggt                                                                243

SEQ ID NO: 3            moltype = DNA   length = 358
FEATURE                 Location/Qualifiers
source                  1..358
                        mol_type = other DNA
                        organism = synthetic construct
SEQUENCE: 3
aagctggcca gcaacttatc tgtgtctgtc cgattgtcta gtgtctatga ctgattttat   60
gcgcctgcgt cggtactagt tagctaacta gctctgtatc tggcggaccc gtggtggaac  120
tgacgagttc ggaacacccg gccgcaaccc tgggagacgt cccagggact tcgggggccg  180
tttttgtggc ccgacctgag tcctaaaatc ccgatcgttt aggactcttt ggtgcacccc  240
ccttagagga gggatatgtg gttctggtag gagacgagaa cctaaaacag ttcccgcctc  300
cgtctgaatt tttgcttttcg gtttgggacc gaagccgcgc cgcgcgtctt gtctgctg    358

SEQ ID NO: 4            moltype = DNA   length = 62
FEATURE                 Location/Qualifiers
source                  1..62
                        mol_type = other DNA
                        organism = synthetic construct
SEQUENCE: 4
cagcatcgtt ctgtgttgtc tctgtctgac tgtgtttctg tatttgtctg aaaatatggg   60
cc                                                                  62

SEQ ID NO: 5            moltype = DNA   length = 420
FEATURE                 Location/Qualifiers
source                  1..420
                        mol_type = other DNA
                        organism = synthetic construct
SEQUENCE: 5
cgggctagcc tgttaccact cccttaagtt tgaccttagg tcactggaaa gatgtcgagc   60
ggatcgctca caaccagtcg gtagatgtca agaagagacg ttgggttacc ttctgctctg  120
cagaatggcc aacctttaac gtcggatggc cgcgagacgg cacctttaac cgagacctca  180
tcacccaggt taagatcaag gtcttttcac ctggccccgca tggacaccca gaccaggtgg  240
ggtacatcgt gacctgggaa gccttggctt ttgacccccc tccctgggtc aagccctttg  300
tacaccctaa gcctccgcct cctcttcctc catccgcccc gtctctcccc cttgaacctc  360
ctcgttcgac cccgcctcga tcctcccttt atccagccct cactccttct ctaggcgccc  420

SEQ ID NO: 6            moltype = DNA   length = 305
FEATURE                 Location/Qualifiers
source                  1..305
                        mol_type = other DNA
                        organism = synthetic construct
SEQUENCE: 6
ccatatgaga tcttatatgg ggcaccccccg ccccttgtaa acttccctga ccctgacatg   60
acaagagtta ctaacagccc ctctctccaa gctcacttac aggctctcta cttagtccag  120
cacgaagtct ggagacctct ggcggcagcca taccaagaac aactggaccg accggtggta  180
cctcacccctt accgagtcgg cgacacagtg tgggtccgcc gacaccagac taagaaccta  240
gaacctcgct ggaaaggacc ttacacagtc ctgctgacca cccccaccgc cctcaaagta  300
gacgg                                                              305

SEQ ID NO: 7            moltype = DNA   length = 72
FEATURE                 Location/Qualifiers
source                  1..72
                        mol_type = other DNA
```

```
                        organism = synthetic construct
SEQUENCE: 7
catcgcagct tggatacacg ccgcccacgt gaaggctgcc gaccccgggg gtggaccatc    60
ctctagactg cc                                                        72

SEQ ID NO: 8            moltype = DNA   length = 1014
FEATURE                 Location/Qualifiers
source                  1..1014
                        mol_type = unassigned DNA
                        organism = Homo sapiens
SEQUENCE: 8
atggtggtca tggcaccccg aaccctcttc ctgctactct cggggggccct gaccctgacc   60
gagacctggg cgggctccca ctccatgagg tatttcagcg ccgccgtgtc ccggcccggc   120
cgcggggagc cccgcttcat cgccatgggc tacgtggacg acacgcagtt ccgcggcgtt   180
gacagcgact cggcgtgtcc gaggatggag ccgcgggcgc cgtgggtgga gcaggagggg   240
ccagagtatt gggaagagga gacacggaac accaaggccc acgcacagac tgacagaatg   300
aacctgcaga cccctgcgcg gctactacaac agagcgaggc cagttctca caccctccag   360
tggatgattg gctgcgacct ggggtccgac ggacgcctca tccgcgggta tgaacgctat   420
gcctacgatg gcaaggatta cctcgccctg aacgaggacc tgcgctcctg gaccgcagcg   480
gacactgcgg ctcagatctc caagcgcaag tgtgaggcgg ccaatgtggc tgaacaaagg   540
agagcctacc tggagggcac gtgcgtggag tggctccaca gatacctgga gaacgggaag   600
gagatgctgc agcgcgcgga cccccccaag acacacgtga cccaccaccc tgtctttgac   660
tatgaggcca ccctgaggtg ctgggccctg gcttctacc ctgcggagat catactgacc    720
tggcagcggg atggggagga ccagacccag gacgtggagc tcgtggagac caggcctgca   780
ggggatggaa ccttccagaa gtgggcagct gtggtggtgc cttctggaga ggagcagaga   840
tacacgtgcc atgtgcagca tgagggctgc cggagcccca tcatgctgag atggaagcag   900
tcttccctgc ccaccatccc catcatgggt atcgttgctg gcctggttgt ccttgcagct   960
gtagtcactg gagctgcggt cgctgctgtg ctgtggagga agaagagctc agat         1014

SEQ ID NO: 9            moltype = AA   length = 338
FEATURE                 Location/Qualifiers
source                  1..338
                        mol_type = protein
                        organism = Homo sapiens
SEQUENCE: 9
MVVMAPRTLF LLLSGALTLT ETWAGSHSMR YFSAAVSRPG RGEPRFIAMG YVDDTQFVRF    60
DSDSACPRME PRAPWVEQEG PEYWEEETRN TKAHAQTDRM NLQTLRGYYN QSEASSHTLQ   120
WMIGCDLGSD GRLIRGYERY AYDGKDYLAL NEDLRSWTAA DTAAQISKRK CEAANVAEQR   180
RAYLEGTCVE WLHRYLENGK EMLQRADPPK THVTHHPVFD YEATLRCWAL GFYPAEIILT   240
WQRDGEDQTQ DVELVETRPA GDGTFQKWAA VVVPSGEEQR YTCHVQHEGL PEPLMLRWKQ   300
SSLPTIPIMG IVAGLVVLAA VVTGAAVAAV LWRKKSSD                           338

SEQ ID NO: 10           moltype = DNA   length = 54
FEATURE                 Location/Qualifiers
source                  1..54
                        mol_type = other DNA
                        organism = synthetic construct
SEQUENCE: 10
gagggcagag gcagcctcct gacatgtggg gacgtcgagg agaaccctgg ccca           54

SEQ ID NO: 11           moltype = AA   length = 18
FEATURE                 Location/Qualifiers
source                  1..18
                        mol_type = protein
                        organism = synthetic construct
SEQUENCE: 11
EGRGSLLTCG DVEENPGP                                                   18

SEQ ID NO: 12           moltype = DNA   length = 999
FEATURE                 Location/Qualifiers
source                  1..999
                        mol_type = other DNA
                        organism = synthetic construct
SEQUENCE: 12
atgccacctc ctcgcctcct cttcttcctc ctcttcctca cccccatgga agtcaggccc    60
gaggaacctc tagtggtgaa ggtggaagag ggagataacg ctgtgctgca gtgcctcaag   120
gggacctcag atgcccccac tcagcagctg acctggtctc gggagtcccc gcttaaaccc   180
ttcttaaaac tcagcctggg gctgccaggc ctgggaatcc acatgaggcc cctggccatc   240
tggcttttca tcttcaacgt ctctcaacag atgggggagc tctacctgcc ccagccgagg   300
cccccctctg agaaggcctg gcagcctggc tggacagtca atgtggaggg cagcggggag   360
ctgttccggt ggaatgtttc ggacctaggt ggcctgggct gtggcctgaa gaacaggtcc   420
tcagagggcc ccagctcccc ttccgggaag ctcatgagcc caagctgta tgtgtgggc    480
aaagaccgcc tgagatctg ggaggagag cctccgtgtc tcccaccgag ggacagcctg   540
aaccagacag tcagcagga cctcaccatg gccccatgg ccacactctg gctgtcctgt    600
gggtacccct gactctgt gtccagggc cccctctcct ggaccatgt gcaccccag    660
gggcctaagt cattgctgag cctagagctg aaggacgatc gccgggcag agatatgtgg   720
gtaatggaga cgggtctgtt gttgcccgg gccacagctc aagacgctgg aaagtattat   780
tgtcaccgtg gcaacctgac catgtcatte cacctgagaa tcactgctcg gccagtacta   840
tggcactggc tgctgaggac tggtggctgg aaggtctcag ctgtgacttt ggcttatctg   900
```

```
atcttctgcc tgtgttccct tgtgggcatt cttcatcttc aaagagccct ggtcctgagg    960
aggaaaagaa agcgaatgac tgaccccacc aggagattc                           999
```

SEQ ID NO: 13          moltype = AA   length = 333
FEATURE                Location/Qualifiers
source                 1..333
                       mol_type = protein
                       organism = synthetic construct
SEQUENCE: 13
```
MPPPRLLFFL LFLTPMEVRP EEPLVVKVEE GDNAVLQCLK GTSDGPTQQL TWSRESPLKP     60
FLKLSLGLPG LGIHMRPLAI WLFIFNVSQQ MGGFYLCQPG PPSEKAWQPG WTVNVEGSGE    120
LFRWNVSDLG GLGCGLKNRS SEGPSSPSGK LMSPKLYVWA KDRPEIWEGE PPCLPPRDSL    180
NQSLSQDLTM APGSTLWLSC GVPPDSVSRG PLSWTHVHPK GPKSLLSLEL KDDRPARDMW    240
VMETGLLLPR ATAQDAGKYY CHRGNLTMSF HLEITARPVL WHWLLRTGGW KVSAVTLAYL    300
IFCLCSLVGI LHLQRALVLR RKRKRMTDPT RRF                                 333
```

SEQ ID NO: 14          moltype = DNA   length = 738
FEATURE                Location/Qualifiers
source                 1..738
                       mol_type = unassigned DNA
                       organism = Homo sapiens
SEQUENCE: 14
```
atggtggtca tggcgccccg aaccctcttc ctgctgctct cgggggccct gaccctgacc     60
gagacctggg cgggctccca ctccatgagg tatttcagcg ccgccgtgtc ccggcccggc    120
cgcggggagc cccgcttcat cgccatgggc tacgtggacg acacgcagtt cgtgcggttc    180
gacagcgact cggcgtgtcc gaggatggag ccgcggggcgc cgtgggtgga gcaggagggg    240
ccggagtatt gggaagagga gacacgaaac accaaggccc acgcacagac tgacagaatg    300
aacctgcaga ccctgcgcgg ctactacaac cagagcgagg ccaaccccc caagacacac    360
gtgacccacc accctgtctt tgactatgag gccaccctga ggtgctgggc cctgggcttc    420
taccctgcgg agatcatact gacctggcag cgggatggag aggacgacag cagacgacgtg    480
gagctcgtgg agaccaggcc tgcagggat ggaaccttcc agaagtgggc agctgtggtg    540
gtgccttctg gagaggagca gagatacacg tgccatgtgc agcatgaggg gctgccggag    600
cccctcatgc tgagatggaa gcagtcttcc ctgcccacca tccccatcat gggtatcgtt    660
gctggcctgg ttgtccttgc agctgtagtc actgagctg cggtcgctgc tgtgctgtgg    720
agaaagaaga gctcagat                                                  738
```

SEQ ID NO: 15          moltype = AA   length = 246
FEATURE                Location/Qualifiers
source                 1..246
                       mol_type = protein
                       organism = Homo sapiens
SEQUENCE: 15
```
MVVMAPRTLF LLLSGALTLT ETWAGSHSMR YFSAAVSRPG RGEPRFIAMG YVDDTQFVRF     60
DSDSACPRME PRAPWVEQEG PEYWEEETRN TKAHAQTDRM NLQTLRGYYN QSEANPPKTH    120
VTHHPVFDYE ATLRCWALGF YPAEIILTWQ RDGEDQTQDV ELVETRPAGD GTFQKWAAVV    180
VPSGEEQRYT CHVQHEGLPE PLMLRWKQSS LPTIPIMGIV AGLVVLAAVV TGAAVAAVLW    240
RKKSSD                                                               246
```

SEQ ID NO: 16          moltype = DNA   length = 462
FEATURE                Location/Qualifiers
source                 1..462
                       mol_type = unassigned DNA
                       organism = Homo sapiens
SEQUENCE: 16
```
atggtggtca tggcgccccg aaccctcttc ctgctgctct cgggggccct gaccctgacc     60
gagacctggg cgggctccca ctccatgagg tatttcagcg ccgccgtgtc ccggcccggc    120
cgcggggagc cccgcttcat cgccatgggc tacgtggacg acacgcagtt cgtgcggttc    180
gacagcgact cggcgtgtcc gaggatgag ccgcggggcgc cgtgggtgga gcaggagggg    240
ccggagtatt gggaagagga gacacgaaac accaaggccc acgcacagac tgacagaatg    300
aacctgcaga ccctgcgcgg ctactacaac cagagcgagg ccaagcagtc ttccctgccc    360
accatcccca tcatgggtat cgttgctggc ctggttgtcc ttgcagctgt agtcactgga    420
gctgcggtcg ctgctgtgct gtggagaaag aagagctcag at                       462
```

SEQ ID NO: 17          moltype = AA   length = 154
FEATURE                Location/Qualifiers
source                 1..154
                       mol_type = protein
                       organism = Homo sapiens
SEQUENCE: 17
```
MVVMAPRTLF LLLSGALTLT ETWAGSHSMR YFSAAVSRPG RGEPRFIAMG YVDDTQFVRF     60
DSDSACPRME PRAPWVEQEG PEYWEEETRN TKAHAQTDRM NLQTLRGYYN QSEAKQSSLP    120
TIPIMGIVAG LVVLAAVVTG AAVAAVLWRK KSSD                                154
```

SEQ ID NO: 18          moltype = DNA   length = 738
FEATURE                Location/Qualifiers
source                 1..738
                       mol_type = unassigned DNA
                       organism = Homo sapiens
SEQUENCE: 18

```
atggtggtca tggcgccccg aaccctcttc ctgctgctct cggggggccct gaccctgacc    60
gagacctggg cgggctccca ctccatgagg tatttcagcg ccgccgtgtc ccggcccggc   120
cgcggggagc cccgcttcat cgccatgggc tacgtggacg acacgcagtt cgtgcggttc   180
gacagcgact cggcgtgtcc gaggatggag ccgcggggcgc cgtgggtgga gcaggagggg   240
ccggagtatt gggaagagga gacacggaac accaaggccc acgcacagac tgacagaatg   300
aacctgcaga ccctgcgcgg ctactacaac cagagcgagg ccagttctca caccctccag   360
tggatgattg gctgcgacct ggggtccgac ggacgcctcc tccgcgggta tgaacagtat   420
gcctacgatg gcaaggatta cctcgccctg aacgaggacc tgcgctcctg gaccgcagcg   480
gacactgcgg ctcagatctc caagcgcaag tgtgaggcgg ccaatgtggc tgaacaaagg   540
agagcctacc tggagggcac gtgcgtggag tggctccaca gatacctgga acgggaag    600
gagatgctgc agcgcgcgga gcagtcttcc ctgcccacca tccccatcat gggtatcgtt   660
gctggcctgg ttgtccttgc agctgtagtc actggagctg cggtcgctgc tgtgctgtgg   720
agaaagaaga gctcagat                                                 738

SEQ ID NO: 19              moltype = AA   length = 246
FEATURE                    Location/Qualifiers
source                     1..246
                           mol_type = protein
                           organism = Homo sapiens
SEQUENCE: 19
MVVMAPRTLF LLLSGALTLT ETWAGSHSMR YFSAAVSRPG RGEPRFIAMG YVDDTQFVRF    60
DSDSACPRME PRAPWVEQEG PEYWEEETRN TKAHAQTDRM NLQTLRGYYN QSEASSHTLQ   120
WMIGCDLGSD GRLLRGYEQY AYDGKDYLAL NEDLRSWTAA DTAAQISKRK CEAANVAEQR   180
RAYLEGTCVE WLHRYLENGK EMLQRAEQSS LPTIPIMGIV AGLVVLAAVV TGAAVAAVLW   240
RKKSSD                                                             246

SEQ ID NO: 20              moltype = DNA   length = 957
FEATURE                    Location/Qualifiers
source                     1..957
                           mol_type = unassigned DNA
                           organism = Homo sapiens
SEQUENCE: 20
atggtggtca tggcgccccg aaccctcttc ctgctgctct cggggggccct gaccctgacc    60
gagacctggg cgggctccca ctccatgagg tatttcagcg ccgccgtgtc ccggcccggc   120
cgcggggagc cccgcttcat cgccatgggc tacgtggacg acacgcagtt cgtgcggttc   180
gacagcgact cggcgtgtcc gaggatggag ccgcggggcgc cgtgggtgga gcaggagggg   240
ccggagtatt gggaagagga gacacggaac accaaggccc acgcacagac tgacagaatg   300
aacctgcaga ccctgcgcgg ctactacaac cagagcgagg ccagttctca caccctccag   360
tggatgattg gctgcgacct ggggtccgac ggacgcctcc tccgcgggta tgaacagtat   420
gcctacgatg gcaaggatta cctcgccctg aacgaggacc tgcgctcctg gaccgcagcg   480
gacactgcgg ctcagatctc caagcgcaag tgtgaggcgg ccaatgtggc tgaacaaagg   540
agagcctacc tggagggcac gtgcgtggag tggctccaca gatacctgga acgggaag    600
gagatgctgc agcgcgcgga cccccccaag acacacgtga cccaccaccc tgtctttgac   660
tatgaggcca ccctgaggtg ctgggccctg gcttctacc ctgcggagat catactgacc   720
tggcagcggg atggggagga ccagacccag gacgtggagc tcgtggagac caggcctgca   780
ggggatggaa ccttccagaa gtgggcagct gtggtggtgc cttctggaga ggagcagaga   840
tacacgtgcc atgtgcagca tgagggggctg ccggagcccc tcatgctgag atggagtaag   900
gagggagatg gaggcatcat gtctgttagg gaaagcagga gcctctctga agaccctt    957

SEQ ID NO: 21              moltype = AA   length = 319
FEATURE                    Location/Qualifiers
source                     1..319
                           mol_type = protein
                           organism = Homo sapiens
SEQUENCE: 21
MVVMAPRTLF LLLSGALTLT ETWAGSHSMR YFSAAVSRPG RGEPRFIAMG YVDDTQFVRF    60
DSDSACPRME PRAPWVEQEG PEYWEEETRN TKAHAQTDRM NLQTLRGYYN QSEASSHTLQ   120
WMIGCDLGSD GRLLRGYEQY AYDGKDYLAL NEDLRSWTAA DTAAQISKRK CEAANVAEQR   180
RAYLEGTCVE WLHRYLENGK EMLQRADPPK THVTHHPVFD YEATLRCWAL GFYPAEIILT   240
WQRDGEDQTQ DVELVETRPA GDGTFQKWAA VVVPSGEEQR YTCHVQHEGL PEPLMLRWSK   300
EGDGGIMSVR ESRSLSEDL                                               319

SEQ ID NO: 22              moltype = DNA   length = 957
FEATURE                    Location/Qualifiers
source                     1..957
                           mol_type = other DNA
                           organism = synthetic construct
SEQUENCE: 22
atggtggtca tggcgccccg aaccctcttc ctgctgctct cggggggccct gaccctgacc    60
gagacctggg cgggctccca ctccatgagg tatttcagcg ccgccgtgtc ccggcccggc   120
cgcggggagc cccgcttcat cgccatgggc tacgtggacg acacgcagtt cgtgcggttc   180
gacagcgact cggcgagtcc gaggatggag ccgcggggcgc cgtgggtgga gcaggagggg   240
ccggagtatt gggaagagga gacacggaac accaaggccc acgcacagac tgacagaatg   300
aacctgcaga ccctgcgcgg ctactacaac cagagcgagg ccagttctca caccctccag   360
tggatgattg gctgcgacct ggggtccgac ggacgcctcc tccgcgggta tgaacagtat   420
gcctacgatg gcaaggatta cctcgccctg aacgaggacc tgcgctcctg gaccgcagcg   480
gacactgcgg ctcagatctc caagcgcaag tgtgaggcgg ccaatgtggc tgaacaaagg   540
agagcctacc tggagggcac gtgcgtggag tggctccaca gatacctgga acgggaag    600
gagatgctgc agcgcgcgga cccccccaag acacacgtga cccaccaccc tgtctttgac   660
```

```
tatgaggcca ccctgaggtg ctgggccctg gcttctacc ctgcggagat catactgacc    720
tggcagcggg atggggagga ccagacccag gacgtggagc tcgtggagac caggcctgca    780
ggggatggaa ccttccagaa gtgggcagct gtggtggtgc cttctggaga ggagcagaga    840
tacacgtgcc atgtgcagca tgaggggctg ccggagcccc tcatgctgag atggagtaag    900
gagggagatg gaggcatcat gtctgttagg gaaagcagga gcctctctga agacctt       957

SEQ ID NO: 23         moltype = AA  length = 319
FEATURE               Location/Qualifiers
source                1..319
                      mol_type = protein
                      organism = synthetic construct
SEQUENCE: 23
MVVMAPRTLF LLLSGALTLT ETWAGSHSMR YFSAAVSRPG RGEPRFIAMG YVDDTQFVRF     60
DSDSASPRME PRAPWVEQEG PEYWEEETRN TKAHAQTDRM NLQTLRGYYN QSEASSHTLQ    120
WMIGCDLGSD GRLLRGYEQY AYDGKDYLAL NEDLRSWTAA DTAAQISKRK CEAANVAEQR    180
RAYLEGTCVE WLHRYLENGK EMLQRADPPK THVTHHPVFD YEATLRCWAL GFYPAEIILT    240
WQRDGEDQTQ DVELVETRPA GDGTFQKWAA VVVPSGEEQR YTCHVQHEGL PEPLMLRWSK    300
EGDGGIMSVR ESRSLSEDL                                                 319

SEQ ID NO: 24         moltype = DNA  length = 1014
FEATURE               Location/Qualifiers
source                1..1014
                      mol_type = other DNA
                      organism = synthetic construct
SEQUENCE: 24
atggtggtca tgcacccccg aaccctcttc ctgctactct cgggggccct gaccctgacc     60
gagacctggg cgggctccca ctccatgagg tatttcagcg ccgccgtgtc ccggcccggc    120
cgcggggagc ccgcttcat cgccatgggc tacgtggacg acacgcagtt cgtgcggttc    180
gacagcgact cggcgagtcc gaggatggag ccgcggcgc cgtgggtgga gcaggagggg    240
ccagagtatt gggaagagga gacacggaac accaaggccc acgcacagac tgacagaatg    300
aacctgcaga ccctgcgcgg ctactacaac cagagcgagg ccagttctca caccctccag    360
tggatgattg gctgcgacct ggggtccgac ggacgcctca tccgcgggta tgaacggtat    420
gcctacgatg gcaaggatta cctcgccctg aacgaggacc tgcgctcctg gaccgcagcg    480
gacactgcgg ctcagatctc caagcgcaag tgtgaggcgg ccaatgtggc tgaacaaagg    540
agagcctacc tggagggcac gtgcgtggag tggctccaca gatacctgga gaacgggaag    600
gagatgctgc agcgcgcgga ccccccaag acacacgtga cccaccaccc tgtctttgac    660
tatgaggcca ccctgaggtg ctgggccctg gcttctacc ctgcggagat catactgacc    720
tggcagcggg atggggagga ccagacccag gacgtggagc tcgtggagac caggcctgca    780
ggggatggaa ccttccagaa gtgggcagct gtggtggtgc cttctggaga ggagcagaga    840
tacacgtgcc atgtgcagca tgaggggctg ccggagcccc tcatgctgag atggaagcag    900
tcttccctgc ccaccatccc catcatgggt atcgttgctg gctggttgt ccttgcagct    960
gtagtcactg gagctgcggt cgctgctgtg ctgtggagga agaagagctc agat         1014

SEQ ID NO: 25         moltype = AA  length = 338
FEATURE               Location/Qualifiers
source                1..338
                      mol_type = protein
                      organism = synthetic construct
SEQUENCE: 25
MVVMAPRTLF LLLSGALTLT ETWAGSHSMR YFSAAVSRPG RGEPRFIAMG YVDDTQFVRF     60
DSDSASPRME PRAPWVEQEG PEYWEEETRN TKAHAQTDRM NLQTLRGYYN QSEASSHTLQ    120
WMIGCDLGSD GRLIRGYERY AYDGKDYLAL NEDLRSWTAA DTAAQISKRK CEAANVAEQR    180
RAYLEGTCVE WLHRYLENGK EMLQRADPPK THVTHHPVFD YEATLRCWAL GFYPAEIILT    240
WQRDGEDQTQ DVELVETRPA GDGTFQKWAA VVVPSGEEQR YTCHVQHEGL PEPLMLRWKQ    300
SSLPTIPIMG IVAGLVVLAA VVTGAAVAAV LWRKKSSD                            338

SEQ ID NO: 26         moltype = DNA  length = 1014
FEATURE               Location/Qualifiers
source                1..1014
                      mol_type = other DNA
                      organism = synthetic construct
SEQUENCE: 26
atggtggtca tgcacccccg aaccctcttc ctgctactct cgggggccct gaccctgacc     60
gagacctggg cgggctccca ctccatgagg tatttcagcg ccgccgtgtc ccggcccggc    120
cgcggggagc ccgcttcat cgccatgggc tacgtggacg acacgcagtt cgtgcggttc    180
gacagcgact cggcgtgtcc gaggatggag ccgcggcgc cgtgggtgga gcaggagggg    240
ccagagtatt gggaagagga gacacggaac accaaggccc acgcacagac tgacagaatg    300
aacctgcaga ccctgcgcgg ctactacaac cagagcgagg ccagttctca caccctccag    360
tggatgattg gctgcgacct ggggtccgac ggacgcctca tccgcgggta tgaacggtat    420
gcctacgatg gcaaggatta cctcgccctg aacgaggacc tgcgctcctg gaccgcagcg    480
gacactgcgg ctcagatctc caagcgcaag agtgaggcgg ccaatgtggc tgaacaaagg    540
agagcctacc tggagggcac gtgcgtggag tggctccaca gatacctgga gaacgggaag    600
gagatgctgc agcgcgcgga ccccccaag acacacgtga cccaccaccc tgtctttgac    660
tatgaggcca ccctgaggtg ctgggccctg gcttctacc ctgcggagat catactgacc    720
tggcagcggg atggggagga ccagacccag gacgtggagc tcgtggagac caggcctgca    780
ggggatggaa ccttccagaa gtgggcagct gtggtggtgc cttctggaga ggagcagaga    840
tacacgtgcc atgtgcagca tgaggggctg ccggagcccc tcatgctgag atggaagcag    900
tcttccctgc ccaccatccc catcatgggt atcgttgctg gctggttgt ccttgcagct    960
gtagtcactg gagctgcggt cgctgctgtg ctgtggagga agaagagctc agat         1014
```

```
SEQ ID NO: 27            moltype = AA  length = 338
FEATURE                  Location/Qualifiers
source                   1..338
                         mol_type = protein
                         organism = synthetic construct
SEQUENCE: 27
MVVMAPRTLF LLLSGALTLT ETWAGSHSMR YFSAAVSRPG RGEPRFIAMG YVDDTQFVRF   60
DSDSACPRME PRAPWVEQEG PEYWEEETRN TKAHAQTDRM NLQTLRGYYN QSEASSHTLQ  120
WMIGCDLGSD GRLIRGYERY AYDGKDYLAL NEDLRSWTAA DTAAQISKRK SEAANVAEQR  180
RAYLEGTCVE WLHRYLENGK EMLQRADPPK THVTHHPVFD YEATLRCWAL GFYPAEIILT  240
WQRDGEDQTQ DVELVETRPA GDGTFQKWAA VVVPSGEEQR YTCHVQHEGL PEPLMLRWKQ  300
SSLPTIPIMG IVAGLVVLAA VVTGAAVAAV LWRKKSSD                          338

SEQ ID NO: 28            moltype = DNA  length = 1950
FEATURE                  Location/Qualifiers
source                   1..1950
                         mol_type = unassigned DNA
                         organism = Homo sapiens
SEQUENCE: 28
atgacccca tcctcacggt cctgatctgt ctcgggctga gtctgggccc ccggacccac    60
gtgcaggcag ggcaccctcc caagcccacc tctgggtca aaccaggctc tgtgatcacc   120
caggggagtc ctgtgaccct caggtgtcag gggggccagg agacccagga gtaccgtcta  180
tatagagaaa agaaaacagc accctggatt acacggatcc cacaggagct tgtgaagaag  240
ggccagttcc ccatcccatc catcacctgg gaacacacag gcggtatcg ctgttactat   300
ggtagcgaca ctgcaggccg ctcagagagc agtgaccccc tggagctggt ggtgacagga  360
gcctacatca aacccaccct tcagcccag cccagcccg tggtgaactc aggagggaat    420
gtaaccctcc agtgtgactc acaggtggca tttgatggct tcattctgtg taaggaagga  480
gaagatgaac ccacaatg cctgaactcc agcccatg cccgtgggtc gtcccgcgcc      540
atcttctccg tgggccccgt gagcccgagt cgcaggtggt ggtacaggtg ctatgcttat  600
gactcgaact ctcccctatga gtggtctcta cccagtgatc tcctgagct cctggtccta  660
ggtgtttcta agaagccatc actctcagtg cagccaggtc ctatcgtggc ccctgaggag  720
accctgactc tgcagtgtgg ctctgatgct ggctacaaca gattgttct gtataaggac  780
ggggaacgtg acttccttca gctcgctggc gcacagcccc aggctgggct ctcccaggcc  840
aactttcaccc tgggcccctgt gagccgctcc tacgggggcc agtacagatg ctacggtcga  900
cacaacctct cctccgagtg gtcggccccc agcgacccc tggacatcct gatcgcagga  960
cagttctatg acagagtctc cctctcggtg cagccgggcc ccacggtggc ctcaggagag 1020
aacgtgaccc tgctgtgtca gtcacaggga tggatgcaaa ctttccttct gaccaaggag 1080
gggcagctg atgaccatg cgtctaaga tcaacgtacc aatctcaaaa ataccaggct   1140
gaattcccca tgggtcctgt gacctcagcc catgcgggga cctacaggtg ctacggctca  1200
cagagctcca aaccctacct gctgactcac cccagtgacc cctggagct cgtggtctca  1260
ggaccgtctg ggggccccag ctccccgaca acaggcccca cctccacatc tggccctgag 1320
gaccagcccc tcacccccac cggtgtcggat cccagagtg gtccgggaag gcacctggga 1380
gttgtgatcg gcatcttggt ggccgtcatc ctactgctcc tcctcctcct cctcctcttc 1440
ctcatcctcc gacatcgacg tcagggcaaa cactggacat cgacccagag aaaggctgat 1500
ttccaacatc ctgcagggc tgtggggcca gagcccacag acagaggcct gcagtggagg 1560
tccagcccag ctgccgatgc ccaggaagaa aacctctatg ctgccgtgaa gcacacacag 1620
cctgaggatg gggtggagat ggacactcgg agcccacacg atgaagaccc ccaggcagtg 1680
acgtatgccg aggtgaaaca ctccagacct aggagagaaa tggcctctcc tccttcccca 1740
ctgtctgggg aattcctgga cacaaaggac agacaggcgg aagaggacag gcagatggac 1800
actgaggctg ctgcatctga agccccccag gatgtgacct acgcccagct gcacagcttg 1860
accctcagac gggaggcaac tgagcctcct ccatcccagg aagggccctc tccagctgtg 1920
cccagcatct acgccactct ggccatccac                                 1950

SEQ ID NO: 29            moltype = AA  length = 650
FEATURE                  Location/Qualifiers
source                   1..650
                         mol_type = protein
                         organism = Homo sapiens
SEQUENCE: 29
MTPILTVLIC LGLSLGPRTH VQAGHLPKPT LWAEPGSVIT QGSPVTLRCQ GGQETQEYRL   60
YREKKTAPWI TRIPQELVKK GQFPIPSITW EHTGRYRCYY GSDTAGRSES SDPLELVVTG  120
AYIKPTLSAQ PSPVVNSGGN VTLQCDSQVA FDGFILCKEG EDEHPQCLNS QPHARGSSRA  180
IFSVGPVSPS RRWWYRCYAY DSNSPYEWSL PSDLLELLVL GVSKKPSLSV QPGPIVAPEE  240
TLTLQCGSDA GYNRFVLYKD GERDFLQLAG AQPQAGLSQA NFTLGPVSRS YGGQYRCYGA  300
HNLSSEWSAP SDPLDILIAG QFYDRVSLSV QPGPTVASGE NVTLLCQSQG WMQTFLLTKE  360
GAADDPWRLR STYQSQKYQA EFPMGPVTSA HAGTYRCYGS QSSKPYLLTH PSDPLELVVS  420
GPSGGPSSPT TGPTSTSGPE DQPLTPTGSD PQSGLGRHLG VVIGILVAVI LLLLLLLLLF  480
LILRHRRQGK HWTSTQRKAD FQHPAGAVGP EPTDRGLQWR SSPAADAQEE NLYAAVKHTQ  540
PEDGVEMDTR SPHDEDPQAV TYAEVKHSRP RREMASPPSP LSGEFLDTKD RQAEEDRQMD  600
TEAAASEAPQ DVTYAQLHSL TLRREATEPP PSQEGPSPAV PSIYATLAIH              650

SEQ ID NO: 30            moltype = DNA  length = 1464
FEATURE                  Location/Qualifiers
source                   1..1464
                         mol_type = other DNA
                         organism = synthetic construct
SEQUENCE: 30
atgacccca tcctcacggt cctgatctgt ctcgggctga gtctgggccc ccggacccac    60
```

```
gtgcaggcag ggcacctccc caagcccacc ctctgggctg aaccaggctc tgtgatcacc    120
cagggagtc ctgtgaccct caggtgtcag gggggccagg agacccagga gtaccgtcta    180
tatagagaaa agaaaacagc accctggatt acacggatcc cacaggagct tgtgaagaag    240
ggccagttcc ccatcccatc catcacctgg aacacacag ggcggtatcg ctgttactat    300
ggtgcgaca ctgcaggccg ctcagagagc agtgaccccc tggagctggt ggtgacagga    360
gcctacatca aacccaccct ctcagccag cccagcccg tggtgaactc aggagggaat    420
gtaaccctcc agtgtgactc acaggtggca tttgatgcct tcattctgtg taaggaagga    480
gaagatgaac cccacaatg cctgaactcc cagcccatg cccgtgggtc gtcccgcgcc    540
atcttctccg tgggcccccgt gagcccgagt cgcaggtggt ggtacaggtg ctatgcttat    600
gactcgaact ctcccatga gtggtctcta cccagtgatc tcctggagct cctggtccta    660
ggtgtttcta agaagccatc actctcagtg cagccaggtc ctatcgtggc ccctgaggag    720
acctgactc tgcagtgtgg ctctgatgct ggctacaaca gatttgttct gtataaggac    780
ggggaacgtg acttccttca gctcgctggc gcacagcccc aggctgggct ctcccaggcc    840
aacttcaccc tgggccctgt gagccgctcc tacggggcc agtacagatg ctacggtgga    900
cacaacctct cctccgagtg gtcggccccc agcgacccct ggacatcct gatcgcagga    960
cagttctatg acagagtctc cctctcggtg cagccgggcc ccacggtggc ctcaggagag   1020
aacgtgaccc tgctgtgtca gtcacaggga tggatgcaaa cttccttct gaccaaggag   1080
ggggcagctg atgacccatg gcgtctaaga tcaacgtacc aatctcaaaa ataccaggct   1140
gaattcccca tgggtcctgt gacctcagcc catgcgggga cctacaggtg ctacggctca   1200
cagagctcca aacccacct gctgactcac cccagtgacc cctggagct cgtggtctca   1260
ggaccgtctg ggggccccag ctccccgaca acaggcccca cctccacatc tggccctgag   1320
gaccagcccc tcaccccac cgggtcggat cccagagtg gtctgggaag gcaccctggg   1380
gttgtgatcg gcatcttggt ggccgtcatc ctactgctcc tcctcctcct cctcctcttc   1440
ctcatcctcc gacatcgacg tcag                                          1464

SEQ ID NO: 31          moltype = AA  length = 488
FEATURE                Location/Qualifiers
source                 1..488
                       mol_type = protein
                       organism = synthetic construct
SEQUENCE: 31
MTPILTVLIC LGLSLGPRTH VQAGHLPKPT LWAEPGSVIT QGSPVTLRCQ GGQETQEYRL    60
YREKKTAPWI TRIPQELVKK GQFPIPSITW EHTGRYRCYY GSDTAGRSES SDPLELVVTG   120
AYIKPTLSAQ PSPVVNSGGN VTLQCDSQVA FDGFILCKEG EDEHPQCLNS QPHARGSSRA   180
IFSVGPVSPS RRWWYRCYAY DSNSPYEWSL PSDLLELLVL GVSKKPSLSV QPGPIVAPEE   240
TLTLQCGSDA GYNRFVLYKD GERDFLQLAG AQPQAGLSQA NFTLGPVSRS YGGQYRCYGA   300
HNLSSEWSAP SDPLDILIAG QFYDRVSLSV QPGPTVASGE NVTLLCQSQG WMQTFLLTKE   360
GAADDPWRLR STYQSQKYQA EFPMGPVTSA HAGTYRCYGS QSSKPYLLTH PSDPLELVVS   420
GPSGGPSSPT TGPTSTSGPE DQPLTPTGSD PQSGLGRHLG VVIGILVAVI LLLLLLLLLF   480
LILRHRRQ                                                            488

SEQ ID NO: 32          moltype = DNA  length = 336
FEATURE                Location/Qualifiers
source                 1..336
                       mol_type = other DNA
                       organism = synthetic construct
SEQUENCE: 32
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaa ttgggatgaa aggcgagcgc   240
cggaggggca aggggcacga tggccttac cagggtctca gtacagccac caaggacacc   300
tacgacgccc ttcacatgca agctcttcca cctcgt                              336

SEQ ID NO: 33          moltype = AA  length = 112
FEATURE                Location/Qualifiers
source                 1..112
                       mol_type = protein
                       organism = synthetic construct
SEQUENCE: 33
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 34          moltype = DNA  length = 126
FEATURE                Location/Qualifiers
source                 1..126
                       mol_type = other DNA
                       organism = synthetic construct
SEQUENCE: 34
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

SEQ ID NO: 35          moltype = AA  length = 42
FEATURE                Location/Qualifiers
source                 1..42
                       mol_type = protein
                       organism = synthetic construct
SEQUENCE: 35
```

```
KRGRKKLLYI FKQPFMRPVQ TTQEEDGCSC RFPEEEEGGC EL                        42

SEQ ID NO: 36              moltype = DNA   length = 664
FEATURE                    Location/Qualifiers
source                     1..664
                           mol_type = other DNA
                           organism = synthetic construct
SEQUENCE: 36
atgaccccca tcctcacggt cctgatctgt ctcgggctga gtctgggccc ccggacccac      60
gtgcaggcag ggcacctccc caagcccacc ctctgggctg aaccaggctc tgtgatcacc     120
caggggagtc ctgtgaccct caggtgtcag ggggccagg agaccagga gtaccgtcta      180
tatagagaaa agaaaacagc accctggatt acacggatcc cacaggagct tgtgaagaag     240
ggccagttcc ccatcccatc catcacctgg aacacacag ggcggtatcg ctgttactat      300
ggtagcgaca ctgcaggccg ctcagagagc agtgaccccc tggagctggt ggtgacagga     360
gcctacatca aacccaccct ctcagcccag cccagcccg tggtgaactc aggagggaat     420
gtaaccctcc agtgtgactc acaggtggca tttgatggct tcattctgtg taaggaagga     480
gaagatgaac cccacaatgc ctgaactcc cagcccatg cccgtgggtc gtcccgcgcc      540
atcttctccg tgggccccgt gagcccgagt cgcaggtggt ggtacaggtg ctatgcttat     600
gactcgaact ctccctatga gtggtctcta cccagtgatc tcctggagct cctggtccta     660
ggtg                                                                  664

SEQ ID NO: 37              moltype = AA    length = 198
FEATURE                    Location/Qualifiers
source                     1..198
                           mol_type = protein
                           organism = synthetic construct
SEQUENCE: 37
MHLPKPTLWA EPGSVITQGS PVTLRCQGGQ ETQEYRLYRE KKTAPWITRI PQELVKKGQF      60
PIPSITWEHT GRYRCYYGSD TAGRSESSDP LELVVTGAYI KPTLSAQPSP VVNSGGNVTL    120
QCDSQVAFDG FILCKEGEDE HPQCLNSQPH ARGSSRAIFS VGPVSPSRRW WYRCYAYDSN    180
SPYEWSLPSD LLELLVLG                                                  198

SEQ ID NO: 38              moltype = DNA   length = 213
FEATURE                    Location/Qualifiers
source                     1..213
                           mol_type = other DNA
                           organism = synthetic construct
SEQUENCE: 38
gtggtctcag gaccgtctgg gggccccagc tccccgacaa caggcccac ctccacatct       60
ggccctgagg accagcccct cacccccacc gggtcggatc cccagagtgg tctgggaagg    120
cacctggggg ttgtgatcgg catcttggtg gccgtcatcc tactgctcct cctcctcctc    180
ctcctcttcc tcatcctccg acatcgacgt cag                                 213

SEQ ID NO: 39              moltype = AA    length = 71
FEATURE                    Location/Qualifiers
source                     1..71
                           mol_type = protein
                           organism = synthetic construct
SEQUENCE: 39
VVSGPSGGPS SPTTGPTSTS GPEDQPLTPT GSDPQSGLGR HLGVVIGILV AVILLLLLLL      60
LLFLILRHRR Q                                                          71

SEQ ID NO: 40              moltype = DNA   length = 48
FEATURE                    Location/Qualifiers
source                     1..48
                           mol_type = other DNA
                           organism = synthetic construct
SEQUENCE: 40
gaacttccta ctcaggggac tttctcaaac gttagcacaa acgtaagt                   48

SEQ ID NO: 41              moltype = AA    length = 16
FEATURE                    Location/Qualifiers
source                     1..16
                           mol_type = protein
                           organism = synthetic construct
SEQUENCE: 41
ELPTQGTFSN VSTNVS                                                      16

SEQ ID NO: 42              moltype = DNA   length = 237
FEATURE                    Location/Qualifiers
source                     1..237
                           mol_type = other DNA
                           organism = synthetic construct
SEQUENCE: 42
cccgccccaa gacccccac acctgcgccg accattgctt ctcaacccct gagtttgaga       60
cccgaggcct gccggccagc tgccggcggg gccgtgcata caagaggact cgatttcgct    120
tgcgacatct atatctgggc acctctcgct ggcacctgtg gagtccttct gctcagcctg    180
gttattactc tgtactgtaa tcaccggaat cgccgccgcg tttgtaagtg tcccagg       237
```

```
SEQ ID NO: 43            moltype = AA   length = 79
FEATURE                  Location/Qualifiers
source                   1..79
                         mol_type = protein
                         organism = synthetic construct
SEQUENCE: 43
PAPRPPTPAP TIASQPLSLR PEACRPAAGG AVHTRGLDFA CDIYIWAPLA GTCGVLLLSL   60
VITLYCNHRN RRRVCKCPR                                               79

SEQ ID NO: 44            moltype = DNA   length = 1014
FEATURE                  Location/Qualifiers
source                   1..1014
                         mol_type = other DNA
                         organism = synthetic construct
SEQUENCE: 44
atggtggtca tggcaccccg aaccctcttc ctgctactct cggggggccct gaccctgacc   60
gagacctggg cgggctccca ctccatgagg tatttcagcg ccgccgtgtc ccggcccggc  120
cgcggggagc cccgcttcat cgccatgggc tacgtggacg acacgcagtt cgtgcggttc  180
gacagcgact cggcgagtcc gaggatgagc cgcgggcgc cgtgggtgga gcaggagggg   240
ccagagtatt gggaagagga gacacggaac accaaggccc acgcacagac tgacagaatg  300
aacctgcaga cccctgcgcgg ctactacaac cagagcgagg ccagttctca caccctccag  360
tggatgattg gctgcgacct ggggtccgac ggacgcctca tccgcgggta tgaacggtat  420
gcctacgatg gcaaggatta cctcgccctg aacgaggacc tgcgctcctg gaccgcagcg  480
gacactgcgg ctcagatctc caagcgcaag agtgaggcgg ccaatgtggc tgaacaaagg  540
agagcctacc tggagggcac gtgcgtggag tggctccaca gatacctgga acgggaag    600
gagatgctgc agcgcgcgga ccccccccaag acacacgtga cccaccaccc tgtctttgac  660
tatgaggcca ccctgaggtg ctgggccctg gccttctacc ctgcggagat catactgacc  720
tggcagcggg atggggagga ccagacccag gacgtggagc tcgtggagac caggcctgca  780
ggggatggaa ccttccagaa gtgggcagct gtggtggtgc cttctggaga ggagcagaga  840
tacacgtgcc atgtgcagca tgagggggctg ccggagcccc tcatgctgat gtggaagcag  900
tcttccctgc ccaccatccc catcatgggg atcgttgctg gcctggttgt ccttgcagct  960
gtagtcactg gagctgcggt cgctgctgtg ctgtggagga agaagagctc agat       1014

SEQ ID NO: 45            moltype = AA   length = 338
FEATURE                  Location/Qualifiers
source                   1..338
                         mol_type = protein
                         organism = synthetic construct
SEQUENCE: 45
MVVMAPRTLF LLLSGALTLT ETWAGSHSMR YFSAAVSRPG RGEPRFIAMG YVDDTQFVRF   60
DSDSASPRME RPAPWVEQEG PEYWEEETRN TKAHAQTDRM NLQTLRGYYN QSEASSHTLQ  120
WMIGCDLGSD GRLIRGYERY AYDGKDYLAL NEDLRSWTAA DTAAQISKRK SEAANVAEQR  180
RAYLEGTCVE WLHRYLENGK EMLQRADPPK THVTHHPVFD YEATLRCWAL GFYPAEIILT  240
WQRDGEDQTQ DVELVETRPA GDGTFQKWAA VVVPSGEEQR YTCHVQHEGL PEPLMLRWKQ  300
SSLPTIPIMG IVAGLVVLAA VVTGAAVAAV LWRKKSSD                         338

SEQ ID NO: 46            moltype = DNA   length = 198
FEATURE                  Location/Qualifiers
source                   1..198
                         mol_type = other DNA
                         organism = synthetic construct
SEQUENCE: 46
attgaagtta tgtatcctcc tccttaccta gacaatgaga agagcaatgg aaccattatc   60
catgtgaaag ggaaacacct ttgtccaagt cccctatttc ccggaccttc taagcccttt  120
tgggtgctgg tggtggttgg gggagtcctg gcttgctata gcttgctagt aacagtggcc  180
tttatttatt tctgggtg                                                198

SEQ ID NO: 47            moltype = AA   length = 66
FEATURE                  Location/Qualifiers
source                   1..66
                         mol_type = protein
                         organism = synthetic construct
SEQUENCE: 47
IEVMYPPPYL DNEKSNGTII HVKGKHLCPS PLFPGPSKPF WVLVVVGGVL ACYSLLVTVA   60
FIIFWV                                                              66

SEQ ID NO: 48            moltype = DNA   length = 105
FEATURE                  Location/Qualifiers
source                   1..105
                         mol_type = other DNA
                         organism = synthetic construct
SEQUENCE: 48
ctcctccatt ccgattatat gaacatgaca cctcgccgac ctggtcctac acgcaaacat   60
tatcaaccct acgcaccccc ccgagacttc gctgcttatc gatcc                 105

SEQ ID NO: 49            moltype = AA   length = 35
FEATURE                  Location/Qualifiers
source                   1..35
                         mol_type = protein
```

```
                              organism = synthetic construct
SEQUENCE: 49
LLHSDYMNMT PRRPGPTRKH YQPYAPPRDF AAYRS                                35

SEQ ID NO: 50             moltype = DNA   length = 795
FEATURE                   Location/Qualifiers
source                    1..795
                          mol_type = other DNA
                          organism = synthetic construct
SEQUENCE: 50
gatccagccg aacccaaatc ccccgataaa acacatactt gcccccttg tcccgcacca       60
gaattgcttg gcggaccttc cgttttcct tttcccccca aacctaaaga taccctgatg      120
atttcccgaa ccctgaagt tacgtgcgta gtcgtagatg tgtctcacga agatccagaa      180
gtaaaattta actggtacgt agatggagtc gaagttcaca acgcaaagac gaagccccga     240
gaagaacaat ataattccac ataccgagta gttagcgttc tcaccgtact gcatcaggac     300
tggcttaacg gcaaagaata taaatgtaag gtctcaaaca aagcactccc agccctatc     360
gaaaagacta tctccaaagc taaggacaa ccccgcgaac cccaggtcta tacttccc      420
ccctcacgcg atgaactcac taaaaatcag gtttcctta cttgtcttgt caaaggcttc     480
taccctagcg atatcgcagt cgaatggaa tccaatggcc agcccgaaaa caactataaa     540
acaaccccac ctgtcctcga ttcagatggc tcattctttc tctattccaa actgactgta     600
gacaaatccc gatggcaaca aggtaacgtg ttctcttgct cagtcatgca tgaagcgctt     660
cataaccatt acacacaaaa atctctctca ctgtctcccg gaaagaagga ccccttttgg     720
gtgctggtgg tggttggggg agtcctggct tgctatagct tgctagtaac agtggccttt     780
attattttct gggtg                                                      795

SEQ ID NO: 51             moltype = AA   length = 265
FEATURE                   Location/Qualifiers
source                    1..265
                          mol_type = protein
                          organism = synthetic construct
SEQUENCE: 51
DPAEPKSPDK THTCPPCPAP ELLGGPSVFL FPPKPKDTLM ISRTPEVTCV VVDVSHEDPE      60
VKFNWYVDGV EVHNAKTKPR EEQYNSTYRV VSVLTVLHQD WLNGKEYKCK VSNKALPAPI     120
EKTISKAKGQ PREPQVYTLP PSRDELTKNQ VSLTCLVKGF YPSDIAVEWE SNGQPENNYK     180
TTPPVLDSDG SFFLYSKLTV DKSRWQQGNV FSCSVMHEAL HNHYTQKSLS LSPGKKDPFW     240
VLVVVGGVLA CYSLLVTVAF IIFWV                                           265

SEQ ID NO: 52             moltype = DNA   length = 1794
FEATURE                   Location/Qualifiers
source                    1..1794
                          mol_type = unassigned DNA
                          organism = Homo sapiens
SEQUENCE: 52
atgaccccca tcgtcacagt cctgatctgt ctcgggctga gtctgggccc caggacccac      60
gtgcagacag ggaccatccc caagcccacc ctgtgggctg agccagactc tgtgatcacc     120
caggggagtc ccgtcaccct cagttgtcag gggagcttg aagcccagga gtaccgtcta     180
tatgggagga aaaaatcagc atcttggatt acacgtacg gaccagatct tgtgaagaac     240
ggccagttcc acatcccatc catcacctgg gaacacacag ggcgatatgg ctgtcagtat     300
tacagccgcg ctcggtggtc tgagctcagt gaccccctgg tgctggtgat gacaggagcc     360
tacccaaaac ccaccctctc agcccagccc agccctgtgg tgacctcagg aggaagggtg     420
accctccagt gtgagtcaca ggtggcattt ggcggcttca ttctgtgtaa gaaggagaa     480
gatgaacacc acaatgcct gaactcccag cccatgccc gtgggtcgtc ccgcgccatc     540
ttctccgtgg gccccgtgag cccgaatcgc aggtggtcgc acaggtgcta tggttatgac     600
ttgaactctc cctatgtgtg gtcttcaccc agtgatctcc tggagctcct ggtcccaggt     660
gtttctaaga agccatcact ctcagtgcag ccgggtcctg tcatggccc tggggaaagc     720
ctgaccctcc agtgtgtctc tgatgtcggc tatgacagat ttgttctgta caaggagggg     780
gaacgtgacc ttcgccagct ccctggccgg cagcccagg ctgggctctc ccaggccaac     840
ttcaccctgg gcctgtgag ccgctcctac ggggccagt acagatgcta cggtgcacac      900
aacctctcct ctgagtgctc ggcccccagc gacccctgg acatcctgat cacaggacag     960
atccgtggca caccttcat ctcagtgcag ccaggcccca cagtggcctc aggagagaac    1020
gtgaccctgc tgtgtcagtc atggcggcag ttccacactt tccttctgac caaggcggga    1080
gcagctgatg ccccactccg tctaagatca atacacgaat atcctaagta ccaggctgaa    1140
ttccccatga gtcctgtgac ctcagcccac gcggggacct acaggtgcta cggctcactc    1200
aactccgacc cctacctgct gtctcaccc agtgagctgt ggtctcagga                1260
ccctccatgg gttccagccc ccacccacc ggtccatct ccacacctgc aggccctgag     1320
gaccagcccc tcacccccac tgggtcgat cccaaagtg gtctgggaag cacctgggg     1380
gttgtgatcg gcatcttggt ggccgtcgtc tactgctcc tcctcctcct cctcctcttc    1440
ctcatcctcc gacatcgacg tcagggcaaa cactggacat cgacccagga aaaggctgat    1500
ttccaacatc ctgcaggggc tgtggggcca gagcccacag acagaggcct gcagtggagg    1560
tccagcccag ctgccgacgc ccaggaagaa aacctctatg ctgccgtgaa ggacacacag    1620
cctgaagatg gggtggagat ggacactcgg gctgctgcat ctgaagcccc caggatgtg    1680
acctacgccc agctgcacag cttgaccctc agacggaagg caactgagcc tcctccatcc    1740
caggaaaggg aacctccagc tgagcccagc atctacgcca cctgccat ccac           1794

SEQ ID NO: 53             moltype = AA   length = 598
FEATURE                   Location/Qualifiers
source                    1..598
                          mol_type = protein
                          organism = Homo sapiens
```

```
SEQUENCE: 53
MTPIVTVLIC LGLSLGPRTH VQTGTIPKPT LWAEPDSVIT QGSPVTLSCQ GSLEAQEYRL    60
YREKKSASWI TRIRPELVKN GQFHIPSITW EHTGRYGCQY YSRARWSELS DPLVLVMTGA   120
YPKPTLSAQP SPVVTSGGRV TLQCESQVAF GGFILCKEGE DEHPQCLNSQ PHARGSSRAI   180
FSVGPVSPNR RWSHRCYGYD LNSPYVWSSP SDLLELLVPG VSKKPSLSVQ PGPVMAPGES   240
LTLQCVSDVG YDRFVLYKEG ERDLRQLPGR QPQAGLSQAN FTLGPVSRSY GGQYRCYGAH   300
NLSSECSAPS DPLDILITGQ IRGTPFISVQ PGPTVASGEN VTLLCQSWRQ FHTFLLTKAG   360
AADAPLRLRS IHEYPKYQAE FPMSPVTSAH AGTYRCYGSL NSDPYLLSHP SEPLELVVSG   420
PSMGSSPPPT GPISTPAGPE DQPLTPTGSD PQSGLGRHLG VVIGILVAVV LLLLLLLLFL   480
LILRHRRQGK HWTSTQRKAD FQHPAGAVGP EPTDRGLQWR SSPAADAQEE NLYAAVKDTQ   540
PEDGVEMDTR AAASEAPQDV TYAQLHSLTL RRKATEPPPS QEREPPAEPS IYATLAIH     598

SEQ ID NO: 54           moltype = DNA  length = 1464
FEATURE                 Location/Qualifiers
source                  1..1464
                        mol_type = other DNA
                        organism = synthetic construct
SEQUENCE: 54
atgaccccca tcgtcacagt cctgatctgt ctcgggctga gtctgggccc caggacccac    60
gtgcagacag ggaccatccc caagcccacc ctgtgggctg agccagactc tgtgatcacc   120
caggggagtc ccgtcaccct cagttgtcag gggagccttg aagcccagga gtaccgtcta   180
tagggagaa aaaaatcagc atcttggatt acacggatgc tgtgaagaac   240
ggccagttcc acatcccatc catcacctgg aacacacag ggcgatatgg ctgtcagtat   300
tacagccgcg ctcggtggtc tgagctcagt gaccccctgg tgctggtgat gacaggagcc   360
tacccaaaac ccacccctc agcccagccc agccctgtgg tgacctcagg aggaagggtg   420
accctccagt gtgagtcaca ggtggcattt ggcggcttca ttctgtgtaa ggaaggagaa   480
gatgaacacc cacaatgcct gaactccag ccccatgccc gtgggtcgtc ccgcgccatc   540
ttctccgtgg gccccgtgag cccgaatcgc aggtggtcgc acaggtgcta tggttatgac   600
ttgaactctc cctatgtgtg gtcttcaccc agtgatctcc tggagctcct ggtcccaggt   660
gtttctaaga agccatcact ctcagtgcag ccgggtcctg tcatggcccc tggggaaagc   720
ctgaccctcc agtgtgtctc tgatgtcggc tatgacagat ttgttctgta caaggagggg   780
gaacgtgacc ttcgcagct ccctggccgg cagcccagg ctgggctctc ccaggccaac   840
ttcaccctgg gcctgtgag ccgctcctac ggggccagt acagatgcta cggtgcacac   900
aacctctcct ctgagtgctc ggcccccagc gaccccctgg acatcctgat cacaggacag   960
atccgtggca cacccttcat ctcagtgcag ccaggcccca cagtggcctc aggagagaac  1020
gtgaccctgc tgtgtcagtc atggcggcag ttccacactt tccttctgac caaggcggga  1080
gcagctgatg ccccactccg tctaagatca atacacgaat atcctaagta ccaggctgaa  1140
ttccccatga gtcctgtgac ctcagcccac gcggggacct acaggtgcta cggctcactc  1200
aactccgac cctacctgct gtctcaccc agtgagcccc tggagctcgt ggtctcagga  1260
ccctccatgg gttccagccc cccacccacc ggtcccatct ccacacctgc aggccctgag  1320
gaccagcccc tcaccccac tgggtcggat ccccaaagtg gtctgggaag caccctgggg  1380
gttgtgatcg gcatcttggt ggccgtcgtc ctactgctcc tcctcctcct cctcctcttc  1440
ctcatcctcc gacatcgacg tcag                                         1464

SEQ ID NO: 55           moltype = AA  length = 488
FEATURE                 Location/Qualifiers
source                  1..488
                        mol_type = protein
                        organism = synthetic construct
SEQUENCE: 55
MTPIVTVLIC LGLSLGPRTH VQTGTIPKPT LWAEPDSVIT QGSPVTLSCQ GSLEAQEYRL    60
YREKKSASWI TRIRPELVKN GQFHIPSITW EHTGRYGCQY YSRARWSELS DPLVLVMTGA   120
YPKPTLSAQP SPVVTSGGRV TLQCESQVAF GGFILCKEGE DEHPQCLNSQ PHARGSSRAI   180
FSVGPVSPNR RWSHRCYGYD LNSPYVWSSP SDLLELLVPG VSKKPSLSVQ PGPVMAPGES   240
LTLQCVSDVG YDRFVLYKEG ERDLRQLPGR QPQAGLSQAN FTLGPVSRSY GGQYRCYGAH   300
NLSSECSAPS DPLDILITGQ IRGTPFISVQ PGPTVASGEN VTLLCQSWRQ FHTFLLTKAG   360
AADAPLRLRS IHEYPKYQAE FPMSPVTSAH AGTYRCYGSL NSDPYLLSHP SEPLELVVSG   420
PSMGSSPPPT GPISTPAGPE DQPLTPTGSD PQSGLGRHLG VVIGILVAVV LLLLLLLLF    480
LILRHRRQ                                                           488

SEQ ID NO: 56           moltype = DNA  length = 660
FEATURE                 Location/Qualifiers
source                  1..660
                        mol_type = other DNA
                        organism = synthetic construct
SEQUENCE: 56
atgaccccca tcgtcacagt cctgatctgt ctcgggctga gtctgggccc caggacccac    60
gtgcagacag ggaccatccc caagcccacc ctgtgggctg agccagactc tgtgatcacc   120
caggggagtc ccgtcaccct cagttgtcag gggagccttg aagcccagga gtaccgtcta   180
tagggagaa aaaaatcagc atcttggatt acacggatgc tgtgaagaac   240
ggccagttcc acatcccatc catcacctgg aacacacag ggcgatatgg ctgtcagtat   300
tacagccgcg ctcggtggtc tgagctcagt gaccccctgg tgctggtgat gacaggagcc   360
tacccaaaac ccacccctc agcccagccc agccctgtgg tgacctcagg aggaagggtg   420
accctccagt gtgagtcaca ggtggcattt ggcggcttca ttctgtgtaa ggaaggagaa   480
gatgaacacc cacaatgcct gaactccag ccccatgccc gtgggtcgtc ccgcgccatc   540
ttctccgtgg gccccgtgag cccgaatcgc aggtggtcgc acaggtgcta tggttatgac   600
ttgaactctc cctatgtgtg gtcttcaccc agtgatctcc tggagctcct ggtcccaggt   660

SEQ ID NO: 57           moltype = AA  length = 220
```

```
FEATURE                 Location/Qualifiers
source                  1..220
                        mol_type = protein
                        organism = synthetic construct
SEQUENCE: 57
MTPIVTVLIC LGLSLGPRTH VQTGTIPKPT LWAEPDSVIT QGSPVTLSCQ GSLEAQEYRL    60
YREKKSASWI TRIRPELVKN GQFHIPSITW EHTRYGCQY  YSRARWSELS DPLVLVMTGA   120
YPKPTLSAQP SPVVTSGGRV TLQCESQVAF GGFILCKEGE DEHPQCLNSQ PHARGSSRAI   180
FSVGPVSPNR RWSHRCYGYD LNSPYVWSSP SDLLELLVPG                        220

SEQ ID NO: 58           moltype = DNA  length = 216
FEATURE                 Location/Qualifiers
source                  1..216
                        mol_type = other DNA
                        organism = synthetic construct
SEQUENCE: 58
gtggtctcag gaccctccat gggttccagc cccccaccca ccggtcccat ctccacacct    60
gcaggccctg aggaccagcc cctcacccce actgggtcgg atccccaaag tggtctggga   120
aggcacctgg gggttgtgat cggcatcttg gtggccgtcg tcctactgct cctcctcctc   180
ctcctcctct tcctcatcct ccgacatcga cgtcag                            216

SEQ ID NO: 59           moltype = AA  length = 72
FEATURE                 Location/Qualifiers
source                  1..72
                        mol_type = protein
                        organism = synthetic construct
SEQUENCE: 59
VVSGPSMGSS PPPTGPISTP AGPEDQPLTP TGSDPQSGLG RHLGVVIGIL VAVVLLLLLL    60
LLLFLILRHR RQ                                                       72

SEQ ID NO: 60           moltype = DNA  length = 1464
FEATURE                 Location/Qualifiers
source                  1..1464
                        mol_type = other DNA
                        organism = synthetic construct
SEQUENCE: 60
atgacccca tcgtcacagt cctgatctgt ctcgggctga gtctgggccc caggacccac     60
gtgcagacag gaccatccc caagcccacc ctgtgggctg agccagactc tgtgatcacc    120
cagggagtc ccgtcaccct cagttgtcag gggagccttg aagcccagga gtaccgtcta   180
tatagggaga aaaaatcagc atcttggatt acacggatac gaccagagct tgtgaagaac   240
ggccagttcc acatcccatc catcacctgg gaacacacag gcgatatgg ctgtcagtat   300
tacagccgcg ctcggtggtc tgagctcagt gaccccctgg tgctggtgat gacaggagcc   360
tacccaaaac ccaccctctc agcccagccc agccctgtgg tgacctcagg aggaagggtg   420
accctccagt gtgagtcaca ggtggcattt ggcggcttca ttctgtgtaa ggaaggagaa   480
gatgaacacc cacaatgcct gaactcccag ccccatgccc gtgggtcgtc ccgcgccatc   540
ttctccgtgg gccccgtgag cccgaatcgc aggtggtcgc acaggtgcta tggttatgac   600
ttgaactctc cctatgtgtg gtcttcaccc agtgatctcc ttgagctcct ggtcccaggt   660
gtttctaaga agccatcact ctcagtgcag ccgggtcctg tcatggcccc tgggaaagc   720
ctgaccctcc agtgtgtctc tgatgtcggc tatgacagat ttgttctgta caaggagggg   780
gaacgtgacc ttcgccagct ccctggccgg cagcccagg ctgggctctc ccaggccaac   840
ttcacctgg gccctgtgag ccgctcctac gggggcaggt acagatgca cggtgcacac   900
aacctctcct ctgagtgctc ggccccagc gaccccctgg acatcctgat cacaggacag   960
atccgtggca caccccttcat ctcagtgcag ccaggcccca cagtggcctc aggagagaac  1020
gtgacccctg tgtgtcagtc atggcggcag ttccacactt tccttctgac caaggcggga  1080
gcagctgatg ccccactccg tctaagatca atacacgaat atcctaagta ccaggctgaa  1140
ttccccatga gtcctgtgac ctcagccac gcggggaccg caaggtgcta cggctcactc   1200
aactccgacc cctacctgct gtctcacccc agtgagcccc tggagctcgt ggtctcagga  1260
ccctccatgg gttccagcc cccacccacc ggtcccatct ccacacctgc aggccctgag   1320
gaccagcccc tcacccccac tgggtcggat cccaaagtg tgtgggaag cacctgggg    1380
gttgtgatcg gcatcttggt ggccgtcgtc tactgctcc tcctcctcct cctcctcttc  1440
ctcatcctcc gacatcgacg tcag                                         1464

SEQ ID NO: 61           moltype = AA  length = 488
FEATURE                 Location/Qualifiers
source                  1..488
                        mol_type = protein
                        organism = synthetic construct
SEQUENCE: 61
MTPIVTVLIC LGLSLGPRTH VQTGTIPKPT LWAEPDSVIT QGSPVTLSCQ GSLEAQEYRL    60
YREKKSASWI TRIRPELVKN GQFHIPSITW EHTRYGCQY  YSRARWSELS DPLVLVMTGA   120
YPKPTLSAQP SPVVTSGGRV TLQCESQVAF GGFILCKEGE DEHPQCLNSQ PHARGSSRAI   180
FSVGPVSPNR RWSHRCYGYD LNSPYVWSSP SDLLELLVPG VSKKPSLSVQ PGPVMAPGES   240
LTLQCVSDVG YDRFVLYKEG ERDLRQLPGR QPQAGLSQAN FTLGPVSRSY GGQYRCYGAH   300
NLSSECSAPS DPLDILITGQ IRGTPFISVQ PGPTVASGEN VTLLCQSWRQ FHTFLLTKAG   360
AADAPLRLRS IHEYPKYQAE FPMSPVTSAH AGTARCYGSL NSDPYLLSHP SEPLELVVSG   420
PSMGSSPPPT GPISTPAGPE DQPLTPTGSD PQSGLGRHLG VVIGILVAVV LLLLLLLLLF   480
LILRHRRQ                                                            488

SEQ ID NO: 62           moltype = DNA  length = 660
```

| FEATURE | Location/Qualifiers |
|---|---|
| source | 1..660<br>mol_type = other DNA<br>organism = synthetic construct |

SEQUENCE: 62

```
atgacccca tcgtcacagt cctgatctgt ctcgggctga gtctgggccc caggacccac   60
gtgcagacag ggaccatccc caagcccacc ctgtgggctg agccagactc tgtgatcacc  120
caggggagtc ccgtcaccct cagttgtcag gggagccttg aagcccagga gtaccgtcta  180
tatagggaga aaaaatcagc atcttggatt acacggatac gaccagagct tgtgaagaac  240
ggccagttcc acatcccatc catcacctgg gaacacacag ggcgagcagg ctgtcagtat  300
tacagccgcg ctcggtggtc tgagctcagt gaccccctgg tgctggtgat gacaggagcc  360
tacccaaaac ccaccctctc agcccagccc agccctgtgg tgacctcagg aggaaggtg  420
accctccagt gtgagtcaca ggtggcattt ggcggcttca ttctgtgtaa ggaaggagaa  480
gatgaacacc cacaatgcct gaactcccag ccccatgccc gtgggcgtc ccgcgccatc   540
ttctccgtgg gccccgtgag cccgaatcgc aggtggtcgc acaggtgcta tggttatgac  600
ttgaactctc cctatgtgtg gtcttcaccc agtgatctcc tggagctcct ggtcccaggt  660
```

| SEQ ID NO: 63 | moltype = AA length = 220 |
|---|---|
| FEATURE | Location/Qualifiers |
| source | 1..220<br>mol_type = protein<br>organism = synthetic construct |

SEQUENCE: 63

```
MTPIVTVLIC LGLSLGPRTH VQTGTIPKPT LWAEPDSVIT QGSPVTLSCQ GSLEAQEYRL   60
YREKKSASWI TRIRPELVKN GQFHIPSITW EHTGRAGCQY YSRARWSELS DPLVLVMTGA  120
YPKPTLSAQP SPVVTSGGRV TLQCESQVAF GGFILCKEGE DEHPQCLNSQ PHARGSSRAI  180
FSVGPVSPNR RWSHRCYGYD LNSPYVWSSP SDLLELLVPG                       220
```

| SEQ ID NO: 64 | moltype = DNA length = 603 |
|---|---|
| FEATURE | Location/Qualifiers |
| source | 1..603<br>mol_type = other DNA<br>organism = synthetic construct |

SEQUENCE: 64

```
cgcgtcatca tcgatccgga ttagtccaat ttgttaaaga caggatatca gtggtccagg   60
ctctagtttt gactcaacaa tatcaccagc tgaagcctat agagtacgag ccatagataa  120
aataaaagat tttatttagt ctccagaaaa agggggaat gaaagacccc acctgtaggt   180
ttggcaagct agcttaagta acgccatttt gcaaggcatg gaaaaataca taactgagaa  240
tagagaagtt cagatcaagg tcaggaacag atggaacagc tgaatatggg ccaaacagga  300
tatctgtggt aagcagttcc tgccccggct cagggccaag aacagatgga acagctgaat  360
atgggccaaa caggatatct gtggtaagca gttcctgccc cggctcaggg ccaagaacag  420
atggtcccca gatgcggtcc agccctcagc agtttctaga gaaccatcag atgtttccag  480
ggtgcccaa ggacctgaaa tgaccctgtg ccttatttga actaaccaat cagttcgctt    540
ctcgcttctg ttcgcgcgct tctgctcccc gagctcaata aaagagccca caaccccca  600
ctc                                                              603
```

| SEQ ID NO: 65 | moltype = DNA length = 147 |
|---|---|
| FEATURE | Location/Qualifiers |
| source | 1..147<br>mol_type = other DNA<br>organism = synthetic construct |

SEQUENCE: 65

```
ggggcgccag tcctccgatt gactgagtcg cccgggtacc cgtgtatcca ataaaccctc   60
ttgcagttgc atccgacttg tggtctcgct gttccttggg agggtctcct ctgagtgatt  120
gactaccgt cagcgggggt ctttcac                                      147
```

| SEQ ID NO: 66 | moltype = DNA length = 15 |
|---|---|
| FEATURE | Location/Qualifiers |
| source | 1..15<br>mol_type = other DNA<br>organism = synthetic construct |

SEQUENCE: 66

```
ccgcggggca gtgga                                                   15
```

| SEQ ID NO: 67 | moltype = AA length = 5 |
|---|---|
| FEATURE | Location/Qualifiers |
| source | 1..5<br>mol_type = protein<br>organism = synthetic construct |

SEQUENCE: 67

```
PRGSG                                                               5
```

| SEQ ID NO: 68 | moltype = AA length = 5 |
|---|---|
| FEATURE | Location/Qualifiers |
| source | 1..5<br>mol_type = protein<br>organism = synthetic construct |

SEQUENCE: 68

```
GSGPR                                                               5
```

```
SEQ ID NO: 69          moltype = AA   length = 16
FEATURE                Location/Qualifiers
source                 1..16
                       mol_type = protein
                       organism = synthetic construct
SEQUENCE: 69
MGSNKSKPKD ASQRRR                                                  16

SEQ ID NO: 70          moltype = AA   length = 198
FEATURE                Location/Qualifiers
source                 1..198
                       mol_type = protein
                       organism = synthetic construct
SEQUENCE: 70
MHLPKPTLWA EPGSVITQGS PVTLRCQGGQ ETQEYRLYRE KKTALWITRI PQELVKKGQF   60
PIPSITWEHA GRYRCYYGSD TAGRSESSDP LELVVTGAYI KPTLSAQPSP VVNSGGNVIL  120
QCDSQVAFDG FSLCKEGEDE HPQCLNSQPH ARGSSRAIFS VGPVSPSRRW WYRCYAYDSN  180
SPYEWSLPSD LLELLVLG                                               198

SEQ ID NO: 71          moltype = AA   length = 195
FEATURE                Location/Qualifiers
source                 1..195
                       mol_type = protein
                       organism = synthetic construct
SEQUENCE: 71
PKPTLWAEPG SVITQGSPVT LRCQGGQETQ EYRLYREKKT APWITRIPQE LVKKGQFPIP   60
SITWEHTGRY RCYYGSDTAG RSESSDPLEL VVTGAYIKPT LSAQPSPVVN SGGNVTLQCD  120
SQVAFDGFIL CKEGEDEHPQ CLNSQPHARG SSRAIFSVGP VSPSRRWWYR CYAYDSNSPY  180
EWSLPSDLLE LLVLG                                                  195

SEQ ID NO: 72          moltype = AA   length = 195
FEATURE                Location/Qualifiers
source                 1..195
                       mol_type = protein
                       organism = synthetic construct
SEQUENCE: 72
PKPTLWAEPG SVITQGSPVT LRCQGGQETQ EYRLYREKKT ALWITRIPQE LVKKGQFPIP   60
SITWEHAGRY RCYYGSDTAG RSESSDPLEL VVTGAYIKPT LSAQPSPVVN SGGNVILQCD  120
SQVAFDGFSL CKEGEDEHPQ CLNSQPHARG SSRAIFSVGP VSPSRRWWYR CYAYDSNSPY  180
EWSLPSDLLE LLVLG                                                  195

SEQ ID NO: 73          moltype = AA   length = 97
FEATURE                Location/Qualifiers
source                 1..97
                       mol_type = protein
                       organism = synthetic construct
SEQUENCE: 73
PLDILIAGQF YDRVSLSVQP GPTVASGENV TLLCQSQGWM QTFLLTKEGA ADDPWRLRST   60
YQSQKYQAEF PMGPVTSAHA GTYRCYGSQS SKPYLLT                            97

SEQ ID NO: 74          moltype = AA   length = 220
FEATURE                Location/Qualifiers
source                 1..220
                       mol_type = protein
                       organism = synthetic construct
SEQUENCE: 74
MTPIVTVLIC LGLSLGPRTR VQTGTIPKPT LWAEPDSVIT QGSPVTLSCQ GSLEAQEYRL   60
YREKKSASWI TRIRPELVKN GQFHIPSITW EHTGRYGCQY YSRARWSELS DPLVLVMTGA  120
YPKPTLSAQP SPVVTSGGRV TLQCESQVAF GGFILCKEGE DEHPQCLNSQ PHARGSSRAI  180
FSVGPVSPNR RWSHRCYGYD LNSPYVWSSP SDLLELLVPG                       220

SEQ ID NO: 75          moltype = AA   length = 194
FEATURE                Location/Qualifiers
source                 1..194
                       mol_type = protein
                       organism = synthetic construct
SEQUENCE: 75
PKPTLWAEPD SVITQGSPVT LSCQGSLEAQ EYRLYREKKS ASWITRIRPE LVKNGQFHIP   60
SITWEHTGRY GCQYYSRARW SELSDPLVLV MTGAYPKPTL SAQPSPVVTS GGRVTLQCES  120
QVAFGGFILC KEGEDEHPQC LNSQPHARGS SRAIFSVGPV SPNRRWSHRC YGYDLNSPYV  180
WSSPSDLLEL LVPG                                                   194

SEQ ID NO: 76          moltype = AA   length = 187
FEATURE                Location/Qualifiers
source                 1..187
                       mol_type = protein
                       organism = synthetic construct
SEQUENCE: 76
```

```
QPGPVMAPGE  SLTLQCVSDV  GYDRFVLYKE  GERDLRQLPG  RQPQAGLSQA  NFTLGPVSRS   60
YGGQYRCYGA  HNLSSECSAP  SDPLDILITG  QIRGTPFISV  QPGPTVASGE  NVTLLCQSWR  120
QFHTFLLTKA  GAADAPLRLR  SIHEYPKYQA  EFPMSPVTSA  HAGTYRCYGS  LNSDPYLLSH  180
PSEPLEL                                                                187

SEQ ID NO: 77           moltype = DNA   length = 1956
FEATURE                 Location/Qualifiers
source                  1..1956
                        mol_type = other DNA
                        organism = synthetic construct
SEQUENCE: 77
atgacgccga ttctcacagt tcttatatgc ctgggcctgt ccctggggcc gagaacgcat   60
gtgcaggcgg ggcatttgcc taaaccaacg ctttgggcgg aacctggcag cgttataacc  120
caggggagtc ctgtcactct gagatgccaa ggtggccagg agactcagga gtaccgcttg  180
taccgcgaga agaagaccgc tccctggatc actaggatac gcaggagct cgttaagaaa  240
gggcagtttc cgataccgtc aattacatgg agcatactg gcagatatcg gtgttactac  300
ggaagtgaca ccgctgggcg atctgagagc tcagacccgc ttgagctggt ggtgaccgga  360
gcttatataa aacccacttt gagcgcacaa ccgtctcctg tagttaatag tggggggaac  420
gtaaccctcc agtgtgatag tcaagtagcc ttcgacggtt ttatcctctg taaagagggg  480
gaagatgaac ccccagtg cctgaactct cagccacatg cacggggatc tagtcgcgct  540
atatttagcg ttgaccagt ttcaccgagc cgcagatggt ggtataggtg ctacgcttat  600
gatagtaact ctccgtatga tggtccttg ccgagcgact tgcttgagtt gctggtactc  660
ggggtcagca agaaacccag cttgagcgtg cagcctggtc ccatagtagc tccagaagaa  720
accctcacac tgcagtgtgg cagtgacgct gggtacaaca ggttcgtcct ttacaaagat  780
ggggaaagag acttttttgca gcttgcgggt gcacaacccc aggctggcct tagtcaggct  840
aacttcactt tgggaccggt tcaaggtct tacggcggtca agtacaggtg ctacggggca  900
cacaaccttta gctcagaatg tccgccccc tctgatcccc tggatatcct catcgcaggt  960
cagttttatg accgagtttc actgtcagtg caaccaggac caacggtagc ttctgctgag 1020
aatgtaactc ttctgtgcca gagccaggc tggatgcaaa cgttccttct cactaaggag 1080
ggagcggcag acgacccgtg gaggctgcga agtacgtacc agtcacaaaa atatcaggcg 1140
gagtttccaa tgggcccagt gacttctgcc catgcgggca cgtacagatg ctatgggagc 1200
caatcatcaa aaccttaccct tctcacgcac ccgtctgacc ctttggaact ccaattggtt 1260
gtaagtggtc cctccggtgg gcctagctca cctacaacag gccctactag tacgtctggc 1320
ccggaagatc agccccctgac tccgacaggg tcagacccac aatccggtct tggagggcac 1380
ctcggggtcg tcatcggat actggtggcc gtaattctcc ttcttctgct gttgcttctc 1440
ctctttcttta ttcttcgaca taggcgacaa gggaagcatt ggacttccac acagagaaaa 1500
gcggattttc agcatcctgc cggggccgtg ggcctgaac ccacggatcg gggtctccag 1560
tggcgatcct ctcctgcagc ggacgctcaa gaagaaaatc tctacgcggc ggttaaacat 1620
acgcagcctg aagatggagt tgaaatggat actcgcaagc cgcatgacga ggacccgcag 1680
gcagtaacat acgctgaagt taagcatagc cgaccgagac gcgagatggc ttctccaccg 1740
agccccctttt ccggtgagtt tttggacacc aaggaccgcc aagccgagga agatagcag 1800
atggacacgg aggccgctgc atccgaagcc cacaagatg tgacctacgc gcagttgcac 1860
agccttacgc tccgccgcga ggctactgag cccccacctt cccaggaagg accgtccccc 1920
gcagtccgt ccatttatgc tactttggca atccac                              1956

SEQ ID NO: 78           moltype = AA    length = 652
FEATURE                 Location/Qualifiers
source                  1..652
                        mol_type = protein
                        organism = synthetic construct
SEQUENCE: 78
MTPILTVLIC  LGLSLGPRTH  VQAGHLPKPT  LWAEPGSVIT  QGSPVTLRCQ  GGQETQEYRL   60
YREKKTAPWI  TRIPQELVKK  GQFPIPSITW  EHTGRYRCYY  GSDTAGRSES  SDPLELVVTG  120
AYIKPTLSAQ  PSPVVNSGGN  VTLQCDSQVA  FDGFILCKEG  EDEHPQCLNS  QPHARGSSRA  180
IFSVGPVSPS  RRWWYRCYAY  DSNSPYEWSL  PSDLLELVVL  GVSKKPSLSV  QPGPIVAPEE  240
TLTLQCGSDA  GYNRFVLYKD  GERDFLQLAG  AQPQAGLSQA  NFTLGPVSRS  YGGQYRCYGA  300
HNLSSEWSAP  SDPLDILIAG  QFYDRVSLSV  QPGPTVASGE  NVTLLCQSQG  WMQTFLLTKE  360
GAADDPWRLR  STYQSQKYQA  EFPMGPVTSA  HAGTYRCYGS  QSSKPYLLTH  PSDPLELQLV  420
VSGPSGGPSS  PTTGPTSTSG  PEDQPLTPTG  SDPQSGLGRH  LGVVIGILVA  VILLLLLLL  480
LFLILRHRRQ  GKHWTSTQRK  ADFQHPAGAV  GPEPTDRGLQ  WRSSPAADAQ  EENLYAAVKH  540
TQPEDGVEMD  TRSPHDEDPQ  AVTYAEVKHS  RPRREMASPP  SPLSGEFLDT  KDRQAEEDRQ  600
MDTEAAASEA  PQDVTYAQLH  SLTLRREATE  PPPSQEGPSP  AVPSIYATLA  IH          652

SEQ ID NO: 79           moltype = DNA   length = 54
FEATURE                 Location/Qualifiers
source                  1..54
                        mol_type = other DNA
                        organism = synthetic construct
SEQUENCE: 79
gaaggccgag ggagcctgct gacatgtggc gatgtggagg aaaacccagg acca            54

SEQ ID NO: 80           moltype = DNA   length = 999
FEATURE                 Location/Qualifiers
source                  1..999
                        mol_type = other DNA
                        organism = synthetic construct
SEQUENCE: 80
atgccaccac ctcgcctgct gttctttctg ctgttcctga cacctatgga ggtgcgacct   60
gaggaaccac tggtcgtgaa ggtcgaggaa ggcgacaatg ccgtgctgca gtgcctgaaa  120
```

```
ggcacttctg atgggccaac tcagcagctg acctggtcca gggagtctcc cctgaagcct   180
tttctgaaac tgagcctggg actgccagga ctgggaatcc acatgcgccc tctggctatc   240
tggctgttca tcttcaacgt gagccagcag atgggaggat tctacctgtg ccagccagga   300
ccaccatccg agaaggcctg gcagcctgga tggaccgtca acgtggaggg gtctggagaa   360
ctgttttaggt ggaatgtgag tgacctggga ggactggtga gtgggctgaa gaaccgctcc   420
tctgaaggcc caagttcacc ctcagggaag ctgatgagcc caaaactgta cgtgtgggcc   480
aaagatcggc ccgagatctg ggagggagaa cctccatgcc tgccacctag agacagcctg   540
aatcagagtc tgtcacagga tctgacaatg gcccccgggt ccactctgtg gctgtcttgt   600
ggagtcccac ccgacagcgt gtccagaggc cctctgtcct ggacccacgt gcatcctaag   660
gggccaaaaa gtctgctgtc actggaactg aaggacgatc ggcctgccag agacatgtgg   720
gtcatggaga ctggactgct gctgccacga gcaaccgcac aggatgctgg aaaatactat   780
tgccaccggg gcaatctgac aatgtccttc catctggaga tcactgcaag gcccgtgctg   840
tggcactggc tgctgcgaac cggaggatgg aaggtcagtg ctgtgacact ggcatatctg   900
atcttttgcc tgtgctccct ggtgggcatt ctgcatctgc agagagccct ggtgctgcgg   960
agaaagagaa agagaatgac tgacccaaca agaaggttt                          999

SEQ ID NO: 81            moltype = DNA  length = 1470
FEATURE                  Location/Qualifiers
source                   1..1470
                         mol_type = other DNA
                         organism = synthetic construct
SEQUENCE: 81
atgacgccga ttctcacagt tcttatatgc ctgggcctgt ccctggggcc gagaacgcat    60
gtgcaggcgg ggcatttgcc taaaccaacg ctttgggcgg aacctggcag cgttataacc   120
caggggagtc ctgtcactct gagatgccaa ggtggcagg agactcagga gtaccgcttg    180
taccgcgaga agaagaccgc tccctggatc actaggatac gcaggagcct cgttaagaaa   240
gggcagtttc cgataccgtc aattacatgg gagcatactg gcagatatcg gtgttactac   300
ggaagtgaca ccgctgggcg atctgagagc tcagacccgc ttgagctggt ggtgaccgga   360
gcttatataa aacccacttt gagcgcacaa ccgtctcctg tagttaatag tgggggaac    420
gtaaccctcc agtgtgatag tcaagtagcc ttcgacggtt ttatcctctg taaagaggg    480
gaagatgaac cccccagtgt cctgaactct cagccacatg cacggggatc tagtcgcgct   540
atatttagcg ttgaccagt ttcaccgagc cgcagatggt ggtataggtg ctacgcttat    600
gatagtaact ctccgtatga atggtccttg ccgagcgact tgcttgagtt gctggtactc   660
ggggtcagca agaaacccag cttgagcgtg cagcctggtc ccatagtagc tccagaagaa   720
accctcacac tgcagtgtgg cagtgacgct gggtacaaca ggttcgtcct ttacaaagat   780
ggggaaagag actttttgca gcttgcgggt gcacaacccc aggctggcct tagtcaggct   840
aacttcactt tgggaccggt gtcaaggtct tacggcggcc agtacaggtg ctacgggca   900
cacaaccttg gctcagaatg gtccgccccc tctgatcccc tggatatcct catcgcaggt   960
cagtttttatg accgagtttc actgtcagtg caaccaggac caacggtagc ttctggcgag  1020
aatgtaactc ttctgtgcca gagccagggc tggatgcaaa cgttccttct cactaaggag  1080
ggagcggcag acgaccgtg gaggctgcga agtacgtacc agtcacaaaa atatcaggcg  1140
gagtttccaa tgggcccagt gacttctgcc catgcgggca cgtacagatg ctatgggagc  1200
caatcatcaa aaccttacct tctcacgcac ccgtctgacc ctttggaact ccaattggtt  1260
gtaagtggtc cctccggtgg gcctagctca cctacaacag gccctactag tacgtctggc  1320
ccggaagatc agccctgac tccgacaggg tcagacccac aatccggtct tgggaggcac  1380
ctcggggtcg tcatcgggat actggtggcc gtaattctcc ttcttctgct gttgcttctc  1440
ctctttctta ttcttcgaca taggcgacaa                                   1470

SEQ ID NO: 82            moltype = AA  length = 490
FEATURE                  Location/Qualifiers
source                   1..490
                         mol_type = protein
                         organism = synthetic construct
SEQUENCE: 82
MTPILTVLIC LGLSLGPRTH VQAGHLPKPT LWAEPGSVIT QGSPVTLRCQ GGQETQEYRL     60
YREKKTAPWI TRIPQELVKK GQFPIPSITW EHTGRYRCYY GSDTAGRSES SDPLELVVTG    120
AYIKPTLSAQ PSPVVNSGGN VTLQCDSQVA FDGFILCKEG EDEHPQCLNS QPHARGSSRA    180
IFSVGPVSPS RRWWYRCYAY DSNSPYEWSL PSDLLELLVL GVSKKPSLSV QPGPIVAPEE    240
TLTLQCGSDA GYNRFVLYKD GERDFLQLAG AQPQAGLSQA NFTLGPVSRS YGGQYRCYGA    300
HNLSSEWSAP SDPLDILIAG QFYDRVSLSV QPGPTVASGE NVTLLCQSQG WMQTFLLTKE    360
GAADDPWRLR STYQSQKYQA EFPMGPVTSA HAGTYRCYGS QSSKPYLLTH PSDPLELQLV    420
VSGPSGGPSS PTTGPTSTSG PEDQPLTPTG SDPQSGLGRH LGVVIGILVA VILLLLLLLL    480
LFLILRHRRQ                                                          490

SEQ ID NO: 83            moltype = DNA  length = 126
FEATURE                  Location/Qualifiers
source                   1..126
                         mol_type = other DNA
                         organism = synthetic construct
SEQUENCE: 83
aaaagaggaa gaaaaagtt gctgtatata tttaaacaac catttatgag accagtgcaa     60
accacccaag aagaagacgg atgttcatgc agattcccag aagaagaaga aggaggatgt   120
gaattg                                                              126

SEQ ID NO: 84            moltype = DNA  length = 664
FEATURE                  Location/Qualifiers
source                   1..664
                         mol_type = other DNA
                         organism = synthetic construct
```

SEQUENCE: 84
```
atgacgccga ttctcacagt tcttatatgc ctgggcctgt ccctgggcc gagaacgcat    60
gtgcaggcgg ggcatttgcc taaaccaacg ctttgggcgg aacctggcag cgttataacc   120
caggggagtc ctgtcactct gagatgccaa ggtggcagg agactcagga gtaccgcttg    180
taccgcgaga agaagaccgc tccctggatc actaggatac cgcaggagct cgttaagaaa   240
gggcagtttc cgataccgtc aattacatgg gagcatactg gcagatatcg gtgttactac   300
ggaagtgaca ccgctgggcg atctgagagc tcagacccgc ttgagctggt ggtgaccgga   360
gcttatataa aacccacttt gagcgcacaa ccgtctcctg tagttaatag tgggggggaac  420
gtaaccctcc agtgtgatag tcaagtagcc ttcgacggtt ttatcctctg taaagagggg   480
gaagatgaac accccagtg cctgaactct cagccacatg cacggggatc tagtcgcgct    540
atatttagcg ttggaccagt ttcaccgagc cgcagatggt ggtataggtg ctacgcttat   600
gatagtaact ctccgtatga atggtccttg ccgagcgact tgcttgagtt gctggtactc   660
gggc                                                                664
```

| SEQ ID NO: 85 | moltype = DNA  length = 213 |
|---|---|
| FEATURE | Location/Qualifiers |
| source | 1..213 |
| | mol_type = other DNA |
| | organism = synthetic construct |

SEQUENCE: 85
```
gttgtaagtg gtccctccgg tgggcctagc tcacctacaa caggccctac tagtacgtct    60
ggcccggaag atcagcccct gactccgaca gggtcagacc cacaatccgg tcttgggagg   120
cacctcgggg tcgtcatcgg gatactggtg gccgtaattc tccttcttct gctgttgctt   180
ctcctctttc ttattcttcg acataggcga caa                                 213
```

| SEQ ID NO: 86 | moltype = DNA  length = 237 |
|---|---|
| FEATURE | Location/Qualifiers |
| source | 1..237 |
| | mol_type = other DNA |
| | organism = synthetic construct |

SEQUENCE: 86
```
cccgcgccac gaccaccaac accagcccca accattgcat cccagccttt gtctctccgg    60
cccgaggctt gtcgacctgc agctgggggt gccgtccata cccgaggcct ggacttcgcc   120
tgcgatatat atatttgggc tcctctggcc ggtacctgcg cgtactgct cctgtcactg    180
gtaataaccc tgtattgcaa tcacaggaac agaaggagag tctgtaagtg cccccgg      237
```

| SEQ ID NO: 87 | moltype = DNA  length = 1800 |
|---|---|
| FEATURE | Location/Qualifiers |
| source | 1..1800 |
| | mol_type = other DNA |
| | organism = synthetic construct |

SEQUENCE: 87
```
atgacccta tagttacagt cttgatctgt ctcgggctta gcttgggacc tcgaacgcat     60
gtacagacgg gcacaattcc taagcccacc ctctgggctg agcccgactc agtgataacg   120
cagggttctc cagttaccct ctcttgccaa ggctctcttg aggcccaaga gtaccggctg   180
taccgagaga agaagtccgc ctcctggatc actaggatca gaccggagct tgtgaagaac   240
ggccaattc atatcccgag catcacatgg gagcatactg ggcgctacgg atgccagtac    300
tatagtcgcg ccaggtggtc cgaactcagc gatccgcttg tccttgtcat gacgggtgct   360
tacccgaagc caacccttc agcacagccg tcaccagtag taacatccgg cggtagggtg    420
actctgcaat gcgagtccca agtggcattc ggtgggttca tactctgtaa agagggcgag   480
gacgaacatc ctcagtgcct taatagccaa ccccacgac gcggtagtag ccgagccata    540
ttctctgtag gtccggtgtc cccgaatagg cggtggtcac acagatgtta tggatatgat   600
ctcaatagcc cgtacgttg gtctagccct agtgatcttc tagagttgct tgttccagga    660
gtgagcaaga aacctagttt gtctgttcag cctgggcccg tgatggctcc tggcgaatcc   720
cttactcttc agtgcgttag cgacgtagga tatgatcgat ttgtactcta taaggaagga   780
gagcgcgatc ttagacagct tccaggccga cagccacagg ctggattgag ccaagctaat   840
tttacattgg gaccgtcag tcggtcttac ggggccaat acagatgcta tggcgcccac    900
aatctcagca gcgagtgctc agctccctcc gacccacttg atatattgat cactggtcaa   960
atcagggaa cgcccttat cagcgtgcag ccaggcccaa ccgtggcttc cggggagaat     1020
gttacactcc tgtgtcagtc ttggaggcaa ttccacacct ttcttctcac caaggcggga   1080
gccgcagacg cgcctctgcg attgcggtct atccatgaat atccgaaata tcaggccgag   1140
ttccctatgt ctcccgtcac gagcgcccat gccggcactt atcgctgcta cgggtcattg   1200
aactcagacc cgtacttgct tagccatccc tctgagcccc ttgaacttca attggtagtg   1260
tccggtcctt caatgggcag tagtcctcca ccaacaggac caatatcaac gccggctgga   1320
ccagaagacc agcctcttac cccaactggt tctgacccgc aatccggact cgggcggcac   1380
ttgggtgtag tgattggcat attggtggcc gtagtactcc tcctcttgct cctcctcttg   1440
ctgttcctga ttctcaggca tcggaggcag ggaaagcact ggacgtcaac gcagcgcaag   1500
gcggactttc agcatccagc gggggctgtc ggtccggagc cgacggaccg tggacttcag   1560
tggaggtcct caccggcagc tgacgctcaa gaagagaatc tgtatgcagc ggttaaagat   1620
acacaacctg aagatggagt ggagatggat acccgggctg cagcatcaga ggcgccacag   1680
gacgttacct atgcacaact gcactctctc actcttcgga gaaaagcaac cgaacccct    1740
ccaagtcagg aacgggagcc gcctgctgaa ccaagtatct atgctacgct tgcaatccac   1800
```

| SEQ ID NO: 88 | moltype = AA  length = 600 |
|---|---|
| FEATURE | Location/Qualifiers |
| source | 1..600 |
| | mol_type = protein |
| | organism = synthetic construct |

SEQUENCE: 88

```
MTPIVTVLIC LGLSLGPRTH VQTGTIPKPT LWAEPDSVIT QGSPVTLSCQ GSLEAQEYRL    60
YREKKSASWI TRIRPELVKN GQFHIPSITW EHTGRYGCQY YSRARWSELS DPLVLVMTGA   120
YPKPTLSAQP SPVVTSGGRV TLQCESQVAF GGFILCKEGE DEHPQCLNSQ PHARGSSRAI   180
FSVGPVSPNR RWSHRCYGYD LNSPYVWSSP SDLLELLVPG VSKKPSLSVQ PGPVMAPGES   240
LTLQCVSDVG YDRFVLYKEG ERDLRQLPGR QPQAGLSQAN FTLGPVSRSY GGQYRCYGAH   300
NLSSECSAPS DPLDILITGQ IRGTPFISVQ PGPTVASGEN VTLLCQSWRQ FHTFLLTKAG   360
AADAPLRLRS IHEYPKYQAE FPMSPVTSAH AGTYRCYGSL NSDPYLLSHP SEPLELQLVV   420
SGPSMGSSPP PTGPISTPAG PEDQPLTPTG SDPQSGLGRH LGVVIGILVA VVLLLLLLLL   480
LFLILRHRRQ GKHWTSTQRK ADFQHPAGAV GPEPTDRGLQ WRSSPAADAQ EENLYAAVKD   540
TQPEDGVEMD TRAAASEAPQ DVTYAQLHSL TLRRKATEPP PSQEREPPAE PSIYATLAIH   600

SEQ ID NO: 89           moltype = DNA   length = 1470
FEATURE                 Location/Qualifiers
source                  1..1470
                        mol_type = other DNA
                        organism = synthetic construct
SEQUENCE: 89
atgacccta tagttacagt cttgatctgt ctcgggctta gcttgggacc tcgaacgcat     60
gtacagacgg gcacaattcc taagcccacc ctctgggctg agcccgactc agtgataacg    120
cagggttctc cagttaccct ctcttgccaa ggctctcttg aggcccaaga gtaccggctg    180
taccgagaga agaagtccgc ctcctggatc actaggatca gaccggagct tgtgaagaac    240
ggccaatttc atatcccgag catcacatgg agcatactgg ggcgctacgg atgccagtac    300
tatagtcgcg ccaggtggtc cgaactcagc gatccgcttg tccttgtcat gacgggtgct    360
tacccgaagc caacccttc agcacagccg tcaccagtag taacatccgg cggtagggtg    420
actctgcaat gcgagtccca agtggcattc ggtgggttca tactctgtaa agagggcgag    480
gacgaacatc ctcagtgcct taatagccaa ccccacgcac gcggtagtag ccgagccata    540
ttctctgtag gtccggtgtc cccgaatagg cggtggtcac acagatgtta tggatatgat    600
ctcaatagcc cgtacgtttg gtctagccct agtgatcttc tagagttgct tgttccagga    660
gtgagcaaga aacctagttt gtctgttcag cctgggcccg tgatggctcc tggcgaatcc    720
cttactcttc agtgcgttag cgacgtagga tatgatcgat ttgtactcta taaggaagga    780
gagcgcgatc ttagacagct tccaggccga cagccacagg ctggattgag ccaagctaat    840
tttacattgg gaccgtcag tcggtcttac gggggccaat acagatgcta tggcgcccac    900
aatctcagca gcgagtgctc agctccctcc gacccacttg atatattgat cactggtcaa    960
atcagggaa cgcccttat cagcgtgcag ccaggcccca ccgtggcttc cggggagaat   1020
gttacactcc tgtgtcagtc ttggaggcaa ttccacacct tcttctcac caaggcggga   1080
gccgcagacg cgcctctgcg attgcggtct atccatgaat atccgaaata tcaggccgag   1140
ttccctatgt ctcccgtcac gagcgcccat gccggcactt atcgctgcta cgggtcattg   1200
aactcagacc cgtacttgct tagccatccc tctgagcccc ttgaacttca attggtagtg   1260
tccggtccttt caatgggcag tagtcctcca ccaacaggac caatatcaac gccggctgga   1320
ccagaagacc agcctcttac cccaactggt tctgacccgc aatccggact cgggcggcac   1380
ttgggtgtag tgattggcat attggtggcc gtagtactcc tcctcttgct cctcctcttg   1440
ctgttcctga ttctcaggca tcggaggcag                                   1470

SEQ ID NO: 90           moltype = AA    length = 490
FEATURE                 Location/Qualifiers
source                  1..490
                        mol_type = protein
                        organism = synthetic construct
SEQUENCE: 90
MTPIVTVLIC LGLSLGPRTH VQTGTIPKPT LWAEPDSVIT QGSPVTLSCQ GSLEAQEYRL    60
YREKKSASWI TRIRPELVKN GQFHIPSITW EHTGRYGCQY YSRARWSELS DPLVLVMTGA   120
YPKPTLSAQP SPVVTSGGRV TLQCESQVAF GGFILCKEGE DEHPQCLNSQ PHARGSSRAI   180
FSVGPVSPNR RWSHRCYGYD LNSPYVWSSP SDLLELLVPG VSKKPSLSVQ PGPVMAPGES   240
LTLQCVSDVG YDRFVLYKEG ERDLRQLPGR QPQAGLSQAN FTLGPVSRSY GGQYRCYGAH   300
NLSSECSAPS DPLDILITGQ IRGTPFISVQ PGPTVASGEN VTLLCQSWRQ FHTFLLTKAG   360
AADAPLRLRS IHEYPKYQAE FPMSPVTSAH AGTYRCYGSL NSDPYLLSHP SEPLELQLVV   420
SGPSMGSSPP PTGPISTPAG PEDQPLTPTG SDPQSGLGRH LGVVIGILVA VVLLLLLLLL   480
LFLILRHRRQ                                                         490

SEQ ID NO: 91           moltype = DNA   length = 660
FEATURE                 Location/Qualifiers
source                  1..660
                        mol_type = other DNA
                        organism = synthetic construct
SEQUENCE: 91
atgacccta tagttacagt cttgatctgt ctcgggctta gcttgggacc tcgaacgcat     60
gtacagacgg gcacaattcc taagcccacc ctctgggctg agcccgactc agtgataacg    120
cagggttctc cagttaccct ctcttgccaa ggctctcttg aggcccaaga gtaccggctg    180
taccgagaga agaagtccgc ctcctggatc actaggatca gaccggagct tgtgaagaac    240
ggccaatttc atatcccgag catcacatgg agcatactgg ggcgctacgg atgccagtac    300
tatagtcgcg ccaggtggtc cgaactcagc gatccgcttg tccttgtcat gacgggtgct    360
tacccgaagc caacccttc agcacagccg tcaccagtag taacatccgg cggtagggtg    420
actctgcaat gcgagtccca agtggcattc ggtgggttca tactctgtaa agagggcgag    480
gacgaacatc ctcagtgcct taatagccaa ccccacgcac gcggtagtag ccgagccata    540
ttctctgtag gtccggtgtc cccgaatagg cggtggtcac acagatgtta tggatatgat    600
ctcaatagcc cgtacgtttg gtctagccct agtgatcttc tagagttgct tgttccagga    660

SEQ ID NO: 92           moltype = DNA   length = 216
FEATURE                 Location/Qualifiers
```

```
source                   1..216
                         mol_type = other DNA
                         organism = synthetic construct
SEQUENCE: 92
gtagtgtccg gtccttcaat gggcagtagt cctccaccaa caggaccaat atcaacgccg    60
gctggaccag aagaccagcc tcttacccca actggttctg acccgcaatc cggactcggg   120
cggcacttgg gtgtagtgat tggcatattg gtggccgtag tactcctcct cttgctcctc   180
ctcttgctgt tcctgattct caggcatcgg aggcag                             216

SEQ ID NO: 93            moltype = DNA  length = 1251
FEATURE                  Location/Qualifiers
source                   1..1251
                         mol_type = other DNA
                         organism = synthetic construct
SEQUENCE: 93
atgacgccga ttctcacagt tcttatatgc ctgggcctgt ccctggggcc gagaacgcat    60
gtgcaggcgg ggcatttgcc taaaccaacg ctttgggcgg aacctggcag cgttataacc   120
cagggagtc ctgtcactct gagatgccaa ggtggccaga gactcagga gtaccgcttg    180
taccgcgaga agaagaccgc tccctggatc actaggatac cgcaggagct cgttaagaaa   240
gggcagtttc cgataccgtc aattacatgg gagcatactg gcagatatcg gtgttactac   300
ggaagtgaca ccgctgggcg atctgagagc tcagacccgc ttgagctggt ggtgaccgga   360
gcttatataa aacccacttt gagcgcacaa ccgtctccta tagttaatag tgggggaac    420
gtaaccctcc agtgtgatag tcaagtagcc ttcgacggtt ttatcctctg taaagagggg   480
gaagatgaac cccccagtg cctgaactct cagccacatg cacggggatc tagtcgcgct   540
atatttagcg ttgaccagt ttcaccgagc cgcagatggt ggtataggtg ctacgcttat    600
gatagtaact ctccgtatga atggtccttg ccgagcgact tgcttgagtt gctggtactc   660
ggggtcagca agaaacccag cttgagcgtg cagcctggtc ccatagtagc tccagaagaa   720
accctcacac tgcagtgtgg cagtgacgct gggtacaaca ggtcgtcct ttacaaagat    780
ggggaaagag acttttttgca gcttgcgggt gcacaacccc aggctggcct tagtcaggct   840
aacttcactt tgggaccggt gtcaaggtct tacggcggca gtacaggtg ctacggggca    900
cacaacctta gctcagaatg tccgccccc tctgatcccc tggatatcct catcgcaggt    960
cagttttatg accgagtttc actgtcagtg caaccaggac caacggtagc ttctggcgag  1020
aatgtaactc ttctgtgcca gagccagggc tggatgcaaa cgttccttct cactaaggag  1080
ggagcggcag acgacccgtg gaggctgcga agtacgtacc agtcgcaaaa atatcaggcg  1140
gagttttccaa tgggcccagt gacttctgcc catgcgggca cgtacagatg ctatgggagc  1200
caatcatcaa aaccttacct tctcacgcac ccgtctgacc ctttggaact c            1251

SEQ ID NO: 94            moltype = AA  length = 417
FEATURE                  Location/Qualifiers
source                   1..417
                         mol_type = protein
                         organism = synthetic construct
SEQUENCE: 94
MTPILTVLIC LGLSLGPRTH VQAGHLPKPT LWAEPGSVIT QGSPVTLRCQ GGQETQEYRL    60
YREKKTAPWI TRIPQELVKK GQFPIPSITW EHTGRYRCYY GSDTAGRSES SDPLELVVTG   120
AYIKPTLSAQ PSPVVNSGGN VTLQCDSQVA FDGFILCKEG EDEHPQCLNS QPHARGSSRA   180
IFSVGPVSPS RRWWYRCYAY DSNSPYEWSL PSDLLELVVL GVSKKPSLSV QPGPIVAPEE   240
TLTLQCGSDA GYNRFVLYKD GERDFLQLAG AQPQAGLSQA NFTLGPVSRS YGGQYRCYGA   300
HNLSSEWSAP SDPLDILIAG QFYDRVSLSV QPGPTVASGE NVTLLCQSQG WMQTFLLTKE   360
GAADDPWRLR STYQSQKYQA EFPMGPVTSA HAGTYRCYGS QSSKPYLLTH PSDPLEL      417

SEQ ID NO: 95            moltype = DNA  length = 1249
FEATURE                  Location/Qualifiers
source                   1..1249
                         mol_type = other DNA
                         organism = synthetic construct
SEQUENCE: 95
atgacccta tagttacagt cttgatctgt ctcgggctta gcttgggacc tcgaacgcat    60
gtacagacgg gcacaattcc taagcccacc ctctgggctg agcccgactc agtgataacg   120
cagggttctc cagttaccct ctcttgccaa ggctctcttg aggcccaaga gtaccggctg   180
taccgagaga agaagtccgc ctcctggatc actaggatca gaccggagct tgtgaagaac   240
ggccaatttc atatcccgag catcacatgg gagcatactg ggcgctacgg atgccagtac   300
tatagtcgcg ccaggtggtc cgaactcagc gatccgcttg tccttgtcat gacgggtgct   360
tacccgaagc caacccttc agcacagccg tcaccagtag taacatccgg cggtagggtg   420
actctgcaat gcgagtccca gtggcattc ggtgggttca tactctgtaa agagggcgag   480
gacgaacatc ctcagtgcct taatagccaa cccacgcac gcgtagtag ccgagccata    540
ttctctgtag gtccggtgtc cccgaatagg cggtggtcac acagatgtta tggatatgat   600
ctcaatagcc cgtacgtttg gtctagccct agtgatcttc tagagttgtc tgttccagga   660
gtgagcaaga aactagttt gtctgttcag cctgggccg tgatggctcc tggcgaatcc   720
cttactcttc agtgcgttag cgacgtagga tatgatcgat ttgtactcta taggaagga    780
gagcgcgatc ttagacagct tccaggccga cagccacagg ctggattgag ccaagctaat   840
tttacattgg gacccgtcag tcggtcttac ggggccaat acagatgcta tggcgcccac   900
aatctcagca gcgagtgctc agctccctcc gacccacttg atatattgat cactggtcaa   960
atcagggaa cgcccttat cagcgtgcag ccaggcccaa ccgtggcttc aggggagaat  1020
gttacactcc tgtgtcagtc ttggaggcaa ttccacacct tcttctcac caaggcggga  1080
gccgcagacg cgcctctgcg attgcggtct atccatgaat atccgaaata tcaggccgag  1140
ttccctatgt ctcccgtcac gagcgcccat gccggcactt atcgctgcta cgggtcattg  1200
aactcagacc cgtacttgct tagccatccc tctgagcccc ttgaacttc              1249
```

```
SEQ ID NO: 96          moltype = AA   length = 416
FEATURE                Location/Qualifiers
source                 1..416
                       mol_type = protein
                       organism = synthetic construct
SEQUENCE: 96
MTPIVTVLIC LGLSLGPRTH VQTGTIPKPT LWAEPDSVIT QGSPVTLSCQ GSLEAQEYRL   60
YREKKSASWI TRIRPELVKN GQFHIPSITW EHTGRYGCQY YSRARWSELS DPLVLVMTGA  120
YPKPTLSAQP SPVVTSGGRV TLQCESQVAF GGFILCKEGE DEHPQCLNSQ PHARGSSRAI  180
FSVGPVSPNR RWSHRCYGYD LNSPYVWSSP SDLLELLVPG VSKKPSLSVQ PGPVMAPGES  240
LTLQCVSDVG YDRFVLYKEG ERDLRQLPGR QPQAGLSQAN FTLGPVSRSY GGQYRCYGAH  300
NLSSECSAPS DPLDILITGQ IRGTPFISVQ PGPTVASGEN VTLLCQSWRQ FHTFLLTKAG  360
AADAPLRLRS IHEYPKYQAE FPMSPVTSAH AGTYRCYGSL NSDPYLLSHP SEPLEL      416

SEQ ID NO: 97          moltype = DNA   length = 699
FEATURE                Location/Qualifiers
source                 1..699
                       mol_type = other DNA
                       organism = synthetic construct
SEQUENCE: 97
gttgacaagc gggtggagtc taagtatggt cccccatgtc ccagctgtcc cgcgcctccc   60
gtggcaggac catcagtctt cttgtttcca cctaagccaa aagacactct catgataagc  120
aggaccccgg aggtaacatg tgtcgtggtt gacgtttctc aagaggaccc ggaagtccaa  180
ttcaactggt acgttgacgg cgtggaagtc cataatgcaa agacgaagcc tagagaagag  240
caattccaga gcacatatcg cgtggtatcc gttttgacgg tacttcatca ggactggttg  300
aacggaaaag aatataagtg taaggtttca aataaagtc tgccctccag tatagaaaaa  360
actatctcca aggcgaaggg tcaaccaagg gagccgcagg tgtacacact cccgcctagt  420
caggaggaga tgactaaaaa tcaagtatct ttgacctgtc tggtgaaggg cttctatcct  480
tctgacatag ctgttgaatg ggaaagcaat ggtcagccag aaaacaacta taagactacc  540
ccaccgtac ttgatagtga cggaaagcttt tccttacta gccggctgac tgtagacaaa  600
tcccgatggc aggaaggga tgtatttagc tgtagcgtaa tgcacgaggc ccttcataat  660
cattacacgc agaaaagcct ttccctctcc ctcgaattg                        699

SEQ ID NO: 98          moltype = AA   length = 233
FEATURE                Location/Qualifiers
source                 1..233
                       mol_type = protein
                       organism = synthetic construct
SEQUENCE: 98
VDKRVESKYG PPCPSCPAPP VAGPSVFLFP PKPKDTLMIS RTPEVTCVVV DVSQEDPEVQ   60
FNWYVDGVEV HNAKTKPREE QFQSTYRVVS VLTVLHQDWL NGKEYKCKVS NKGLPSSIEK  120
TISKAKGQPR EPQVYTLPPS QEEMTKNQVS LTCLVKGFYP SDIAVEWESN GQPENNYKTT  180
PPVLDSDGSF FLYSRLTVDK SRWQEGNVFS CSVMHEALHN HYTQKSLSLS LEL         233

SEQ ID NO: 99          moltype = DNA   length = 111
FEATURE                Location/Qualifiers
source                 1..111
                       mol_type = other DNA
                       organism = synthetic construct
SEQUENCE: 99
atatatattt gggctcctct ggccggtacc tgcggcgtac tgctcctgtc actggtaata   60
accctgtatt gcaatcacag gaacagaagg agagtctgta agtgccccg g            111

SEQ ID NO: 100         moltype = AA   length = 37
FEATURE                Location/Qualifiers
source                 1..37
                       mol_type = protein
                       organism = synthetic construct
SEQUENCE: 100
IYIWAPLAGT CGVLLLSLVI TLYCNHRNRR RVCKCPR                            37

SEQ ID NO: 101         moltype = DNA   length = 363
FEATURE                Location/Qualifiers
source                 1..363
                       mol_type = other DNA
                       organism = synthetic construct
SEQUENCE: 101
gttgacaagc gggtggagtc taagtatggt cccccatgtc ccgtcaacc aagggagccg   60
caggtataca cactcccgcc tagtcaggag gagatgacta aaaatcaagt atctttgacc  120
tgtctggtga agggcttcta tccttctgac atagctgttg aatgggaaag caatggtcag  180
ccagaaaaca actataagac taccccaccc gtacttgata gtgacggaag cttttttcctt  240
tacagccggc tgactgtaga caaatcccga tggcaggaag gaatgtatt tagctgtagc  300
gtaatgcacg aggcccttca taatcattac acgcagaaaa gcctttccct ctccctcgaa  360
ttg                                                                363

SEQ ID NO: 102         moltype = AA   length = 121
FEATURE                Location/Qualifiers
source                 1..121
                       mol_type = protein
```

```
                             -continued organism = synthetic construct
SEQUENCE: 102
VDKRVESKYG PPCPGQPREP QVYTLPPSQE EMTKNQVSLT CLVKGFYPSD IAVEWESNGQ    60
PENNYKTTPP VLDSDGSFFL YSRLTVDKSR WQEGNVFSCS VMHEALHNHY TQKSLSLSLE   120
L                                                                  121

SEQ ID NO: 103         moltype = DNA   length = 81
FEATURE                Location/Qualifiers
source                 1..81
                       mol_type = other DNA
                       organism = synthetic construct
SEQUENCE: 103
ttttgggtgc tggtggtggt tgggggagtc ctggcttgct atagcttgct agtaacagtg    60
gcctttatta ttttctgggt g                                              81

SEQ ID NO: 104         moltype = AA   length = 27
FEATURE                Location/Qualifiers
source                 1..27
                       mol_type = protein
                       organism = synthetic construct
SEQUENCE: 104
FWVLVVVGGV LACYSLLVTV AFIIFWV                                        27

SEQ ID NO: 105         moltype = DNA   length = 117
FEATURE                Location/Qualifiers
source                 1..117
                       mol_type = other DNA
                       organism = synthetic construct
SEQUENCE: 105
attgaagtta tgtatcctcc tccttaccta gacaatgaga agagcaatgg aaccattatc    60
catgtgaaag ggaaacacct tgtccaagt cccctatttc ccggaccttc taagccc      117

SEQ ID NO: 106         moltype = AA   length = 39
FEATURE                Location/Qualifiers
source                 1..39
                       mol_type = protein
                       organism = synthetic construct
SEQUENCE: 106
IEVMYPPPYL DNEKSNGTII HVKGKHLCPS PLFPGPSKP                            39

SEQ ID NO: 107         moltype = AA   length = 42
FEATURE                Location/Qualifiers
source                 1..42
                       mol_type = protein
                       organism = synthetic construct
SEQUENCE: 107
PAPRPPTPAP TIASQPLSLR PEACRPAAGG AVHTRGLDFA CD                        42

SEQ ID NO: 108         moltype = AA   length = 5
FEATURE                Location/Qualifiers
source                 1..5
                       mol_type = protein
                       organism = synthetic construct
SEQUENCE: 108
SGGGS                                                                 5

SEQ ID NO: 109         moltype = AA   length = 5
FEATURE                Location/Qualifiers
source                 1..5
                       mol_type = protein
                       organism = synthetic construct
REGION                 5
                       note = The entire sequence of amino acids 1-5 can be
                        repeated one or more times
SEQUENCE: 109
GGGGS                                                                 5

SEQ ID NO: 110         moltype = AA   length = 5
FEATURE                Location/Qualifiers
source                 1..5
                       mol_type = protein
                       organism = synthetic construct
SEQUENCE: 110
MGCXC                                                                 5
```

What is claimed is:

1. A chimeric receptor protein, comprising:
   (a) a targeting region, that targets HLA-G, comprising an immunoglobulin-like transcript 4 (ILT4) D1-D2 extracellular domain that comprises an amino acid sequence that is 90% or more identical to SEQ ID NO: 57, wherein the targeting region lacks an ILT4 D3-D4 extracellular domain;
   (b) a CD8α stalk domain;
   (c) a CD8α transmembrane domain; and
   (d) an intracellular domain (ICD), comprising:
      (i) a signaling region capable of transducing a signal, upon binding of said targeting region to HLA-G, into the interior of an immune effector cell to elicit effector cell function, wherein the signaling region comprises a CD3ζ signaling domain; and
      (ii) a costimulatory region comprising a 4-1BB costimulatory domain.

2. The chimeric receptor protein of claim 1, wherein the targeting region comprises an amino acid mutation at a position corresponding to Y96 of the ILT4 amino acid sequence set forth in SEQ ID NO: 57.

3. An isolated nucleic acid, comprising a nucleotide sequence encoding the chimeric receptor protein of claim 1.

4. The isolated nucleic acid of claim 3, wherein said nucleic acid is an expression vector.

5. An isolated genetically modified cell, expressing the chimeric receptor protein of claim 1.

6. The isolated genetically modified cell of claim 5, wherein the genetically modified cell is a natural killer (NK) cell, a T cell, an iNKT cell, or a macrophage.

7. A method of treatment, comprising administering the genetically modified cell of claim 5 to an individual in need, wherein the individual has diseased cells that express HLA-G.

8. The method of claim 7, wherein the individual has a cancer with HLA-G expressing cancer cells.

9. A method of producing an isolated genetically modified cell, the method comprising:
   introducing the nucleic acid of claim 3 into an isolated cell or an isolated population of cells, thus producing an isolated genetically modified cell.

10. The chimeric receptor protein of claim 1, wherein the CD8α stalk domain comprises the amino acid sequence of SEQ ID NO: 107; the CD8α transmembrane domain comprises the amino acid sequence of SEQ ID NO: 100; the CD3ζ signaling domain comprises the amino acid sequence of SEQ ID NO: 33; and the 4-1BB costimulatory domain comprises the amino acid sequence of SEQ ID NO: 35.

11. The chimeric receptor protein of claim 1, wherein the ILT4 D1-D2 extracellular domain comprises an amino acid sequence that is 95% or more identical to SEQ ID NO: 57.

12. The chimeric receptor protein of claim 10, wherein the ILT4 D1-D2 extracellular domain comprises an amino acid sequence that is 95% or more identical to SEQ ID NO: 57.

13. The chimeric receptor protein of claim 1, wherein the ILT4 D1-D2 extracellular domain comprises the amino acid sequence of SEQ ID NO: 57.

14. The chimeric receptor protein of claim 10, wherein the ILT4 D1-D2 extracellular domain comprises the amino acid sequence of SEQ ID NO: 57.

15. The isolated nucleic acid of claim 3, wherein said nucleic acid is a plasmid, a viral vector, or a transposon.

16. The isolated nucleic acid of claim 3, wherein the nucleotide sequence encoding the chimeric receptor protein is operably linked to a constitutive promoter or to an inducible promoter.

17. The method of claim 7, wherein the individual is a human.

18. The method of claim 7, wherein the genetically modified cell is autologous to the individual.

19. The method of claim 7, wherein the genetically modified cell is allogeneic to the individual.

* * * * *